(12) United States Patent
Otterbein et al.

US007687079B2

(10) Patent No.: US 7,687,079 B2
(45) Date of Patent: Mar. 30, 2010

(54) METHODS OF TREATING ILEUS

(75) Inventors: Leo E. Otterbein, New Kensington, PA (US); Augustine M. K. Choi, Pittsburgh, PA (US); Beverley A. Moore, Pittsburgh, PA (US); Anthony J. Bauer, Pittsburgh, PA (US)

(73) Assignees: University of Pittsburgh of the Commonwealth System of Higher Education Yale University, Pittsburgh, PA (US); Yale University, New Haven, CT (US)

( * ) Notice: Subject to any disclaimer, the term of this patent is extended or adjusted under 35 U.S.C. 154(b) by 34 days.

(21) Appl. No.: 10/371,666

(22) Filed: Feb. 21, 2003

(65) Prior Publication Data

US 2003/0219497 A1 Nov. 27, 2003

Related U.S. Application Data

(60) Provisional application No. 60/372,652, filed on Apr. 15, 2002.

(51) Int. Cl.
 *A61K 33/00* (2006.01)
 *A61P 1/00* (2006.01)
(52) U.S. Cl. ..................................... 424/699
(58) Field of Classification Search ................. 424/699
 See application file for complete search history.

(56) References Cited

U.S. PATENT DOCUMENTS

| | | | |
|---|---|---|---|
| 4,053,590 A | 10/1977 | Bonsen et al. |
| 4,264,739 A | 4/1981 | Grabner et al. |
| 4,923,817 A | 5/1990 | Mundt |
| 5,084,380 A | 1/1992 | Carney |
| 5,180,366 A | 1/1993 | Woods |
| 5,240,912 A | 8/1993 | Todaro |
| 5,293,875 A | 3/1994 | Stone |
| 5,449,665 A | 9/1995 | Sollevi |
| 5,476,764 A | 12/1995 | Bitensky |
| 5,498,421 A | 3/1996 | Grinstaff et al. |
| 5,632,162 A | 5/1997 | Billy |
| 5,664,563 A | 9/1997 | Schroeder et al. |
| 5,731,326 A | 3/1998 | Hart et al. |
| 5,763,431 A | 6/1998 | Jackson |
| 5,792,325 A | 8/1998 | Richardson, Jr. |
| 5,882,674 A | 3/1999 | Herrmann et al. |
| 5,885,621 A | 3/1999 | Head et al. |
| 5,914,316 A | 6/1999 | Brown et al. |
| 6,066,333 A | 5/2000 | Willis et al. |
| 6,069,132 A | 5/2000 | Revanker et al. |
| 6,203,991 B1 | 3/2001 | Nabel et al. |
| 6,313,144 B1 | 11/2001 | McCullough et al. |
| 6,315,995 B1 | 11/2001 | Pinsky et al. |
| 6,316,403 B1 | 11/2001 | Pinsky et al. |
| 7,045,140 B2 | 5/2006 | Motterlini et al. |
| 7,238,469 B2 | 7/2007 | Bach et al. |
| 2002/0155166 A1 | 10/2002 | Choi et al. |
| 2003/0009127 A1 | 1/2003 | Trescony et al. |
| 2003/0064114 A1 | 4/2003 | Motterlini et al. |
| 2003/0068387 A1 | 4/2003 | Buelow et al. |
| 2003/0219496 A1 | 11/2003 | Otterbein et al. |
| 2004/0005367 A1 | 1/2004 | Otterbein et al. |
| 2004/0052866 A1 | 3/2004 | Otterbein et al. |
| 2004/0067261 A1 | 4/2004 | Haas et al. |
| 2004/0131703 A1 | 7/2004 | Bach et al. |
| 2004/0197271 A1 | 10/2004 | Kunka et al. |
| 2004/0228930 A1 | 11/2004 | Billiar et al. |
| 2004/0258772 A1 | 12/2004 | Otterbein et al. |
| 2005/0048133 A1 | 3/2005 | Pinsky et al. |
| 2005/0215468 A1 | 9/2005 | Bar-Or et al. |
| 2005/0250688 A1 | 11/2005 | Pinsky et al. |
| 2006/0003922 A1 | 1/2006 | Bach et al. |
| 2007/0202083 A1 | 8/2007 | Bach et al. |

FOREIGN PATENT DOCUMENTS

| | | |
|---|---|---|
| FR | 2 816 212 | 10/2002 |
| JP | 56079957 A | 6/1981 |
| WO | WO 94/22482 | 10/1994 |
| WO | WO 95/35105 | 12/1995 |
| WO | WO 98/08523 | 3/1998 |
| WO | WO 98/13058 | 4/1998 |
| WO | WO 99/49880 | 4/1999 |
| WO | WO 99/47512 | 9/1999 |
| WO | WO 02/09731 | 2/2002 |
| WO | WO 02/078684 | 10/2002 |
| WO | WO 02/092075 | 11/2002 |
| WO | WO 03/000114 | 1/2003 |
| WO | WO 03/072024 | 9/2003 |
| WO | WO 03/088923 | 10/2003 |
| WO | WO03/088981 | 10/2003 |
| WO | WO 03/094932 | 11/2003 |
| WO | WO 03/096977 | 11/2003 |
| WO | WO 03/103585 | 12/2003 |
| WO | WO 04/000368 | 12/2003 |
| WO | WO 2004/004817 | 1/2004 |
| WO | WO 2004/043341 | 5/2004 |

OTHER PUBLICATIONS

Moore et al.,"Inhaled carbon monoxide suppresses the development of postoperative ileus in the murine small intestine", Gastroenterology (2003), vol. 124, pp. 377-391.*

(Continued)

*Primary Examiner*—Johann R Richter
*Assistant Examiner*—Frank I. Choi
(74) *Attorney, Agent, or Firm*—Fish & Richardson P.C.

(57) ABSTRACT

The present invention relates to a method of treating ileus in a patient, which includes administering a pharmaceutical composition that includes carbon monoxide to the patient.

53 Claims, 16 Drawing Sheets

OTHER PUBLICATIONS

File Caplus, STN/CAS online, Acc. No. 1975:119753, Doc. No. 82:119753 (Lee et al., "Intestinal motility and absorption in acute carbon monoxide poisoning", Soul Uidae Chapchi (1974), vol. 15, No. 2, pp. 95-105), Abstract.*

File Biosis, STN/CAS online, Acc. No. 2003:582769, Doc. No. PREV200300572595 (Moore et al., Digestive Disease Week Abstracts and Itinerary Planner (2003), Vo. 2003, pp. Abstract No. M1337), Abstract.*

File Biosis, STN/CAS online, Acc. No. 2003:447765, Doc. No. PREV200300447765 (Nakao et al., Gut (2003), vol. 52, No. 9, pp. 1278-1285), Abstract.*

File Biosis, STN online, Acc. No. 2002:9995, Doc. No. PREV200200009995 (Huizinga,American Journal of Physiology (2001), vol. 281, No. 5 Part 1, pp. G1129-G1134), Abstract.*

File Biosis, STN online, Acc. No. 1998:132786, Doc. No. PREV199800132786 (Miller et al., Gastroenterology(1998), vol. 114, No. 2, pp. 239-244), Abstract.*

File Caplus, STN online, Acc. No. 2000:22654, Doc. No. 132:120276 (Farrugia et al., Microscopy Research and Technique (1999), vol. 47, No. 5, pp. 321-324), Abstract.*

Wing-Gaia et al., International Journal of Sport Nutrition and Exercise Metabolism (2005), vol. 15, pp. 680-688.*

Napolitano, Carbon monoxide and ileus: Inhaled gas to prevent retained gas?, Critcal Care Medicine (2005), vol. 33, No. 6, pp. 1445-1446.*

Abidin et al., "The Combined Effect of Carbon Monoxide and Normobaric Hyperoxia on Animals", Kosmicheskaya Biologiya I Aviakosmicheskaya Meditsina 6: 63-67 (1978).

Arita et al., "Prevention of Primary Islet Isograft Nonfunction in Mice with Pravastatin," *Transplantation* 65:1429-33 (1998).

Arnush et al., "IL-1 Produced and Released Endogenously within Human Islets Inhibits βCell Function," J. Clin Invest. 102:516-26 (1998).

Bach et al., "Accommodation of vascularized xenografts: Expression of "protective genes" by donor endothelial cells in a host Th2 cytokine environment," *Nature Med*. 3:196-204 (1997).

Berney et al., "Islet cell transplantation: the future?" *Langenbeck's Arch. Surg.* 385: 373-8 (2000).

Bentley et al., "Successful Cardiac Transplantation with Methanol or Carbon Monoxide-Poisoned Donors," *Thorac Surg* 71(4):1194-7 (2001).

Brouard et al., "Carbon Monoxide Generated by Heme Oxygenase-1 Suppresses Endothelial Cell Apoptosis," *J Exp Med* 192(7):1015-26 (2000).

Brown et al., "In vivo binding of carbon monoxide to cytochrome *c* oxidase in rat brain", American Physiological Society, pp. 604-610 (1990).

Campbell, "Living At Very High Altitudes", *The Lancet* 1:370-373 (1930).

Campbell, "The Effect of Carbon Monoxide and Other Agents Upon the Rate of Tumour Growth", J Pathology & Bacteriology 35:379-394 (1932).

Campell, "Cancer of Skin and Increase in Incidence of Primary Tumours of Lung in Mice Exposed to Dust Obtained from Tarred Roads", *Brit. J Exper. Pathol.* XV(5):24, 289-294 (1934).

Cantrell et al., "Low-Dose Carbon Monoxide Does Not Reduce Vasoconstriction in Isolated Rat Lungs", *Experimental Lung Research* 22:21-32 (1996).

Cardell et al., "Bronchondilatation in vivo by carbon monoxide, a cyclic GMP related messenger", British J. of Pharmacology 124:1065-1068 (1998).

Carlsson et al., "Measurements of Oxygen Tension in Native and Transplanted Rat Pancreatic Islets," *Diabetes* 47:1027-32 (1998).

Carraway et al., "Induction of ferritin and heme oxygenase-1 by endotoxin in the lung", *Am J Physiol Lung Cell Mol Physiol* 275:L583-592 (1998).

Cecil Textbook of Medicine (21$^{st}$ Ed. 2000) 1:273-279, 357-372, 387-419, 425-427, 436-448, 466-475, 507-512, 1060-1074.

Cecil Textbook of Medicine (21$^{st}$ Ed. 2000) 2:1492-1499, 2042-2047, 2079-2081.

Chapman et al., "Exogenous Carbon Monoxide Attenuates Aeroallergen-induced Eosinophilic Inflammation in Mice", *J Respiratory Critical Care Med* 159(3):A218 (1999).

Chapman et al., "Carbon Monoxide Attenuates Aeroallergen-induced Inflammation in Mice", *Am. J. Physiol. Lung Cell Mol Physiol.* 281:L209-L216 (2001).

Choi et al., "Heme Oxygenase-1: Function, Regulation, and Implication of a Novel Stress-inducible Protein in Oxidant-induced Lung Injury", *Am. J. Respir. Cell Mol. Biol.* 15:9-19 (1996).

Christodoulides et al., "Vascular Smooth Muscle Cell Heme Oxygenases Generate Guanylyl Cyclase-Stimulatory Carbon Monoxide," *Circulation* 97:2306-9 (1995).

Corbett et al., "Nitric oxide mediates cytokine-induced inhibition of insulin secretion by human islets of Langerhans," *Proc. Natl. Acad. Sci USA* 90:1731-5 (1993).

Davidson et al., "Inflammatory Modulation and Wound Repair" *J Investigative Dermatology* xi-xii (2003).

Dioum et al., "NPAS2: A Gas-Responsive Transcription Factor", *Sciencexpress*/www.sciencexpress.org/Nov. 21, 2002/pp. 1-6/10.1126/science.1078456.

Donnelly et al., "Expression of Heme-Oxygenase in Human Airway Primary Epithelial Cells", *J Respiratory Critical Care Med* 159(3):A218 (1999).

Friebe et al., "YC-1 Potentiates Nitic Oxide- and Carbon Monoxide-Induced Cyclic GMP Effects in Human Platelets", Molecular Pharmacology 54: 962-967 (1998).

Gaine et al., "Introduction of Heme Oxygenase-1 with Hemoglobin Depresses Vasoreactivity in Rat Aorta," *J Vasc Res* 36(2):114-9 (1999).

Grau et al., "Influence of Carboxyhemoglobin Level on Tumor Growth, Blood Flow, and Radiation Response in an Experimental Model," *Int. J. Radiation Oncology Biol. Phys.* 22:421-424 (1992).

Grau et al., "Effect of Carbon Monoxide Breathing on Hypoxia and Radiation Response in the SCCVII Tumor in vivo", *Int. J. Radiation Oncology Biol. Phys.* 29:449-454 (1994).

Hantson et al., "Organ Transplantation From Victims of Carbon Monoxide Poisoning," *Ann Emerg Med* 27(5):673-4 (1996).

Hebert et al., "Transplantation of Kidneys from a Donor with Carbon Monoxide Poisoning," New Engl J Med 326(23):1571 (1992).

Iberer et al., "Cardiac Allograft Harvesting after Carbon Monoxide Poisoning. Report of a Sucessful Orthotopic Heart Transplantation," *J Heart Lung Transplant* 12(3):499-500 (1993).

Katori et al., "Heme Oxygenase-1 System in Organ Transplantation", *Transplantation* 74(7):905-912 (2002).

Kaufman et al., "Differential Roles of Mac-1$^+$ Cells, and CD4$^+$ and CD8$^+$ T Lymphocytes in Primary Nonfunction and Classic Rejection of Islet Allografts," *J Exp Med*. 172:291-302(1990).

Koerner et al., "Extended Donor Criteria: Use of Cardiac Allografts after Carbon Monoxide Poisoning," *Transplantation* 63(9):1358-60 (1997).

Lacy et al., "Transplantation of Pancreatic Islets," *Ann. Rev. Immunol* 2:183-98 (1984).

Lee et al., "Regulation of Heme Oxygenase-1 Expression In Vivo and In Vitro in Hyperoxic Lung Injury", *Am. J. Respir. Cell Biol*. 14:556-568 (1996).

Lefer et al., "A Comparison of Vascular Biological Actions of Carbon Monoxide and Nitric Oxide", *Meth Find Exp Clin Pharmacol* 15(9):617-622 (1993).

Leikin et al., "The Toxic Patient as a Potential Organ Donor," *Am J Emerg Med* 12(2):151-4 (1994).

Mandrup-Poulsen et al., "Human Tumor Necrosis Factor Potentiates Human Interleukin 1-Mediated Rat Pancreatic β-Cell Cytotoxicity," *J. Immunol* 139:4077-82 (1987).

Mansouri et al., "Alteration of Platelet Aggregation by Cigarette Smoke and Carbon Monoxide," *Thromb Haemost* 48:286-8 (1982).

Maxwell et al., "Studies in Cancer Chemotherapy: XI. The Effect of CO, HCN, and Pituitrin Upon Tumor Growth", Dept. of Cancer Research , Santa Barbara Cottage Hospital, pp. 270-282 (Jan. 30, 1933).

The Merck Manual (16$^{th}$ Ed. 1992) pp. 646-657.

Minamino et al., "Targeted expression of heme oxygenase-1 prevents the pulmonary inflammatory and vascular responses to hypoxia", *PNAS* 98(15):8798-8803 (2001).

Myers, "Cirrhotic cardiomyopathy and liver transplantation," *Liver Transpl* 6(4 Suppl 1):S44-52 (2000).

Nagata et al.,"Destruction of Islet Isografts by Severe Nonspecific Inflammation," *Transplant Proc.* 22:855-6 (1990).

The New Encyclopedia Britannica (15$^{th}$ ed. 1994) vol. 26, *Macropaedia*, p. 756.

Otterbein et al., "Mechanism of hemoglobin-induced protection against endotoxemia in rats: a ferritin-independent pathway", *Am J Physiol Lung Cell Mol Physiol* 272:L268-275 (1997).

Otterbein et al., "Carbon monoxide has anti-inflammatory effects involving the mitogen-activated protein kinase pathway", *Nature Medicine* 6(4): 422-8 (2000).

Otterbein et al., "Carbon monoxide provides protection against hyperoxic lung injury", *The American Physiological Society* L688-L694 (1999).

Otterbein et al., "Carbon monoxide provides protection against hyperoxic lung injury in rats", *J Respiratory Critical Care Med* 159(3):A218 (1999).

Paredi et al., "Increased Carbon Monoxide in Exhaled Air of Cystic Fibrosis Patients", *J Respiratory Critical Care Med* 159(3):A218 (1999).

Petrache et al., "Heme oxygenase-1 inhibits TNF-α-induced apoptosis in cultured fibroblasts," *Am. J. Physiol. Lung Cell Mol. Physiol.* 287: L312-L319 (2000).

Piantadosi et al., "Production of Hydroxyl Radical in the Hippocampus After CO Hypoxia Hypoxia in the Rat", *Free Radical Biol. & Med.* 22(4):725-732 (1997).

Pozzoli et al., "Carbon Monoxide as a Novel Neuroendocrine Modulator: Inhibition of Stimulated Corticotropin-Releasing Hormone Release from Acute Rat Hypothalamic Explants," *Endocrinology* 135:2314-2317 (1994).

Rabinovitch et al., "Transfection of Human Pancreatic Islets With an Anti-Apoptotic Gene (*bcl-2*) Protects β-Cells From Cytokine-Induced Destruction," *Diabetes* 48:1223-9, 1999.

Ringel et al., "Carbon Monoxide-induced Parkinsonism", J. neurol. Sci. 16:245-251(1972).

Roberts et al., "Successful Heart Transplantation From a Victim of Carbon Monoxide Poisoning," *Ann Emerg Med* 26(5):652-5 (1995).

Sato et al., "Carbon Monoxide Generated by Heme Oxygenase-1 Suppresses the Rejection of Mouse-to-Rat Cardiac Transplants," *J. Immunol.* 166: 4185-4194 (2001).

Schipper et al., "Expression of Heme Oxygenase-1 in the Senescent and Alzheimer-diseased Brain", *Annals of Neurology* 37(6): 758-68 (1995).

Shapiro et al., "Islet Transplantation in Seven Patients with Type 1 Diabetes Mellitus Using a Glucocorticoid-Free Immunosuppressive Regimen," *N Engl. J. Med.*, 343:230-8, 2000.

Shennib et al., "Successful transplantation of a lung allograft from a carbon monoxide-poisoning victim," *Heart Lung Transplant* 11(1 Pt 1): 68-71 (1992).

Singhal et al., "Effects of Normobaric Hyperoxia in a Rat Model of Focal Cerebral Ischemia-Reperfusion", *J Cerebral Blood Flow & Medicine* 22:861-868 (2002).

Siow et al., "Heme oxygenase-carbon monoxide signalling pathway in atherosclerosis: anti-atherogenic actions of bilirubin and carbon monoxide?", *Cardiovascular Research* 41:385-394 (1999).

Smith et al., "Successful Heart Transplantation with Cardiac Allografts Exposed to Carbon Monoxide Poisoning," *Heart Lung Transplant* 11(4 Pt. 1):698-700 (1992).

Soares et al., "Expression of heme oxygenase-1 can determine cardiac xenograft survival," *Nat Med.* 4(9):1073-1077 (1998).

Stephens et al., "Further Observations Regarding Carbon Monoxide Gas as an Important Factor in the Causation of Industrial Cancer", *Medical Press and Circular* 183:283-288 (1933).

Taylor, "Anti-TNF Therapy for Rheumatoid Arthritis and Other Inflammatory Diseases", Molecular Biotechnology 19:153-168 (2001).

Tenderich et al., "Hemodynamic follow-up of cardiac allografts from poisoned donors," *Transplantation* 66(9):1163-7 (1998).

Tenhunen et al., "The Enzymatic Conversion of Heme to Bilirubin by Microsomal Heme Oxygenase," *Proc Natl Acad Sci USA* 61:748-755 (1968).

Tulis et al., "Adenovirus-Mediated Heme Oxygenase-1 Gene Delivery Inhibits Injury-Induced Vascular Neointima Formation", *Circulation* 104:2710-2715 (2001).

Utz et al., "Carbon Monoxide Relaxes Ileal Smooth Muscle Through Activation of Guanylate Cyclase," *Biochem Pharmacol.* 47:1195-201, 1991.

Vassalli et al., "Inhibition of Hypoxic Pulmonary Vasoconstriction By Carbon Monoxide in Dogs", European Respiratory Journal, ERS Annual Congress, Geneva, Switzerland, Sep. 19-23, 1998.

Verma et al., "Carbon Monoxide: A Putative Neural Messenger," *Science* 259:381-384, 1993.

Verran et al., "Use of Liver Allografts from Carbon Monoxide Poisoned Cadaveric Donors," *Transplantation* 62(10):1514-5 (1996).

Wang et al., "Resurgence of carbon monoxide: an endogenous gaseous vasorelaxing factor", *Can. J. Physiol. Pharmacol.* 76:1-15 (1998).

Weir et al., "Scientific and Political Impediments to Successful Islet Transplantation," *Diabetes* 46:1247-56, 1997.

Weir et al., "Islet transplantation as a treatment for diabetes," *J. Am. Optom. Assoc.* 69:727-32, 2000.

Welty et al., "Hyperoxic Lung Injury is Potentiated by SPC-Promotor Driven Expression of an HO-1 Transgene in Mice", *J Respiratory Critical Care Med* 159(3):A218 (1999).

Weng et al., "Transpulmonary HO-1 Gene Delivery in Neonatal Mice", *J Respiratory Critical Care Med* 159(3):A218 (1999).

Yuan et al., "Evidence of increased endogenous carbon monoxide production in newborn rat endotoxicosis," *Chinese Medical Sciences Journal* (1997), vol. 12, No. 4, 212-215.

PCT International Search Report (Mar. 23, 2004).

Baim and Grossman, "Treatment of Coronary Stenoses and Occlusions with Coronary Angioplasty," Harrison's Principles of Internal Medicine, 13th Ed., vol. 1, 193:986-87 (1994).

Choi, "HemeOxygenase-1 Protects the Heart," Circulation Research 89:105-107 (2001).

Clayton et al., "Inhaled carbon monoxide and hyperoxic lung injury in rats," Am. J. Physiol. Lung Cell Mol. Physiol. 281:L949-57 (2001).

Fujita et al., "Paradoxical rescue from ischemic lung injury by inhaled carbon monoxide driven by derepression of fibrinolysis," Nature Medicine 7:598-604 (2001).

Hayes, "A Review of Modern Concepts of Healing of Cutaneous Wounds," J. Dermatol. Surg. Oncol. 3(2):188-93 (1977).

Kyokane et al., "Carbon Monoxide From Heme Catabolism Protects Against Hepatobiliary Dysfunction in Endotoxin-Treated Rat Liver," Gastroenterology 120:1227-40 (2001).

Meilin et al., "Effects of carbon monoxide on the brain may be mediated by nitric oxide", J Appl Physiol. 81(3):1078-83 (1996).

Nachar at al., "Low-Dose Inhaled Carbon Monoxide Reduces Pulmonary Vascular Resistance During Acute Hypoxemia in Adult Sheep," High Altitude Medicine & Biology 2:377-385 (2001).

Otterbein and Choi, "Carbon monoxide at low concentrations causes growth arrest and modulates tumor growth in mice,"[Abstract], Am. J. Respir. Crit. Care Med. 163:A476 (2001).

Otterbein et al., "Carbon monoxide suppresses arteriosclerotic lesions associated with chronic graft rejection and with balloon injury," Nature Medicine 9:183-90 (2003).

Pannen et al., "Protective Role of Endogenous Carbon Monoxide in Hepatic Microcirculatory Dysfunction after Hemorrhagic Shock in Rats," J. Clin. Invest. 102:1220-1228 (1998).

Peek et al., "Extracorporeal Membrane Oxygenation for Adult Respiratory Failure," Chest 112(3)759-64 (1997).

Tamayo et al., "Carbon monoxide inhibits hypoxic pulmonary vasoconstriction in rats by a cGMP-independent mechanism", Pflugers Arch. 434(6):698-704 (1997).

Bartholomew, G.W. and M. Alexander, "Microbial metabolism of carbon monoxide in culture and in soil," *Appl. Environ. Microbiol.*, 37(5):932-937 (1979).

Bishop, G.A. et al., "Spontaneous acceptance of liver transplants in rodents: evidence that liver leucocytes induce recipient T-cell death by neglect," *Immunol. Cell Biol.*, 80(1):93-100 (2002).

Datta, R. and J.G. Zeikus, "Modulation of Acetone-Butanol-Ethanol Fermentation by Carbon Monoxide and Organic Acids," *Appl. Environ. Microbiol.*, 49(3):522-529 (1985).

Kanoria, S. et al., "A model to study total hepatic ischemia-reperfusion injury," *Transplant Proc.*, 36(9):2586-2589 (2004).

Medline Plus Medical Dictionary, definitions of organ, tissue and cell, accessed Oct. 9, 2007.

Allred et al., "Effects of Carbon Monoxide on Myocardial Ischemia," Environmental Health Perspectives 91:89-132 (1991).

American Thoracic Society, "Single breath carbon monoxide diffusing capacity (transfer factor): recommendations for a standard technique," Am. Rev. Respir. Dis. 136:1299-1307 (1987).

American Thoracic Society, "Single breath carbon monoxide diffusing capacity (transfer factor): recommendations for a standard technique-1995 update," Am. J. Respir. Crit. Care. Med. 152:2185-2198 (1995).

Arcasoy et al., "Erythropoietin (EPO) Stimulates Angiogenesis In Vivo and Promotes Wound Healing," Blood 98:822A-823A, Abstract (2001).

Caplan et al., "Role of asphyxia and feeding in a neonatal rat model of necrotizing enterocolitis," Pediatr. Pathol., 14:1017-1028 (1994).

Czlonkowska et al., "Immune processes in the pathogenesis of Parkinson's disease—a potential role for microglia and nitric oxide," Med. Sci. Monit. 8:RA165-RA177 (2002).

Goldberg and Schneider, "Similarities between the oxygen-sensing mechanisms regulating the expression of vascular endothelial growth factor and erythropoietin," J. Biol. Chem. 269:4355-359 (1994).

Guo, "The Research Status of the Gas Messenger Molecules of Nitric Oxide and Carbon Monoxide in the Biomedicine Field," Practical Journal of Cardiac, Cerebral and Pulmonary Vascular Diseases vol. 8(2) (2000) (English translation included).

Harmey and Bouchier-Hayes, "Vascular endothelial growth factor (VEGF), a survival factor for tumour cells: implications for antiangiogenic therapy," Bioessays 24:280-83(2003).

Josko, "Vascular endothelial growth factor (VEGF) and its effect on angiogenesis," Medical Science Monitor 6:1047-52 (2000).

Krause et al., "Recombinant human erythropoietin and VEGF have equal angiogenic potency: Investigation in a novel in vitro assay of human vascular tissues," European Heart J. 22:154 Abstract (2001).

Omaye, "Metabolic modulation of carbon monoxide toxicity," Toxicol. 180:139-150 (2002).

Potter et al., "The inflammation-induced pathological chaperones ACT and apo-E are necessary catalysts of Alzheimer amyloid formation," Neurobiology of Aging 22:923-30 (2001).

Shahin et al., "Carboxyhemoglobin in pediatric sepsis and the systematic inflammatory response syndrome," Clinical Intensive Care 11(6):311-17 (2000).

Stewart, "The effect of carbon monoxide on humans," J. Occup. Med. 18:304-309 (1976).

Stewart, "The effects of low concentrations of carbon monoxide in man," Scand. J. Respir. Dis. Suppl. 91:56-62 (1974).

Thiemermann, "Inhaled CO: Deadly gas or novel therapeutic," Nature Medicine 7(5): 534-35 (2001).

Vreman et al., "Carbon monoxide and carboxyhemoglobin," Adv. Pediatr. 42:303-34 (1995).

Wright and Shephard, "Physiological effects of carbon monoxide," Int. Rev. Physiol. 20:311-68 (1979).

Zegdi et al., "Increased endogenous carbon monoxide production in severe sepsis," Intensive Care Medicine 23:793-96 (2002).

Zuckerbraun et al., "Carbon Monoxide Protects against Liver Failure through Nitric Oxide-induced Heme Oxygenase 1," J. Exp. Med. 198:1707-716 (2003).

Zuckerbraun et al., "Carbon monoxide attenuates the development of necrotizing enterocolitis in an animal model," [Abstract #71], Surgical Infection Society, (2002), 3:83.

Zuckerbraun et al., "Carbon monoxide protects against liver failure through nitric oxide-induced heme oxygenase 1," The Journal of Experimental medicine, (2003), 198(11):1707-1716.

Bach, "Heme oxygenase-1 as a protective gene," Wiener Klinische Wochenschrift, Middle European Journal of Medicine 114:1-3 (2002).

Carbon Monoxide Poisoning — What Happens; http://my.webmd.com/hw/home_health/aa7326.asp;retrieved Jul. 11, 2005.

Carbon Monoxide Poisoning—Symptoms; http://my.webmd.com/hw/home_health/aa7304.asp;retrieved Jul. 11, 2005.

Coburn, "Biological Effects of Carbon Monoxide," Ann. N.Y. Acad. Sci. 174:343-368 (1970).

Libby and Poeber, "Chronic Rejection," Immunity 14:387-97 (2001).

Liu et al., "Carbon monoxide and nitric oxide suppress the hypoxic induction of vascular endothelial growth factor gene via the 5' enhancer," J. Biol. Chem. 273(24):15257-62 (1998).

Nakao et al., "Protective effect of carbon monoxide inhalation for cold-preserved small intestinal grafts," Surgery 134(2):285-292 (2003).

Sato et al., "Carbon monoxide can fully substitute Heme Oxygenase-1 in suppressing the rejection of mouse to rat cardiac transplants," Acta Haematologica, 103(Suppl. 1):87, Abstract 348 (2000).

Sato et al., "Heme oxygenase-1 or carbon monoxide prevents the inflammatory response associated with xenograft rejection," Acta Haematologica, 103(Suppl. 1):87, Abstract 345 (2000).

Suganuma et al., "A new process of cancer prevention mediated through inhibition of tumor necrosis factor alpha expression," Cancer Res. 56(16):3711-5 (1996).

Toda et al., "Exogenous carbon monoxide protects endothelial cells against oxidant stress and improves graft function after lung transplantation," Circulation, 98(17)I265 (1998).

Zhou et al., "Endogenous carbon monoxide and acute lung injury," Section of Respiratory System Foreign Medical Sciences 19:185-187 (1999) (translation included).

Choi et al., "Therapeutic' carbon monoxide may be a reality soon," Am. J. Respir. Crit. Care Med., 171(11):1318-1319 (2005).

Dolinay et al., "Can Inhalation Carbon Monoxide be utilized as a therapeutic modality in human diseases?", pp. 203-236 in *Breath Analysis for Clinical Diagnosis and Therapeutic Monitoring*, Amann and Smith, eds., World Scientific Publishing Company (2004).

Dolinay et al., "Inhaled carbon monoxide confers antiinflammatory effects against ventilator-induced lung injury," Am. J. Respir. Crit. Care Med. 170:613-20 (2004).

Mayr et al., "Effects of carbon monoxide inhalation during experimental endotoxemia in humans," Am. J. Respir. Crit. Care Med., 171:354-360 (2005).

Ryter et al., "Therapeutic applications of carbon monoxide in lung disease," Curr. Opin. Pharmacol., 6:257-262 (2006).

Ryter et al., "Heme oxygenase-1/carbon monoxide: from basic science to therapeutic applications," Physiol. Rev. 86(2):583-650 (2006).

Thom et al, "Therapeutic' Carbon Monoxide May Be Toxic," Am. J. Respir. Crit. Care Med., 171(11):1318 (2005).

Appel et al., The pig as a source of Cardiac xenografts,: J. Card. Surg. 16:345-56 (2001).

Billiar, "The diverging roles of carbon monoxide and nitric oxide in resuscitated hemorrhagic shock," Crit. Care Med. 27:2842-3 (1999).

Bracho et al., "Carbon Monoxide Protects against Organ Injury in Hemorrhagic Shock/Resuscitation," Journal of Surgical Research, 107:270, (2002), Abstract.

Brouard et al., "Carbon monoxide generated by Heme Oxygenase-1 (HO-1) suppresses endothelial cell apoptosis via activation of the p38 mitogen activated protein kinase (MAPK) pathway," Acta Haematologica 103(Suppl 1):64, (2000), Abstract.

Brouard et al., "Heme oxygenase-1-derived carbon monoxide requires the activation of transcription factor NF-kappa B to protect endothelial cells from tumor necrosis factor-alpha-mediated apoptosis," J. Biol. Chem., 277(20):17950-17961, (2002).

Brouard et al., "Molecular mechanism underlying the anti-apoptotic effect of Heme oxygenase-1 derived carbon monoxide," Xenotransplantation, 8(Suppl 1): p22 (2001).

Calabrese et al., "Carbon Monoxide (CO) Prevents Apoptotic Events Related to Ischemia/Reperfusion (IR) Injury in an hDAF Pig-to-Primate Xenotransplantation Model," Xenotransplantation 10:488, (2003), Abstract.

Chapman and Choi, "Exhaled monoxides as a pulmonary function test: use of exhaled nitric oxide and carbon monoxide," Clin. Chest Med. 22:817-836 (2001).

Chin et al., "Transcriptional regulation of the HO-1 gene in cultured macrophages exposed to model airborne particulate matter," Am. J. Physiol. Lung Cell. Mol. Physiol., 284(3):L473-L480, (2003).

Choi and Otterbein, "Emerging role of carbon monoxide in physiologic and pathophysiologic states," Antioxid. Redox Signal. 4:227-228 (2002).

Cozzi et al., "Donor Preconditioning with Carbon Monoxide (CO) in Pig-to-Primate Xenotransplantation," Xenotransplantation 10:528, (2003), Abstract.

Crapo et al., "Single-breath carbon monoxide diffusing capacity," Clin. Chest Med., 22:637-649, (2001).

Deng et al., "Carbon Monoxide Potentiates Cerulein-Induced Pancreatitis in Chronic Alcohol-Fed Rats," Gastroenterology, 124(4):A618-19, (2003), Abstract.

Dyck et al., "Carbon Monoxide (CO) Attenuates Lipopolysaccharide (LPS)-Induced Cytokine Expression of IL-6," Acta Haematologica 103(Suppl 1):64, (2000), Abstract.

Günther et al., "Carbon monoxide protects pancreatic beta-cells from apoptosis and improves islet function/survival after transplantation," Diabetes, 51(4):994-999, (2002).

Hartsfield and Choi, "Mitogen activated protein kinase (MAPK) is modulated by both endogenous and exogenous carbon monoxide," FASEB Journal 12:A187, 1088, (1998), Abstract.

Hartsfield et al., "Differential signaling pathways of HO-1 gene expression in pulmonary and systemic vascular cells," Am. J. Physiol., 277(6 Pt 1):L1133-L1141, (1999).

Hartsfield et al., "Regulation of heme oxygenase-1 gene expression in vascular smooth muscle cells by nitric oxide," Am. J. Physiol., 273(5 Pt 1):L980-988, (1997).

Hartsfield, "Targeted Overexpression of Heme Oxygenase-1 (HO-1) Attenuates Hypoxia-Induced Right Ventricular Hypertrophy," FASEB Journal 13:A827, (1999), Abstract.

Horvath et al., "'Haemoxygenase-1 induction and exhaled markers of oxidative stress in lung diseases', summary of the ERS Research Seminar in Budapest, Hungary, Sep. 1999," Eur. Respir. J., 18(2):420-430, (2001).

Kozma et al, "Role of carbon monoxide in heme-induced vasodilation," Eur. J. Pharmacol., 323:R1-2 (1997).

Moore et al., "Carbon Monoxide Protects against Intestinal Dysmotility Associated with Small Bowel Transplantation," Gastroenterology 122:A38, (2002), Abstract.

Moore et al., "Carbon Monoxide Suppresses the Development of Ileus Associated with Surgical Manipulation of the Small Intestine," Gastroenterology 122:A61-A62, (2002), Abstract.

Mori et al., "Evaluation of hypothermic heart preservation with University of Wisconsin solution in heterotopically and orthotopically transplanted canine hearts," J. Heart Lung Transplant. 13:688-950 (1994).

Morse et al., "Carbon monoxide-dependent signaling," Crit. Care Med., 30:S12-S17, (2001).

Morse et al., "Suppression of inflammatory cytokine production by carbon monoxide involves the JNK pathway and AP-1," J. Biol. Chem., 278(39):36993-36998, (2003).

Ning et al., "TGF-beta 1 stimulates HO-1 via the p38 mitogen-activated protein kinase in A549 pulmonary epithelial cells," Am. J. Physiol. Lung Cell. Mol. Physiol., 283(5):L1094-L1102, (2002).

Otterbein et al., "Carbon monoxide at low concentrations induces growth arrest and modulates tumor growth in mice," Exp. Biol. Med., 228(5):633, (2003), Abstract.

Otterbein et al., "Carbon Monoxide Inhibits TNFα-Induced Apoptosis and Cell Growth in Mouse Fibroblasts," American Journal of Respiratory and Critical Care Medicine 159(3 Suppl.):A285 (1999).

Otterbein et al., "Carbon Monoxide Modulates Lipolysaccharide (LPS)-Induced Inflammatory Responses in vivo and in vitro," American Journal of Respiratory and Critical Care Medicine 159(3 Suppl.):A481 (1999).

Otterbein et al., "Carbon Monoxide, A Gaseous Molecule with Anti-Inflammatory Properties," pp. 133-156 in *Disease Markers in Exhaled Breath*, Marczin et al., eds., Marcel Dekker, Inc., New York, (2003).

Otterbein et al., "Carbon Monoxide Mediates Anti-Inflammatory Effects Via the P38 Mitogen Activated Protein Kinase Pathway," Acta Haematologica 103: 64, (2000), Abstract.

Otterbein et al., "Carbon Monoxide Protects Against Oxidant-Induced Lung Injury in Mice Via the p38 Mitogen Activated Protein Kinase Pathway," Acta Haematologica 103:83, (2000), Abstract.

Otterbein et al., "Exogenous administration of heme oxygenase-1 by gene transfer provides protection against hyperoxia-induced lung injury," J. Clin. Invest., 103(7):1047-1054, (1999).

Otterbein et al., "Heme oxygenase: colors of defense against cellular stress," Am. J. Physiol. Lung Cell. Mol. Physiol., 279(6):L1029-L1037, (2000).

Otterbein et al., "Protective effects of heme oxygenase-1 in acute lung injury," Chest. 116:61S-63S, (1999).

Otterbein, "Anti-Inflammatory Effects of Carbon Monoxide in the Lung," CRISP Data Base National Institute of Health; Doc. No. CRISP/2003HL071797-01A1, (2003).

Otterbein, "Carbon monoxide: innovative anti-inflammatory properties of an age-old gas molecule," Antioxid. Redox Signal., 4:309-319, (2002).

Pileggi et al., "Heme oxygenase-1 induction in islet cells results in protection from apoptosis and improved in vivo function after transplantation," Diabetes, 50(9):1983-1991, (2001).

Ryter and Choi, "Heme Oxygenase-1: Molecular Mechanisms of Gene Expression in Oxygen-Related Stress," Antioxid. Redox Signal. 4:625-632, (2002).

Ryter et al., "Heme oxygenase/carbon monoxide signaling pathways: Regulation and functional significance," Mol. Cell. Biochem., 234-235(1-2):249-63, (2002).

Ryter et al., "Mitogen Activated Protein Kinase (MAPK) Pathway Regulates Heme Oxygenase-1 Gene Expression by Hypoxia in Vascular Cells," Exp. Biol. Med., 228(5):607, (2003), Abstract.

Sarady et al., "Carbon monoxide modulates endotoxin-induced production of granulocyte macrophage colony-stimulating factor in macrophages," Am. J. Respir. Cell. Mol. Biol., 27(6):739-745, (2002).

Sarady et al., "Cytoprotection by heme oxygenase/CO in the lung," in *Disease Markers in Exhaled Breath*, Marczin and Yacoub, eds., IOS Press, 346:73-78, (2002).

Sasidhar et al., "Exogenous Carbon Monoxide Attenuates Mitogen Activated Protein Kinase (MAPK) Activation in Rat Pulmonary Artery Endothelial Cells Exposed to Hypoxia," American Journal of Respiratory and Critical Care Medicine. 1999;159(3 Suppl.):A352.

Sass et al., "Heme Oxygenase-1 Induction Prevents Apoptotic Liver Damage in Mice," Naunyn-Schmiedeberg's Archives of Pharmacology 367:R78, (2003).

Sethi et al, "Differential modulation by exogenous carbon monoxide of TNF-alpha stimulated mitogen-activated protein kinases in rat pulmonary artery endothelial cells," Antioxid. Redox Signal., 4:241-8, (2002).

Sethi et al., "Differential Effects of Exogenous Carbon Monoxide on TNF-α-Induced Mitogen Activated Protein (MAP) Kinase Signaling Pathway in Rat Pulmonary Artery Endothelial Cells," American Journal of Respiratory and Critical Care Medicine 159(3 Suppl.):A350 (1999).

Seyfried et al., "HO-1 induction protects mice from Immune-mediated liver injury," Naunyn-Schmiedeberg's Archives of Pharmacology 367:R80 (2003).

Slebos et al., "Heme oxygenase-1 and carbon monoxide in pulmonary medicine," Respir Res. 4(7):1-13, (2003).

Soares et al, "Heme oxygenase-1, a protective gene that prevents the rejection of transplanted organs," Immunol. Rev. 184:275-85, (2001).

Soares et al, "Modulation of endothelial cell apoptosis by heme oxygenase-1-derived carbon monoxide," Antioxid. Redox Signal., 4:321-329, (2002).

Soares et al., "Heme Oxygenase-1 and/or Carbon Monoxide can Promote Organ Graft Survival," in *Disease Markers in Exhaled Breath*, Marczin and Yacoub, eds., IOS Press, 346:267-273, (2002).

Song et al., "Carbon monoxide induces cytoprotection in rat orthotopic lung transplantation via anti-inflammatory and anti-apoptotic effects," Am. J. Pathol., 163(1):231-242, (2003).

Song et al., "Carbon monoxide inhibits human airway smooth muscle cell proliferation via mitogen-activated protein kinase pathway," Am. J. Respir. Cell. Mol. Biol. 27(5):603-610, (2002).

Song et al., "Regulation of IL-1beta-induced GM-CSF production in human airway smooth muscle cells by carbon monoxide," Am. J. Physiol. Lung Cell. Mol. Physiol., 284(1):L50-L56, (2003).

Stupfel and Bouley, "Physiological and Biochemical Effects on Rats and Mice Exposed to Small Concentrations of Carbon Monoxide for Long Periods," Ann. N.Y. Acad. Sci. 174:343-368 (1970).

Tobiasch et al, "Heme oxygenase-1 protects pancreatic β cells from apoptosis caused by various stimuli," J. Investig. Med., 49:566-71, (2001).

Yamashita et al., "Effects of HO-1 induction and carbon monoxide on cardiac transplantation in mice," Exp. Biol. Med., 228(5):616, (2003), Abstract.

Zhang et al., "Carbon monoxide inhibition of apoptosis during ischemia-reperfusion lung injury is dependent on the p38 mitogen-activated protein kinase pathway and involves caspase 3," J. Biol. Chem., 278(2):1248-1258, (2003).

Zhang et al., "Mitogen-activated protein kinases regulate HO-1 gene transcription after ischemia-reperfusion lung injury," Am. J. Physiol. Lung Cell. Mol. Physiol., 283(4):L815-L829, (2002).

Zuckerbraun and Billiar, "Heme oxygenase-1: a cellular Hercules" Hepatology, 37(4):742-744, (2003).

Zuckerbraun et al., "Carbon monoxide inhibits intestinal inducible nitric oxide synthase production and ameliorates intestinal inflammation in experimental NEC," J. Amer. College of Surgeons 197:S50 (2003).

Zuckerbraun et al., "Carbon Monoxide Protects Hepatocytes from TNF-alpha/Actinomycin D Induced Cell Death," Critical Care Medicine 29:A59 (2001).

Bathoorn et al., "Effects of low dose inhaled carbon monoxide in patients with COPD," Eur. Respir. J., 28(Suppl. 50):661s (2006).

Carbon Monoxide to Prevent Lung Inflammation, http://www.clinicaltrials.gov/ct/show/NCT00094406?order=2 (website visited by applicant on Aug. 28, 2006).

Ellenhorn and Barceloux, "Carbon Monoxide" in *Medical Toxicology, Diagnosis and Treatment of Human Poisoning* (New York, New York) pp. 820-829 (1988).

Hartsfield, "Cross talk between carbon monoxide and nitric oxide," Antioxid. Redox Signal. 4:301-307 (2002).

Johnson et al., "Relationships between drug activity in NCI preclinical in vitro and in vivo models and early clinical trials," Br. J. Cancer 84:1424-31(2001).

Modification of Chronic Inflammation by Inhaled Carbon Monoxide in Patients with Stable Chronic Obstructive Pulmonary Disease (COPD). http://www.clinicaltrials.gov/ct/show/NCT00122694?order=I, website visited by Applicant on Aug. 28, 2006.

Morse and Choi, "Heme oxygenase-1: from bench to bedside," Am. J. Respir. Crit. Care Med. 172:660-670 (2005).

Motterlini et al., "Carbon Monoxide-Releasing Molecules: Characterization of Biochemical and Vascular Activities," Circ. Res. 90: e17-24 (2002).

Nakao et al., "A single intraperitoneal dose of carbon monoxide-saturated ringer's lactate solution ameliorates postoperative ileus in mice," J. Pharmacol. Exp. Ther. 319:1265-75 (2006).

Raman et al., "Inhaled carbon monoxide inhibits intimal hyperplasia and provides added benefit with nitric oxide," J. Vasc. Surg. 44:151-158 (2006).

Ramlawi et al., "Inhaled Carbon Monoxide Prevents Graft-Induced Intimal Hyperplasia in Swine," J. Surg. Res. 138:121-127 (2007).

Wang et al., "Carbon monoxide-induced vasorelaxation and the underlying mechanisms," Br. J. Pharmacol. 121:927-934 (1997).

Favory et al., "Myocardial Dysfunction and Potential Cardiac Hypoxia in Rats Induced by Carbon Monxide Inhalation," Am. J. Respir. Crit Care Med. 174:320-25 (2006).

Soares et al., "Heme oxygenase-1: from biology to therapeutic potential," Trends Mol. Med., 15:50-58 (2009).

Bauer et al., "Ileus in critical illness: mechanisms and management," Curr. Opin. Crit. Care, 8:152-157 (2002).

Bauer, A.J., "Mentation on the immunological modulation of gastrointestinal motility," Neurogastroenterol. Motil., 20(Suppl. 1):81-90 (2008).

DeWinter, B.Y., "Study of the pathogenesis of paralytic ileus in animal models of experimentally induced postoperative and septic ileus," Verh. K .Acad. Geneeskd. Belg., 293-324 (2003).

Hegazi et al., "Carbon monoxide ameliorates chronic murine colitis through a heme oxygenase 1-dependent pathway," J. Exp. Med., 202:1703-13 (2005).

Kalff et al., "Intra-abdominal activation of a local inflammatory response within the human muscularis externa during laparotomy," Ann. Surg., 237:301-315 (2003).

Wehner et al., "Inhibition of macrophage function prevents intestinal inflammation and postoperative ileus in rodents," Gut, 56:176-85 (2006).

Farrugia and Szurszewski, "Heme oxygenase, carbon monoxide, and interstitial cells of Cajal," Microsc. Res. Tech., 47(5):321-324, (1999).

Favory et al., "Myocardial dysfunction and potential cardiac hypoxia in rats induced by carbon monoxide inhalation," Am. J. Respir. Crit. Care Med., 174(3):320-325 (2006).

Huizinga, "Physiology and pathophysiology of the interstitial cell of Cajal: from bench to bedside: II. Gastric motility: lessons from mutant mice on slow waves and innervation," Am. J. Physiol. Gastrointest. Liver Physiol., 281(5):G1129-G1134, (2001).

Mazzola et al., "Carbon monoxide pretreatment prevents respiratory derangement and ameliorates hyperacute endotoxic shock in pigs," FASEB J., 19(14):2045-2047 (2005).

Miller et al., "Heme oxygenase 2 is present in interstitial cell networks of the mouse small intestine," Gastroenterology, 114(2):239-244, (1998).

Bathoorn et al., "Anti-inflammatory effects of inhaled carbon monoxide in patients with COPD: a pilot study," Eur. Respir. J. 0: 09031936.00163206v1 (Aug. 22, 2007).

* cited by examiner

METHODS OF TREATING ILEUS

CROSS-REFERENCE TO RELATED APPLICATIONS

This application claims priority to U.S. Provisional Application No. 60/372,652 filed Apr. 15, 2002, which is incorporated herein by reference in its entirety.

STATEMENT AS TO FEDERALLY SPONSORED RESEARCH

This invention was made with Government support under National Institutes of Health Grant Nos. HL55330, HL60234, GM58241 and GM53789 and AI42365. The Government has certain rights in this invention.

TECHNICAL FIELD

This invention relates to the treatment of gastrointestinal disorders.

BACKGROUND

Carbon monoxide (CO) gas is poisonous in high concentrations. However, it is now recognized as an important signaling molecule (Verma et al., Science 259:381-384, 1993). It has also been suggested that carbon monoxide acts as a neuronal messenger molecule in the brain (Id.) and as a neuroendocrine modulator in the hypothalamus (Pozzoli et al., Endocrinology 735:2314-2317, 1994). Like nitric oxide (NO), carbon monoxide is a smooth muscle relaxant (Utz et al., Biochem Pharmacol. 47:195-201, 1991; Christodoulides et al., Circulation 97:2306-9, 1995) and inhibits platelet aggregation (Mansouri et al, Thromb Haemost. 48:286-8, 1982). Inhalation of low levels of carbon monoxide has been shown to have anti-inflammatory effects in some models.

Ileus is a condition characterized by a lack of bowel motility, and is one of the more common forms of intestinal obstruction (see, e.g., Oxford Textbook of Surgery, Morris and Malt, Eds., Oxford University Press (1994)). Often, ileus occurs throughout the intestinal tract (e.g., both large and small bowel), but it can sometimes involve only one or several segments thereof. Intestinal manipulation during abdominal surgery frequently leads to ileus.

Various pharmaceutical approaches to treating ileus have been proposed (see, e.g., U.S. Pat. No. 5,362,756 (fedotozine); U.S. Pat. No. 5,929,035 (neuropeptides); U.S. Pat. No. 6,214,843 (pyrazolopyridine); and U.S. Pat. No. 5,958,407 (e.g., antagonizing proteinase-activated receptor-2)).

SUMMARY

The present invention is based, in part, on the discovery that administration of CO can attenuate ileus.

Accordingly, in one aspect, the invention features a method of treating ileus in a patient, which includes identifying a patient suffering from or at risk for ileus and administering to the patient a pharmaceutical composition comprising an effective amount or concentration of carbon monoxide.

The ileus can be ileus of any portion of the gastrointestinal tract, e.g., the stomach, small intestine and/or the colon. The ileus can result from any factor that causes ileus, e.g., surgery, e.g., abdominal surgery such as transplantation surgery (e.g., small intestinal transplantation (SITx)) or abdominal surgery other than transplantation surgery (e.g., abdominal surgery involving laparotomy or not involving laparotomy, e.g., laproscopic procedures); orthopedic surgeries (e.g., hip surgery); parturition; intestinal ischaemia; retroperitoneal haematoma; intraabdominal sepsis; intraperitoneal inflammation, e.g., acute appendicitis, choecystitis, pancreatitis; fractures of the spine; ureteric colic; thoracic lesions; basal pneumonia; rib fractures; myocardial infarction; metabolic disturbances; or any combination thereof.

The pharmaceutical composition can be administered to the patient by any method known in the art for administering gases, liquids, and/or solids to patients, e.g., via inhalation, insufflation, infusion, injection, and/or ingestion. For example, in one embodiment of the present invention, the pharmaceutical composition is administered to the patient by inhalation. In another embodiment, the pharmaceutical composition is administered to the patient orally. In yet another embodiment, the pharmaceutical composition is administered directly to the abdominal cavity of the patient.

The method can further include administering to the patient at least one of the following treatments in addition to CO: inducing HO-1 or ferritin in the patient; expressing recombinant HO-1 or ferritin in the patient; and administering a pharmaceutical composition comprising HO-1, bilirubin, biliverdin, ferritin, desferoxamine, iron dextran, or apoferritin to the patient.

In another aspect, the invention features a method of treating post-surgical ileus in a patient. The method includes identifying a patient suffering from post-surgical ileus and administering to the patient a pharmaceutical composition comprising an amount of carbon monoxide effective to treat ileus in the patient. The ileus can be ileus of any part of the gastrointestinal tract, e.g., the stomach, small intestine, and/or large intestine (e.g., the colon). The pharmaceutical composition can be administered to the patient via any route described herein, e.g., via inhalation (of gaseous compositions); orally; and/or by direct administration to the abdominal cavity of the patient.

The invention also features a method of treating ileus in a patient suffering from or at risk for ileus not caused by abdominal surgery, e.g., ileus caused by any factor described herein other than abdominal surgery. The method includes identifying a patient suffering from or at risk for ileus not caused by abdominal surgery and administering to the patient a pharmaceutical composition comprising an amount of carbon monoxide effective to treat ileus in the patient.

In another aspect, the invention features a method of treating ileus in a patient, which includes the steps of providing a vessel containing a pressurized gas comprising carbon monoxide gas, identifying a patient suffering from or at risk for ileus, releasing the pressurized gas from the vessel to form an atmosphere that includes carbon monoxide gas, and exposing the patient to the atmosphere, wherein the amount of carbon monoxide in the atmosphere is sufficient to treat ileus in the patient.

In yet another aspect, the invention provides a method of performing surgery on a patient. The method includes identifying a patient in need of surgery, and before, during, and/or after the surgery, causing the patient to inhale an amount of carbon monoxide gas sufficient to treat ileus in the patient.

The surgery can be any surgery that causes and/or puts the patient at risk for ileus. For example, the surgery can involve manipulation (e.g., touching (directly or indirectly)) of the gastrointestinal tract, e.g., the stomach and/or intestines, e.g., small or large intestine (e.g., the colon), and can be a surgery involving laparotomy or not involving laparotomy (e.g., surgeries involving laparoscopy). In certain embodiments, the surgery can be transplant surgery or non-transplant surgery, e.g., surgery involving any organ(s) or tissue(s) in the abdomen, e.g., surgery of the urogenital system (e.g., kidneys, ureter, and/or bladder; and reproductive organs (e.g., uterus, ovaries, and/or fallopian tubes)); the digestive system (e.g., the stomach, small intestine, large intestine (e.g., the colon), appendix, gallbladder, liver, spleen, and/or pancreas); the lymphatic system; the respiratory system (e.g., the lungs); the diaphram; surgery to treat cancer of any organ or tissue within the abdomen; endometrial surgery; and orthopedic surgeries, e.g., hip surgery.

In another aspect, the invention provides a vessel comprising medical grade compressed CO gas. The vessel can bear a label indicating that the gas can be used to treat ileus, e.g., ileus resulting from surgery (e.g., surgery involving intestinal manipulation), in a patient (e.g., a human patient). The CO gas can be in an admixture with nitrogen gas, with nitric oxide and nitrogen gas, or with an oxygen-containing gas. The CO gas can be present in the admixture at a concentration of at least about 0.025%, e.g., at least about 0.05%, 0.10%, 0.50%, 1.0%, 2.0%, 10%, 50%, or 90%.

In still another aspect, the invention provides a method of treating ileus in a patient, which includes identifying a patient suffering from or at risk for ileus and administering to the patient at least one of the following treatments in conjunction with treatment with CO: inducing HO-1 or ferritin in the patient; expressing recombinant HO-1 or ferritin in the patient; and administering a pharmaceutical composition comprising HO-1, bilirubin, biliverdin, ferritin, or apoferritin to the patient. Also contemplated is use of CO and any of the above-listed agents in the preparation of a medicament for treatment or prevention of ileus.

Also within the invention is the use of CO in the manufacture of a medicament for treatment or prevention of a condition described herein, e.g., ileus. The medicament can also be used in a method for treating ileus in a patient and/or for treating donors, organs, and/or recipients in transplantation procedures. The medicament can be in any form described herein, e.g., a liquid or gaseous CO composition.

Unless otherwise defined, all technical and scientific terms used herein have the same meaning as commonly understood by one of ordinary skill in the art to which this invention belongs. Suitable methods and materials are described below, although methods and materials similar or equivalent to those described herein can be used in the practice or testing of the present invention. All publications, patent applications, patents, and other references mentioned herein are incorporated by reference in their entirety. In case of conflict, the present specification, including definitions, will control. The materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
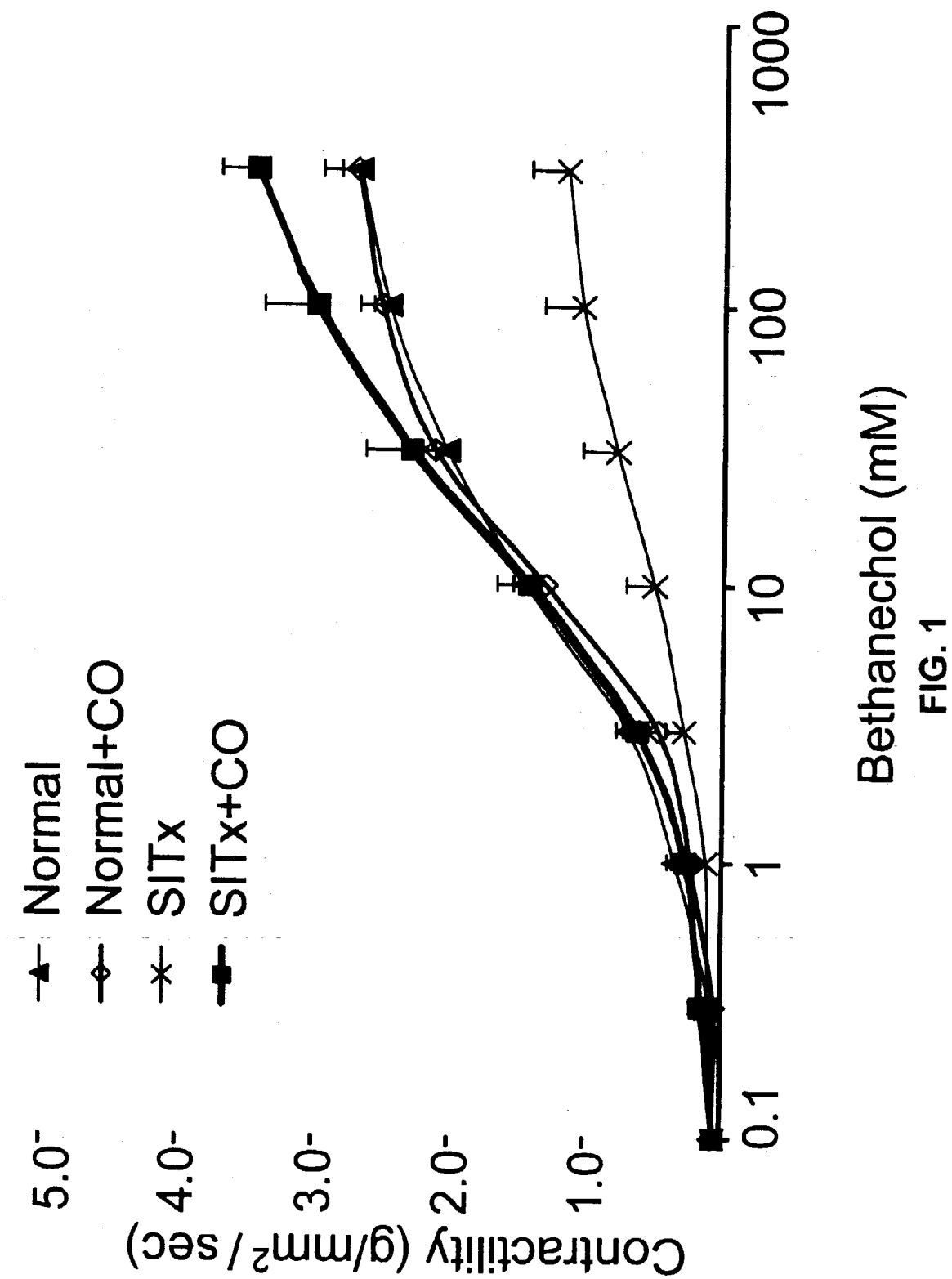
FIG. 1 is a line graph that illustrates the effect of small intestine transplantation (SITx) and treatment with CO on spontaneous and bethanechol-stimulated small intestinal circular muscle contractility. ▲=control; ◇=control+CO; X=SITx; ■=SITx+CO.

The term "carbon monoxide" (or "CO") as used herein describes molecular carbon monoxide in its gaseous state, compressed into liquid form, or dissolved in aqueous solution. The term "carbon monoxide composition" or "pharmaceutical composition comprising carbon monoxide" is used throughout the specification to describe a gaseous or liquid composition containing carbon monoxide that can be administered to a patient and/or an organ, e.g., a small intestine. The skilled practitioner will recognize which form of the pharmaceutical composition, e.g., gaseous, liquid, or both gaseous and liquid forms, is preferred for a given application.

The terms "effective amount" and "effective to treat," as used herein, refer to the administration of carbon monoxide in an amount or concentration and for period of time including acute or chronic administration and periodic or continuous administration that is effective within the context of its administration for causing an intended effect or physiological outcome. Effective amounts of CO for use in the present invention include, for example, amounts that prevent or reduce ileus following a procedure, e.g., small intestinal transplant.

For gases, effective amounts of CO generally fall within the range of about 0.0000001% to about 0.3% by weight, e.g., 0.0001% to about 0.25% by weight, preferably at least about 0.001%, e.g., at least about 0.005%, 0.010%, 0.02%, 0.025%, 0.03%, 0.04%, 0.05%, 0.06%, 0.08%, 0.10%, 0.15%, 0.20%, 0.22%, or 0.24% by weight CO. For liquid solutions of CO, effective amounts generally fall within the range of about 0.0001 to about 0.0044 g CO/100 g liquid, e.g., at least about 0.0001, 0.0002, 0.0004, 0.0006, 0.0008, 0.0010, 0.0013, 0.0014, 0.0015, 0.0016, 0.0018, 0.0020, 0.0021, 0.0022, 0.0024, 0.0026, 0.0028, 0.0030, 0.0032, 0.0035, 0.0037, 0.0040, or 0.0042 g CO/100 g aqueous solution. Preferred ranges include, e.g., about 0.0010 to about 0.0030 g CO/100 g liquid, about 0.0015 to about 0.0026 g CO/100 g liquid, or about 0.0018 to about 0.0024 g CO/100 g liquid. A skilled practitioner will appreciate that amounts outside of these ranges may be used depending upon the application.

The terms "patient" is used throughout the specification to describe an animal, human or non-human, to whom treatment according to the methods of the present invention is provided. Veterinary applications are clearly anticipated by the present invention. The term includes but is not limited to mammals, e.g., humans, other primates, pigs, rodents such as mice and rats, rabbits, guinea pigs, hamsters, cows, horses, cats, dogs, sheep and goats. The term "treat(ment)," is used herein to describe delaying the onset of, inhibiting, preventing, or alleviating the effects of a condition, e.g., ileus. The term "donor" or "donor patient" as used herein refers to an patient (human or non-human) from whom an organ or tissue can be obtained for the purposes of transplantation to a recipient patient. The term "recipient" or "recipient patient" refers to a patient (human or non-human) into which an organ or tissue can be transferred.

The term "ileus" as used herein generally refers to partial or complete paralysis or dysmotility of the gastrointestinal tract. Ileus can occur throughout the gastrointestinal tract, or can involve only one or several sections thereof, e.g., stomach, small intestine, or colon. The skilled practitioner will appreciate that ileus can be caused by a great number of factors that include, for example, surgery (e.g., any surgery involving laparotomy, e.g., small intestinal transplantation (SITx); or any surgery involving laparoscopy); intestinal ischaemia; retroperitoneal haematoma; intraabdominal sepsis; intraperitoneal inflammation; acute appendicitis; choecystitis; pancreatitis; ureteric colic; thoracic lesions; basal pneumonia; myocardial infarction; metabolic disturbances, e.g., those that result in decreased potassium levels; drugs, e.g., prolonged use of opiates; and traumas, e.g., fractures of the spine and rib fractures (see, e.g., Oxford Textbook of Surgery, Morris and Malt, Eds., Oxford University Press (1994)). The term also includes post-partum ileus, which is a common problem for women in the period following parturition, e.g., following vaginal delivery ("natural childbirth") or surgically-assisted parturition. As used herein, the term "post-surgical ileus" refers to ileus experienced by a patient following any surgical procedure, e.g., abdominal surgery. The term "non-surgical interventions" refers to medical treatments not involving surgery. The term "ileus resulting from conditions not involving surgery" refers to ileus caused by factors other than surgery, e.g., factors described herein.

Individuals considered at risk for developing ileus may benefit particularly from the invention, primarily because prophylactic treatment can begin before there is any evidence of ileus. Individuals "at risk" include, e.g., patients in need of abdominal surgery, whether medically necessary or elective, and/or individuals suffering from any of the conditions or injuries described in the preceding paragraph. The skilled practitioner will appreciate that a patient can be determined to be at risk for ileus by any method known in the art, e.g., by a physician's diagnosis.

The term "transplantation" is used throughout the specification as a general term to describe the process of transferring an organ or tissue (e.g., a small intestine) into a patient. The term "transplantation" is defined in the art as the transfer of living tissues or cells from a donor to a recipient, with the intention of maintaining the functional integrity of the transplanted tissue or cells in the recipient (see, e.g., *The Merck Manual*, Berkow, Fletcher, and Beers, Eds., Merck Research Laboratories, Rahway, N.J., 1992). The term includes all categories of transplants known in the art. Transplants are categorized by site and genetic relationship between donor and recipient. The term includes, e.g., autotransplantation (removal and transfer of cells or tissue from one location on a patient to the same or another location on the same patient), allotransplantation (transplantation between members of the same species), and xenotransplantation (transplantations between members of different species).

Preparation of Gaseous Compositions

A CO composition may be a gaseous carbon monoxide composition. Compressed or pressurized gas useful in the methods of the invention can be obtained from any commercial source, and in any type of vessel appropriate for storing compressed gas. For example, compressed or pressurized gases can be obtained from any source that supplies compressed gases, such as oxygen, for medical use. The term "medical grade" gas, as used herein, refers to gas suitable for administration to patients as defined herein. The pressurized gas including carbon monoxide used in the methods of the present invention can be provided such that all gases of the desired final composition (e.g., CO, He, NO, $CO_2$, $O_2$, $N_2$) are in the same vessel, except that NO and $O_2$ cannot be stored together. Optionally, the methods of the present invention can be performed using multiple vessels containing individual gases. For example, a single vessel can be provided that contains carbon monoxide, with or without other gases, the contents of which can be optionally mixed with room air or with the contents of other vessels, e.g., vessels containing oxygen, nitrogen, carbon dioxide, compressed air, or any other suitable gas or mixtures thereof.

Gaseous compositions administered to a patient according to the present invention typically contain 0% to about 79% by weight nitrogen, about 21% to about 100% by weight oxygen and about 0.0000001% to about 0.3% by weight (corresponding to about 1 ppb or 0.001 ppm to about 3,000 ppm) carbon monoxide. Preferably, the amount of nitrogen in the gaseous composition is about 79% by weight, the amount of oxygen is about 21% by weight, and the amount of carbon monoxide is about 0.0001% to about 0.25% by weight. The amount of CO is preferably at least about 0.001%, e.g., at least about 0.005%, 0.010%, 0.02%, 0.025%, 0.03%, 0.04%, 0.05%, 0.06%, 0.08%, 0.10%, 0.15%, 0.20%, 0.22%, or 0.24% by weight. Preferred ranges include about 0.005% to about 0.24%, about 0.01% to about 0.22%, about 0.015% to about 0.20%, about 0.08% to about 0.20%, and about 0.025% to about 0.1% by weight. It is noted that gaseous carbon monoxide compositions having concentrations of carbon monoxide greater than 0.3% (such as 1% or greater) may be used for short periods (e.g., one or a few breaths), depending upon the application.

A gaseous carbon monoxide composition may be used to create an atmosphere that comprises carbon monoxide gas. An atmosphere that includes appropriate levels of carbon monoxide gas can be created, for example, by providing a vessel containing a pressurized gas comprising carbon monoxide gas, and releasing the pressurized gas from the vessel into a chamber or space to form an atmosphere that includes the carbon monoxide gas inside the chamber or space. Alternatively, the gases can be released into an apparatus that culminates in a breathing mask or breathing tube, thereby creating an atmosphere comprising carbon monoxide gas in the breathing mask or breathing tube, ensuring the patient is the only person in the room exposed to significant levels of carbon monoxide.

Carbon monoxide levels in an atmosphere can be measured or monitored using any method known in the art. Such methods include electrochemical detection, gas chromatography, radioisotope counting, infrared absorption, colorimetry, and electrochemical methods based on selective membranes (see, e.g., Sunderman et al., Clin. Chem. 28:2026-2032, 1982; Ingi et al., Neuron 16:835-842, 1996). Sub-parts per million carbon monoxide levels can be detected by, e.g., gas chromatography and radioisotope counting. Further, it is known in the art that carbon monoxide levels in the sub-ppm range can be measured in biological tissue by a midinfrared gas sensor (see, e.g., Morimoto et al., Am. J. Physiol. Heart. Circ. Physiol 280:H482-H488, 2001). Carbon monoxide sensors and gas detection devices are widely available from many commercial sources.

Preparation of Liquid Compositions

A carbon monoxide composition may also be a liquid carbon monoxide composition. A liquid can be made into a carbon monoxide composition by any method known in the art for causing gases to become dissolved in liquids. For example, the liquid can be placed in a so-called "$CO_2$ incubator" and exposed to a continuous flow of carbon monoxide, preferably balanced with carbon dioxide, until a desired concentration of carbon monoxide is reached in the liquid. As another example, carbon monoxide gas can be "bubbled" directly into the liquid until the desired concentration of carbon monoxide in the liquid is reached. The amount of carbon monoxide that can be dissolved in a given aqueous solution increases with decreasing temperature. As still another example, an appropriate liquid may be passed through tubing that allows gas diffusion, where the tubing runs through an atmosphere comprising carbon monoxide (e.g., utilizing a device such as an extracorporeal membrane oxygenator). The carbon monoxide diffuses into the liquid to create a liquid carbon monoxide composition.

It is likely that such a liquid composition intended to be introduced into a living animal will be at or about 37° C. at the time it is introduced into the animal.

The liquid can be any liquid known to those of skill in the art to be suitable for administration to patients, or preserving and/or washing and/or perfusing organs of interest (see, for example, Oxford Textbook of Surgery, Morris and Malt, Eds., Oxford University Press (1994)). In general, the liquid will be an aqueous solution. Examples of appropriate solutions include Phosphate Buffered Saline (PBS), Celsior™, Perfadex™, Collins solution, citrate solution, and University of Wisconsin (UW) solution (Oxford Textbook of Surgery, Morris and Malt, Eds., Oxford University Press (1994)). In one embodiment of the present invention, the liquid is Ringer's Solution, e.g., lactated Ringer's Solution, or any other liquid that can be used infused into a patient. In another embodiment, the liquid includes blood, e.g., whole blood.

Any suitable liquid can be saturated to a set concentration of carbon monoxide via gas diffusers. Alternatively, premade solutions that have been quality controlled to contain set levels of carbon monoxide can be used. Accurate control of dose can be achieved via measurements with a gas permeable, liquid impermeable membrane connected to a carbon monoxide analyzer. Solutions can be saturated to desired effective concentrations and maintained at these levels.

Treatment of Patients with Carbon Monoxide Compositions

A patient can be treated with a carbon monoxide composition by any method known in the art of administering gases and/or liquids to patient. Carbon monoxide compositions can be administered to a patient diagnosed with, or determined to be at risk for ileus, e.g., surgical patients, including patients who undergo SITx. The invention contemplates the systemic administration of liquid or gaseous carbon monoxide compositions to patients (e.g., by inhalation and/or ingestion), and the topical administration of the compositions to the patient's gastrointestinal tract (e.g., by ingestion, insufflation, and/or introduction into the abdominal cavity).

Systemic Delivery of Carbon Monoxide

Gaseous carbon monoxide compositions can be delivered systemically to a patient, e.g., a surgical patient or small bowel transplant donor and/or recipients. Gaseous carbon monoxide compositions are typically administered by inhalation through the mouth or nasal passages to the lungs, where the carbon monoxide may exert its effect directly or be readily absorbed into the patient's bloodstream. The concentration of active compound (CO) utilized in the therapeutic gaseous composition will depend on absorption, distribution, inactivation, and excretion (generally, through respiration) rates of the carbon monoxide as well as other factors known to those of skill in the art. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. Acute, sub-acute and chronic administration of carbon monoxide are contemplated by the present invention, depending upon, e.g., the severity or persistence of ileus in the patient. Carbon monoxide can be delivered to the patient for a time (including indefinitely) sufficient to treat the condition and exert the intended pharmacological or biological effect.

The following are examples of some methods and devices that can be utilized to administer gaseous carbon monoxide compositions to patients.

Ventilators

Medical grade carbon monoxide (concentrations can vary) can be purchased mixed with air or another oxygen-containing gas in a standard tank of compressed gas (e.g., 21% $O_2$, 79% $N_2$). It is non-reactive, and the concentrations that are required for the methods of the present invention are well below the combustible range (10% in air). In a hospital setting, the gas presumably will be delivered to the bedside where it will be mixed with oxygen or house air in a blender to a desired concentration in ppm (parts per million). The patient will inhale the gas mixture through a ventilator, which will be set to a flow rate based on patient comfort and needs. This is determined by pulmonary graphics (i.e., respiratory rate, tidal volumes etc.). Fail-safe mechanism(s) to prevent the patient from unnecessarily receiving greater than desired amounts of carbon monoxide can be designed into the delivery system. The patient's carbon monoxide level can be monitored by studying (1) carboxyhemoglobin (COHb), which can be measured in venous blood, and (2) exhaled carbon monoxide collected from a side port of the ventilator. Carbon monoxide exposure can be adjusted based upon the patient's health status and on the basis of the markers. If necessary, carbon monoxide can be washed out of the patient by switching to 100% $O_2$ inhalation. Carbon monoxide is not metabolized; thus, whatever is inhaled will ultimately be exhaled except for a very small percentage that is converted to $CO_2$. Carbon monoxide can also be mixed with any level of $O_2$ to provide therapeutic delivery of carbon monoxide without consequential hypoxic conditions.

Face Mask and Tent

A carbon monoxide-containing gas mixture is prepared as above to allow passive inhalation by the patient using a facemask or tent. The concentration inhaled can be changed and can be washed out by simply switching over to 100% $O_2$. Monitoring of carbon monoxide levels would occur at or near the mask or tent with a fail-safe mechanism that would prevent too high of a concentration of carbon monoxide from being inhaled.

Portable Inhaler

Compressed carbon monoxide can be packaged into a portable inhaler device and inhaled in a metered dose, for example, to permit intermittent treatment of a recipient who is not in a hospital setting. Different concentrations of carbon monoxide could be packaged in the containers. The device could be as simple as a small tank (e.g., under 5 kg) of appropriately diluted CO with an on-off valve and a tube from which the patient takes a whiff of CO according to a standard regimen or as needed.

Intravenous Artificial Lung

An artificial lung (a catheter device for gas exchange in the blood) designed for $O_2$ delivery and $CO_2$ removal can be used for carbon monoxide delivery. The catheter, when implanted, resides in one of the large veins and would be able to deliver carbon monoxide at given concentrations either for systemic delivery or at a local site. The delivery can be a local delivery of a high concentration of carbon monoxide for a short period of time at the site of the procedure, e.g., in proximity to the small intestine (this high concentration would rapidly be diluted out in the bloodstream), or a relatively longer exposure to a lower concentration of carbon monoxide (see, e.g., Hattler et al., Artif. Organs 18(11):806-812 (1994); and Golob et al., ASAIO J., 47(5):432-437 (2001)).

Normobaric Chamber

In certain instances, it would be desirable to expose the whole patient to carbon monoxide. The patient would be inside an airtight chamber that would be flooded with carbon monoxide (at a level that does not endanger the patient, or at a level that poses an acceptable risk without the risk of bystanders being exposed. Upon completion of the exposure, the chamber could be flushed with air (e.g., 21% $O_2$, 79% $N_2$) and samples could be analyzed by carbon monoxide analyzers to ensure no carbon monoxide remains before allowing the patient to exit the exposure system.

Systemic Delivery of Liquid CO Compositions

The present invention further contemplates that liquid CO compositions can be created for systemic delivery to a patient, e.g., by infusion into a patient. For example, liquid CO compositions, such as CO-saturated Ringer's Solution, can be infused into a patient before, during, and/or after a surgical procedure. Alternatively or in addition, CO-partially or completely saturated whole (or partial) blood can be infused into the patient. The present invention also contemplates that agents capable of delivering doses of CO gas or liquid can be utilized (e.g., CO releasing gums, creams, ointments or patches).

Topical Treatment of the Gastrointestinal Tract with Carbon Monoxide

Alternatively or in addition, carbon monoxide compositions can be applied directly to the gastrointestinal tract, e.g., to the interior and/or exterior of the entire gastrointestinal tract, or to any portion thereof. A gaseous composition can be directly applied to the gastrointestinal tract of a patient, e.g., a surgical patient or small bowel transplantation donor or recipient, by any method known in the art for insufflating gases into a patient. For example, gases, e.g., carbon dioxide, are often insufflated into the gastrointestinal tract and the abdominal cavity of patients to facilitate examination during endoscopic and laproscopic procedures, respectively (see, e.g., Oxford Textbook of Surgery, Morris and Malt, Eds., Oxford University Press (1994)). The skilled practitioner will appreciate that similar procedures could be used to administer carbon monoxide compositions directly to the gastrointestinal tract of a patient. It is contemplated that the present invention can be applied to help prevent ileus resulting from laproscopy and endoscopy, e.g., colonoscopy and oesophagogastroduodenoscopy.

Aqueous carbon monoxide compositions can also be administered topically to the gastrointestinal tract of a patient. Aqueous forms of the compositions can be administered by any method known in the art for administering liquids to patients. As with gaseous compositions, aqueous compositions can be applied directly to the interior and/or exterior of the gastrointestinal tract. For example, the aqueous form can be administered orally, e.g., by causing the patient to ingest an encapsulated or unencapsulated dose of the aqueous carbon monoxide composition. As another example, liquids, e.g., saline solutions containing dissolved CO, can be injected into the gastrointestinal tract and the abdominal cavity of patients during endoscopic and laproscopic procedures, respectively. In the context of SITx, in situ exposures can be performed by any method known in the art, e.g., by in situ flushing of the organ with a liquid carbon monoxide composition prior to removal from the donor (see Oxford Textbook of Surgery, Morris and Malt, Eds., Oxford University Press (1994)).

Small Intestinal Transplantation Organ Preservation ex vivo

Carbon monoxide compositions can be used to treat patients who undergo transplantation of any portion of the gastrointestinal tract, e.g., small intestinal transplantation (SITx). In the context of transplantation procedures, carbon monoxide compositions can be used to treat donors, recipients and/or the organ itself at any step of the organ harvesting, storage, and transplant process. A gastrointestinal organ may be harvested from a donor, treated with a carbon monoxide composition ex vivo in accordance with the present invention, and transplanted into a recipient. Alternatively or in addition, the organ can be treated in situ, while still in the donor. Optionally, a carbon monoxide composition can be administered to the recipient prior to, during, and/or after the surgery: e.g., after the organ is reperfused with the recipient's blood. The carbon monoxide composition may be administered to the donor prior to or during the process of harvesting the organ from the donor.

Ex vivo exposure of the small intestine (or portion thereof) to carbon monoxide can occur by exposing the small intestine to an atmosphere comprising carbon monoxide gas, to a liquid carbon monoxide composition, e.g., a liquid perfusate, storage solution, or wash solution having carbon monoxide dissolved therein, or to both.

Exposure of the small intestine to gaseous carbon monoxide compositions can be performed in any chamber or area suitable for creating an atmosphere that includes appropriate levels of carbon monoxide gas. Such chambers include, for example, incubators and chambers built for the purpose of accommodating an organ in a preservation solution. An appropriate chamber may be a chamber wherein only the gases fed into the chamber are present in the internal atmosphere, such that the concentration of carbon monoxide can be established and maintained at a given concentration and purity, e.g., where the chamber is airtight. For example, a $CO_2$ incubator may be used to expose an organ to a carbon monoxide composition, wherein carbon monoxide gas is supplied in a continuous flow from a vessel that contains the gas.

Exposure of an organ to a liquid carbon monoxide composition can be performed ex vivo by any method known in the art. For example, the exposure may be performed ex vivo in any chamber or space having sufficient volume for submerging the organ, completely or partially, in the carbon monoxide composition. As another example, the organ may be exposed to a carbon monoxide composition by placing the organ in any suitable container and causing the carbon monoxide composition to "wash over" the organ, such that the organ is exposed to a continuous flow of the carbon monoxide composition.

As another example, the organ may be perfused with a carbon monoxide composition. The term "perfusion" is an art recognized term, and relates to the passage of a liquid, e.g., a carbon monoxide composition, through the blood vessels of the organ. With regard to the gastrointestinal tract, the term includes flushing the intestinal lumen with a carbon monoxide composition. Methods for perfusing organs ex vivo and in situ are well known in the art. An organ can be perfused with a carbon monoxide composition ex vivo, for example, by continuous hypothermic machine perfusion (see Oxford Textbook of Surgery, Morris and Malt, Eds., Oxford University Press (1994)). Optionally, in in situ or ex vivo perfusions, the organ can be perfused with a wash solution, e.g., UW solution without carbon monoxide, prior to perfusion with the carbon monoxide composition, to remove the donor's blood from the organ. Such a process could be performed to avoid competition for carbon monoxide by the donor's hemoglobin. As another option, the wash solution can be a carbon monoxide composition.

As yet another example, the organ may be placed, e.g., submerged, in a medium or solution that does not include carbon monoxide, and placed in a chamber such that the medium or solution can be made into a carbon monoxide composition via exposure to a carbon monoxide-containing atmosphere as described herein. As still another example, the organ may be submerged in a liquid that does not include carbon monoxide, and carbon monoxide may is then "bubbled" into the liquid.

A small intestine can be harvested from a donor and transplanted by any methods known to those of skill in the art (see, for example, Oxford Textbook of Surgery, Morris and Malt, Eds., Oxford University Press (1994)). The skilled practitioner will recognize that methods for transplanting and/or harvesting organs for transplantation may vary depending upon many circumstances, such as the age of the donor/recipient.

The present invention contemplates that any or all of the above methods for exposing an organ to a liquid carbon monoxide composition, e.g., washing, submerging, or perfusing, can be used in a given procedure, e.g., used in a single SITx procedure.

Use of Hemoxygenase-1 and Other Compounds

Also contemplated by the present invention is the induction or expression of hemeoxygenase-1 (HO-1) in conjunction with administration of carbon monoxide. In the context of SITx, HO-1 may optionally be induced in the organ, the organ donor, the recipient, or all three, in conjunction with the administration of carbon monoxide. For example, HO-1 can be induced in the donor, e.g., prior to or during removal of the organ, in the organ ex vivo, and/or in the recipient prior to, during, or following transplantation. In the context of other (i.e., non-transplant-related) interventions likely to result in ileus, HO-1 would be induced in the bowel shortly before, during, or shortly after the intervention. As used herein, the term "induce(d)" means to cause increased production of a protein, e.g., HO-1, in isolated cells or the cells of a tissue, organ or animal using the cells' own endogenous (e.g., non-recombinant) gene that encodes the protein.

HO-1 can be induced in a patient by any method known in the art. For example, production of HO-1 can be induced by hemin, by iron protoporphyrin, or by cobalt protoporphyrin. A variety of non-heme agents including heavy metals, cytokines, hormones, nitric oxide, $COCl_2$, endotoxin and heat shock are also strong inducers of HO-1 expression (Otterbein et al., Am. J. Physiol. Lung Cell Mol. Physiol. 279:L1029-L1037, 2000; Choi et al., Am. J. Respir. Cell Mol. Biol. 15:9-19, 1996; Maines, Annu. Rev. Pharmacol. Toxicol. 37:517-554, 1997; and Tenhunen et al., J. Lab. Clin. Med. 75:410-421, 1970). HO-1 is also highly induced by a variety of agents and conditions that create oxidative stress, including hydrogen peroxide, glutathione depletors, UV irradiation and hyperoxia (Choi et al., Am. J. Respir. Cell Mol. Biol. 15:9-19, 1996; Maines, Annu. Rev. Pharmacol. Toxicol. 37:517-554, 1997; and Keyse et al., Proc. Natl. Acad. Sci. USA 86:99-103, 1989). A "pharmaceutical composition comprising an inducer of HO-1" means a pharmaceutical composition containing any agent capable of inducing HO-1 in a patient, e.g., any of the agents described above, e.g., hemin, iron protoporphyrin, and/or cobalt protoporphyrin.

HO-1 expression in a cell can be increased via gene transfer. As used herein, the term "express(ed)" means to cause increased production of a protein, e.g., HO-1 or ferritin, in isolated cells or the cells of a tissue, organ or animal using an exogenously administered gene (e.g., a recombinant gene). The HO-1 or ferritin is preferably of the same species (e.g., human, mouse, rat, etc.) as the recipient, in order to minimize any immune reaction. Expression could be driven by a constitutive promoter (e.g., cytomegalovirus promoters) or a tissue-specific promoter (e.g., milk whey promoter for mammary cells or albumin promoter for liver cells). An appropriate gene therapy vector (e.g., retrovirus, adenovirus, adeno associated virus (AAV), pox (e.g., vaccinia) virus, human immunodeficiency virus (HIV), the minute virus of mice, hepatitis B virus, influenza virus, Herpes Simplex Virus-1, and lentivirus) encoding HO-1 or ferritin would be administered to the patient orally, by inhalation, or by injection into the intestinal wall, intestinal lumen, or abdominal cavity at any time before, during, and/or after the ileus-inducing procedure, e.g., about 24 hours or immediately before the ileus-inducing procedure. Similarly, plasmid vectors encoding HO-1 or apo-ferritin can be administered, e.g., as naked DNA, in liposomes, or in microparticles.

Further, exogenous HO-1 protein can be directly administered to a patient by any method known in the art. Exogenous HO-1 can be directly administered in addition to, or as an alternative, to the induction or expression of HO-1 in the patient as described above. The HO-1 protein can be delivered to a patient, for example, in liposomes, and/or as a fusion protein, e.g., as a TAT-fusion protein (see, e.g., Becker-Hapak et al., Methods 24:247-256, 2001).

Alternatively or in addition, any of the products of metabolism by HO-1, e.g., bilirubin, biliverdin, iron, and/or ferritin, can be administered to a patient in conjunction with carbon monoxide in order to prevent or treat ileus. Further, the present invention contemplates that iron-binding molecules other than ferritin, e.g., desferoxamine (DFO), iron dextran, and/or apoferritin, can be administered to the patient. Further still, the present invention contemplates that enzymes (e.g., biliverdin reductase) that catalyze the breakdown any of these products can be inhibited to create/enhance the desired effect. Any of the above can be administered, e.g., orally, intravenously, intraperitoneally, or by direct administration to the inside or outside of the bowel.

The present invention contemplates that compounds that release CO into the body after administration of the compound (e.g., CO-releasing compounds, e.g., photoactivatable CO-releasing compounds), e.g., dimanganese decacarbonyl, tricarbonyldichlororuthenium (II) dimer, and methylene chloride (e.g., at a dose of between 400 to 600 mg/kg, e.g., about 500 mg/kg), can also be used in the methods of the present invention, as can carboxyhemoglobin and CO-donating hemoglobin substitutes.

Administration any of the above can be administered to a patient in any way, e.g., by oral, intravenous, or intraarterial administration. Any of the above compounds can be administered to the patient locally and/or systemically, and in any combination.

The present invention further contemplates treating ileus by administering CO to the patient in combination with functional stimulation of the patient's intestinal tract, e.g., by administering stool softeners, laxatives, and/or lubricants to the patient; and/or by intravenous hydration and/or nasogastric decompression. CO can be administered in combination with any other known methods or compounds for treating ileus.

The invention is illustrated in part by the following examples, which are not to be taken as limiting the invention in any way.

EXAMPLE 1

Protective Effect of Carbon Monoxide for Transplant-Induced Ileus

Animals

Inbred male LEW (RT1) rats weighing 200-300 grams were purchased from Harlan Sprague Dawley, Inc. (Indianapolis, Ind.), and maintained in a laminar flow animal facility at the University of Pittsburgh. Animals were fed with a standard diet ad libitum.

Small Intestinal Transplantation

To determine whether CO is protective against ileus associated with small bowel transplantation, orthotopic SITx was performed in syngenic Lewis rats. SITx with caval drainage was performed using a previously described procedure. The entire donor small intestine from the ligament of Treitz to the ileocecal valve was isolated on a vascular pedicle consisting of the portal vein and of the superior mesenteric artery in community with a segment of aorta. The graft was perfused via the aortic segment with 5 ml chilled Ringer's lactate solution, and the intestinal lumen was irrigated with 20 ml of cold saline solution containing 0.5% neomycin-sulfate (Sigma, St. Louis, Mo.). End-to-side anastomoses between the graft aorta and the recipient infrarenal aorta, and between the graft portal vein and recipient vena cava, were performed with 10-0 Novafil™ suture. The cold ischemic time was 1 hour. The entire recipient intestine was removed and the enteric continuity was restored by proximal and distal end-to-end intestinal anastomoses. Recipient animals were given 20 mg/day prophylactic cefamandole nafate for 3 postoperative days. Transplanted recipients were given water 3 hours after surgery, and were fed 24 hours after surgery.

Experimental Groups

Four groups of animals were examined in this study, two of which received a SITx. Group 1 consisted of unoperated normal rats. Group 2 animals were exposed to CO with no surgery. In Group 3, syngeneic SITx were performed and the recipients kept in room air. Group 4 consisted of SITx recipients that were placed in the CO chamber for 1 hour before surgery and then re-exposed to CO immediately following surgery until sacrificed. In both Groups 3 and 4, normal LEW rats served as donors.

CO Exposure

The animals were exposed to CO at a concentration of 250 ppm. Briefly, 1% CO in air was mixed with air (21% oxygen) in a stainless steel mixing cylinder and then directed into a 3.70 ft$^3$ glass exposure chamber at a flow rate of 12 L/min. A CO analyzer (Interscan, Chatsworth, Calif.) was used to measure CO levels continuously in the chamber. CO concentrations were maintained at 250 ppm at all times. The animals were supplied food and water during the exposures.

Functional Studies

The effect of CO treatment on intestinal dysmotility in transplanted grafts was assessed both in vitro and in vivo. Tissues were harvested 24 or 48 hours post-operatively, which have been shown to be time points during which transplant-induced dysmotility peaks. In vitro circular muscle mechanical activity was measured as previously described (Eskandari et al., Am. J. Physiol. 273(3 Pt 1):G727-34 (1997)). Rats were anesthetized and killed by exsanguination 24 hours post-operatively. A segment of mid-jejunum was pinned in a Sylgaard™ lined dissecting dish containing pre-oxygenated Krebs-Ringer-bicarbonate buffer (KRB; in mM: 137.4 Na$^+$, 5.9 K$^+$, 2.5 Ca$^{2+}$, 1.2 Mg$^{2+}$, 134 Cl$^-$, 15.5 HCO$_3^-$, 1.2 H$_2$PO$_4^-$, and 11.5 glucose) that was equilibrated with 97% O$_2$/3% CO$_2$. The intestine was opened along the mesenteric border and the mucosa removed by stripping with fine forceps. Full-thickness strips of muscularis (1×6 mm) were cut parallel to the circular muscle layer. Muscle strips were mounted in standard horizontal mechanical organ chambers that were continuously superfused with pre-oxygenated KRB maintained at 37° C. One end of each strip was attached by ligature to a fixed post and the other to an isometric force transducer (WPI, Sarasota, Fla.). Strips were allowed to equilibrate for 1 hour, after which they were incrementally stretched to the length at which maximal spontaneous contraction occurred (L$_o$). After a second equilibration period of 30 minutes, contractility-response curves were generated by exposing the tissues to increasing concentrations of the muscarinic agonist bethanechol (0.3 to 300 µM) for 10 minutes, followed by a 10-minute wash period. Contractile activity was calculated by integrating the area under the trace, normalized by converting the weight and length of the strip to square millimeters of tissue (1.03 mg/mm$^2$), and reported as g/s/mm$^2$.

Intestinal transit was measured in controls and manipulated animals 48 hours postoperatively by evaluating the intestinal distribution of fluorescein-labeled dextran (Molecular Probes). Animals were lightly sedated with inhaled isofluran and fed orally with labeled dextran (200 µl of 6 mg/ml in saline). Two hours after administration, the animal was sacrificed and the entire bowel from stomach to distal colon was collected. The contents of the stomach, small bowel (divided into 10 segments of equal length), cecum, and colon (3 segments; proximal, mid and distal) were opened, placed in 2 ml of saline, and vortexed vigorously to release the dextran present in each segment. After pelleting the intestinal tissue and chyme, aliquots of the supernatant were read in duplicate on a plate reader (CytoFluor II; excitation wavelength 530 nm and emission 590 nm) for quantification of the fluorescent signal in each bowel segment. A median histogram of the fluorescence signal was then plotted to demonstrate changes in the distribution of labeled dextran among experimental groups. Intestinal transit was determined for statistical analysis by calculating the geometric center (GC).

Morphological Studies

Histopathological Study

Small intestinal grafts were fixed in 10% buffered formalin and embedded in paraffin. Sections were cut at a thickness of 4 µm and stained with hematoxylin and eosin.

Myeloperoxidase Histochemistry

Muscularis whole mounts were prepared from the mid small intestine collected 24 hours post-operatively. Segments of intestine were immersed in KRB in a Sylgaard™-lined glass dish and pinned without stretching along the mesenteric border. The length and width of the segments were measured with a caliper. The colon was then opened along the mesenteric border and stretched to 150% of the length and 250% of the width. The mucosa and submucosa were removed using fine forceps, and the remaining tissue fixed in 100% denatured ethanol for 30 minutes. After washing several times with PBS, the tissue was treated with Hanker-Yates reagent for detection of polymorphonuclear neutrophils (PMN's) exhibiting myeloperoxidase (MPO) activity (Sheibani et al, Am. J. Clin. Pathol. 75(3):367-70 (1981)). Tissues were mounted on glass slides using Gel/Mount™ (Biomedia Corp., Foster City, Calif.), cover-slipped and inspected by light microscopy (Nikon FXA, Fryer, Huntley, Ill.) at a magnification of 200×. Numbers of MPO-positive PMN's infiltrating the muscularis externae were determined from the mean counts collected from five to six adjacent optical fields centered between the mesenteric and anti-mesenteric borders.

Molecular Biological Studies

RNase Protection Assay (RPA)

To investigate the sequential analysis of cytokine mRNA expression in the mucosa and muscularis, RNase protection assay was performed with the Riboquant™ kit (Pharmingen) according to the protocol of the manufacturer. Radiolabeled antisense RNA multiple probes were synthesized using an in vitro transcription kit and rat cytokine multi-probe template set (rCK-1), which included probes for cytokines (Interleukin (IL)-1α, IL-1β, IL-2, IL-3, IL-4, IL-5, IL-6, IL-10, TNF-α, TNF-β and IFN-γ) and housekeeping genes (L32 and GAPDH). $^{32}$P-labeled probes (8.0×10$^5$ cpm) and sample RNA (5 µg) were hybridized at 56° C. for 12-16 hours, and single-stranded RNAs including antisense RNA probes were digested by using RPA Kit (Pharmingen). Protected probes were loaded on a 40% polyacrylamide gel. Autoradiography was performed using a PhosphorImager™ system (Molecular Dynamics, Krefeld, Germnany). Quantification of radio-activity of mRNA bands was performed with NIH Image, normalized to GAPDH, and expressed as a ratio of cytokine /GAPDH (n=3-4).

SYBR Green Real Time RT-PCR

The effects of inhalation of CO on transplant-induced pro-inflammatory and anti-inflammatory gene expression was assessed in muscularis extracts by RT-PCR. Muscularis externae was collected from normal intestine and transplanted grafts 4 hours postoperatively and snap frozen in liquid nitrogen. This time point falls within the range of maximum inflammatory mediator expression that occurs between 3 and 6 hours following abdominal incision. Total RNA extraction was performed using the guanidium-thiocyanate phenol-chloroform extraction method as described previously (Eskandari et al., Am. J. Clin. Pathol. 75(3):367-370 (1997)). RNA pellets were resuspended in RNA-secure resuspension solution (Ambion Inc., Austin, Tex.), followed by removal of potentially contaminating DNA by treatment with DNase I (DNA-Free Kit, Ambion Inc., Austin, Tex.). Equal aliquots (5 μg) of total RNA from each sample were quantified by spectrophotometry (wavelength 250 nm) and aliquoted at a concentration of 40 ng/μl. Peak mRNA expression was quantified in duplicate by SYBR Green two-step, real-time RT-PCR. GAPDH was used as the endogenous reference. Aliquoted RNA was subjected to first-strand complementary DNA (cDNA) synthesis using random hexamers (PE applied Biosystems, Foster City, Calif.) and Super Script II™ (Life Technologies, Rockville, Md.). Primer sequences were obtained from the literature or designed according to published sequences (Table 1). A PCR reaction mixture was prepared using SYBR Green PCR Core Reagents (PE Applied Biosystems). Each sample was estimated in duplicate using the conditions recommended by the manufacturer. The reaction was incubated at 50° C. for 2 min to activate the uracil N'-glycosylase and then for 12 min at 95° C. to activate the Amplitaq Gold™ polymerase followed by 40 cycles of 95° C. for 15 sec and 60° C. for 1 min on an ABI PRISM 7700™ Sequence Detection System (PE Applied Biosystems, Foster City, Calif.). Real-time PCR data were plotted as the $\Delta R_n$, fluorescence signal versus the cycle number. An arbitrary threshold was set to the mid-linear portion of the log $\Delta R_n$, cycle plot. The threshold cycle ($C_T$) was defined as the cycle number at which the $\Delta R_n$, crosses this threshold. Quantification of mRNA expression was normalized to GAPDH and calculated relative to control using the comparative $C_T$ method (Schmittgen et al., J. Biochem. Biophys. Methods 46(1-2):69-8 (2000)).

To exclude PCR amplification of contaminating genomic DNA, RT-negative controls (samples containing RNA that was not reverse transcribed) were included in each PCR reaction. Melting curve analyses were performed for each reaction to ensure amplification of specific product. In addition, the primers were subjected to gel electrophoresis to confirm the absence of non-specific bands and to confirm that the amplicons were of the correct size. Efficiency of PCR-amplification of target cDNA was examined to measure colinearity of dilution. Serial 3-fold dilutions of cDNA were performed in triplicate. Standard curves were generated by plotting $C_T$ value against relative input copy number. Slopes of the standard curves of −3.2±0.3 with correlation coefficients of 0.99 were considered to be acceptable, having corresponding efficiencies of 100±10%.

TABLE 1

Primer summary

| Primer | Sequence 5' to 3' | SEQ ID NO | Source |
|---|---|---|---|
| GAPDH | ATGGCACAGTCAAGGCTGAGA | 1 | NM_017008 |
|  | CGCTCCTGGAAGATGGTGAT | 2 |  |
| IL-6 | GCCCTTCAGGAACAGCTATGA | 3 | M26744 |
|  | TGTCAACAACATCAGTCCCAAGA | 4 |  |
| IL-1β | CACCTCTAAGCAGAGCACAG | 5 | Li & Wang, Brain |
|  | GGGTTCCATGGTGAAGTCAAC | 6 | Research Protocols 2000; 5,211-217 |
| TNFα | GGTGATCGGTCCCAACAAGGA | 7 | Fink et al. |
|  | CACGCTGGCTCAGCCACTC | 8 | Nature Med 1998; 4: 1329-1333. |
| ICAM-1 | CGTGGCGTCCATTTACACCT | 9 | NM_012967 |
|  | TTAGGGCCTCCTCCTGAGC | 10 |  |
| iNOS | GGAGAGATTTTTCACGACACCC | 11 | NM_012611 |
|  | CCATGCATAATTTGGACTTGCA | 12 |  |
| COX-2 | CTCTGCGATGCTCTTCCGAG | 13 | AF233596 |
|  | AAGGATTTGCTGCATGGCTG | 14 |  |
| IL-10 | TGCAACAGCTCAGCGCA | 15 | Harness et |
|  | GTCACAGCTTTCGAGAGACTGGAA | 16 | al., J. Neurol. Sci. 2001; 187,7-16. |

Northern Blotting of HO-1

Northern blotting was performed as described previously (Camhi et al., Am. J. Respir. Cell Mol. Biol. 13:387-398 (1995)). Briefly, 10 μg of total RNA extracted from the tissue as described above was electrophoresed in a 1% agarose gel and then transferred to nylon membranes by capillary action. The nylon membranes were then prehybridized in hybridization buffer [1% bovine serum albumin (BSA), 7% SDS, 0.5 M $PO_4$ buffer, pH 7.0, and 1 mM EDTA] at 650° C. for 2 h followed by hybridization with $^{32}P$-labeled rat HO-1 cDNA, $^{32}P$-labeled rat L-ferritin, or $^{32}P$-labeled rat H-ferritin oligonucleotide probes at 65° C. for 24 h. Nylon membranes were then washed in buffer A (0.5% BSA, 5% SDS, 40 mM $PO_4$ buffer, pH 7.0, and 1 mM EDTA) for 15 min two times at 65° C. followed by washes in buffer B (1% SDS, 40 mM $PO_4$ buffer, pH 7.0, and 1 mM EDTA) for 15 min three times at 65° C.

HO-1 cDNA Probe

A full-length rat cDNA (pHO1) was generously provided by Dr. S. Shibahara of Tohoku University (Sendai, Japan). pHO1 was subcloned into pBluescript vector, and a HindIII/EcoRI digestion was performed to isolate the 0.9-kb HO-1 cDNA insert out of the pBluescript vector. To control for variation in either the amount of RNA in different samples or loading errors, blots were hybridized with an oligonucleotide probe corresponding to the 18S rRNA. A 24 base pair oligonucleotide (5'-ACGGTATCTGATCGTCTTCGAACC-3'; SEQ ID NO: 31) complementary to the 18S RNA was synthesized using a DNA synthesizer (Applied Biosystems, Foster City, Calif.). The HO-1 cDNA was labeled with [$^{32}P$] CTP using the random primer kit from Boehringer Mannheim (Mannheim, Germany). All oligonucleotide probes were labeled with [$^{32}P$] ATP at the 3' end with terminal deoxynucleotidyltransferase (Bethesda Research Laboratories, Gaithersburg, Md). Autoradiograph signals were compared to 18S rRNA obtained from the same blot.

Determination of Serum Cytokine Levels

Serum samples were taken sequentially at 1, 4 and 24 hours after reperfusion and stored at −80° C. until evaluation.

Serum cytokine concentrations, including IL-6, IL-10 and TNFα, were determined using rat enzyme-linked immunoassay (ELISA) kits as described by the manufacturer (R & D, Cambridge, Mass.).

Measurement of Serum Nitrite/Nitrate Levels

To monitor the stable end-products of NO metabolism, serum nitrate/nitrate levels at 1, 4, and 24 hrs were measured using a commercially available test kit (Cayman, Ann Arbor, Mich.) and quantified according to the manufacturer's directions. In this assay system, nitrate is reduced to nitrite using nitrate reductase, and the nitrite concentration of the sample is subsequently measured using the Griess reaction.

Muscle Cell Culture

The small bowel of control and transplanted rats was removed (under sterile conditions) 24 hours post-operatively. The colon was left in situ. The intestine was transferred to a sterile beaker containing Hank's balanced salt solution (Sigma, St. Louis, Mo.) with 200 U/ml penicillin G and 200 μ/ml streptomycin (HBSS). The muscularis were isolated as described above and blotted onto sterile gauze. The wet weight of samples was determined, and aliquots of 150-200 milligrams of tissue were created. Tissues were washed twice in HBSS. Aliquots were transferred to 35 millimeter well culture plates containing 3 ml of serum-free DMEM containing penicillin/streptomycin, as above, and incubated for 24 hrs in a 5% $CO_2$ incubator at 37° C. After the incubation period, 1 ml aliquots of the supernatant were frozen in liquid nitrogen and stored at −80° C. Cytokine protein levels were measured by ELISA and normalized to the tissue wet weight. Commercially available ELISA kits were used according to the manufacturers' instructions.

Data Analysis

Results are expressed as mean plus or minus the standard error of the mean (SEM). Statistical analysis was performed using Student's t test or analysis of variations (ANOVA) where appropriate. A probability level of $p \leq 0.05$ was considered statistically significant.

CO Suppresses the Development of Intestinal Dysfunction Associated with SITx

The effects of SITx and treatment with CO on spontaneous and bethanechol-stimulated small intestinal circular muscle contractility were investigated in organ bath experiments in vitro. Tissues were harvested 24 hours after reperfusion of the transplanted intestinal graft. Muscle strips from control intestine generated regular contractions (data not shown). Treatment with CO for 24 hours had no effect on spontaneous contractile activity in unoperated control rats (data not shown). After SITx, spontaneous contractile activity was lost (data not shown). CO treatment restored spontaneous contractile activity in transplanted rats (data not shown).

The addition of bethanechol (0.3 to 300 μM) to the bath superfusate elicited concentration-dependent tonic contractions. Integrated contractile responses normalized to tissue area obtained in response to increasing doses of bethanechol are shown in FIG. 1. In control animals, contractile force was concentration dependent over the range of 10 to 300 μM bethanechol, with a peak force of 3.5±0.7 $g/mm^2/s$ generated in response to 100 μM bethanechol. Treatment with CO had no effect on contractility in unoperated animals (peak contractile force 3.2±0.5 $g/mm^2/s$). SITx led to a reduction in contractile force generated throughout the dose-response curve compared with controls that reached statistical significance at bethanechol concentrations greater than 10 μM. At 100 μM bethanechol, peak contractile force was reduced by 49% to 1.7±0.4 $g/mm^2/s$. Treatment with CO prevented the inhibitory effect of SITx throughout the dose-response curve, restoring peak contractile force to control levels (3.6±0.7 $g/mm^2/s$).

Figure 2A:
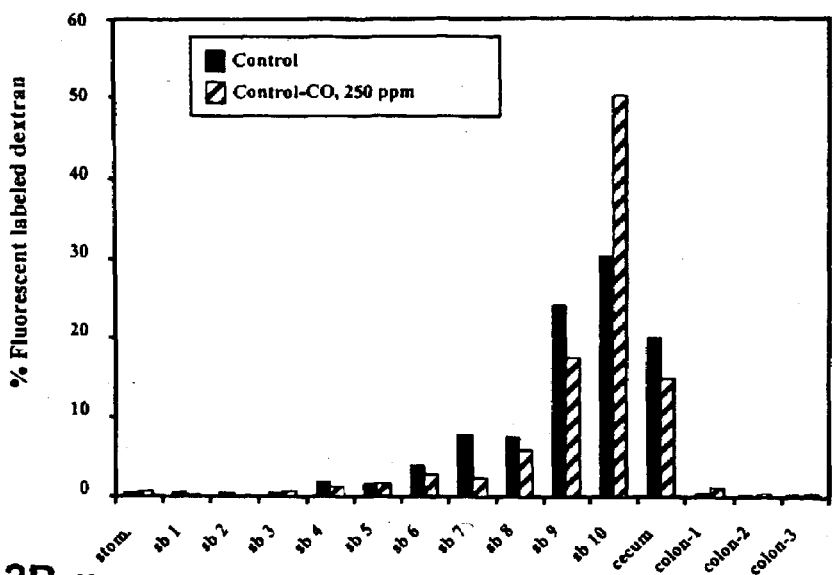
FIG. 2A is a bar graph that illustrates the effect of CO on intestinal transit in control animals (animals not subjected to SITx). Solid bars=control; striped bars=control+CO (250 ppm); stom=stomach; sb=small bowel.
Figure 2B:
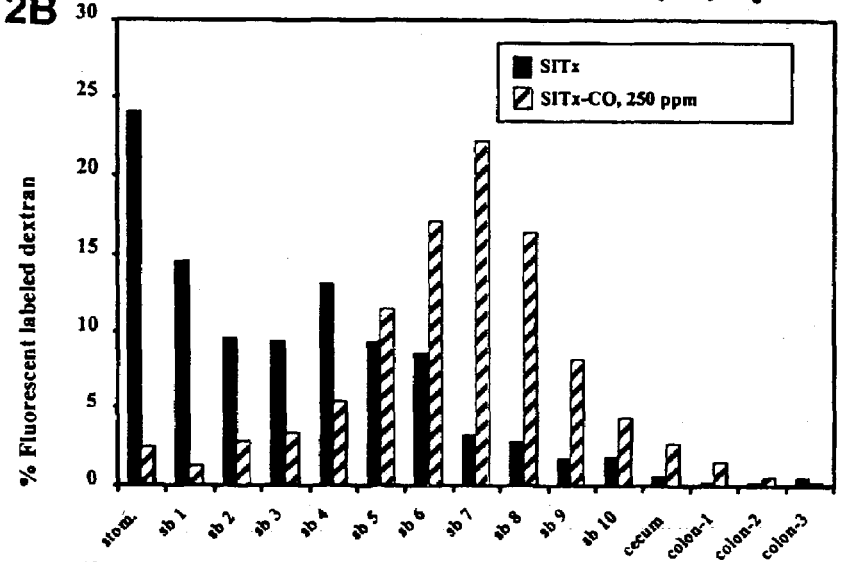
FIG. 2B is a bar graph that illustrates the effect of CO on intestinal transit in animals that have undergone SITx. Solid bars=SITx; striped bars=SITx+CO (250 ppm); stom=stomach; sb=small bowel; and col=colon.
Figure 2C:
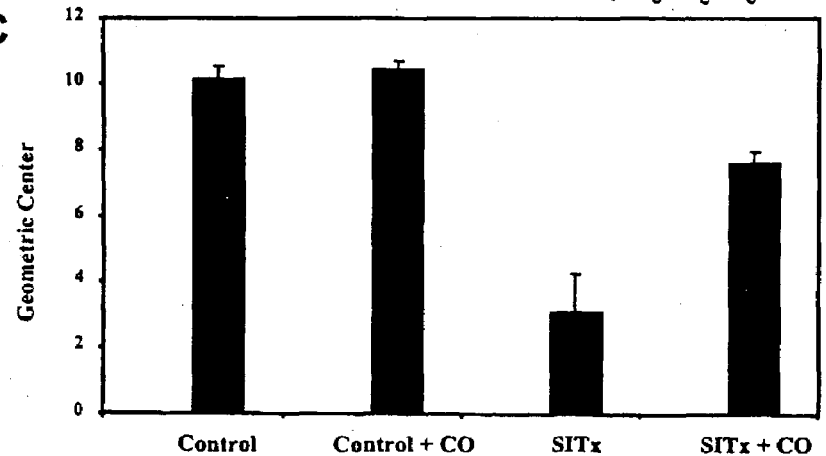
FIG. 2C is a bar graph illustrating that CO significantly improved intestinal transit in rats that have undergone SITx. The graph summarizes calculated transit geometric center measurements. Control=control animals exposed to air; control+CO=control animals exposed to CO; SITx=animals receiving SITx and exposed to air; SITx+CO=animals receiving SITx and exposed to CO.

Intestinal transit was measured in controls and transplanted animals 48 hours postoperatively by evaluating the intestinal distribution of orally-fed, fluorescein-labeled dextran. FIGS. 2A-2B are transit histograms illustrating distribution of non-absorbable FITC-labeled dextran along the gastrointestinal tract (from stomach to colon) 2 hours after oral administration. A median histogram of the fluorescence in each bowel segment, 2 hours after oral feeding, from unoperated control rats and from control rats treated with CO is plotted in FIG. 2A. In both groups, the majority of the fluorescent label was located in small bowel segments 9 and 10, and in the cecum. This is in contrast to the distribution pattern observed in transplanted rats (FIG. 2B), where fluorescent label was found primarily in the stomach, with some label entering the proximal small bowel. In transplanted animals treated with CO, the distribution of label was more distal, accumulating primarily within small bowel segments 6, 7 and 8. Statistical analyses of the results from calculation of Geometric Center, summarized in FIG. 2C, demonstrate that inhalation of CO significantly improved intestinal transit in rats that underwent small bowel transplantation.

Leukocyte Recruitment

Figure 3:
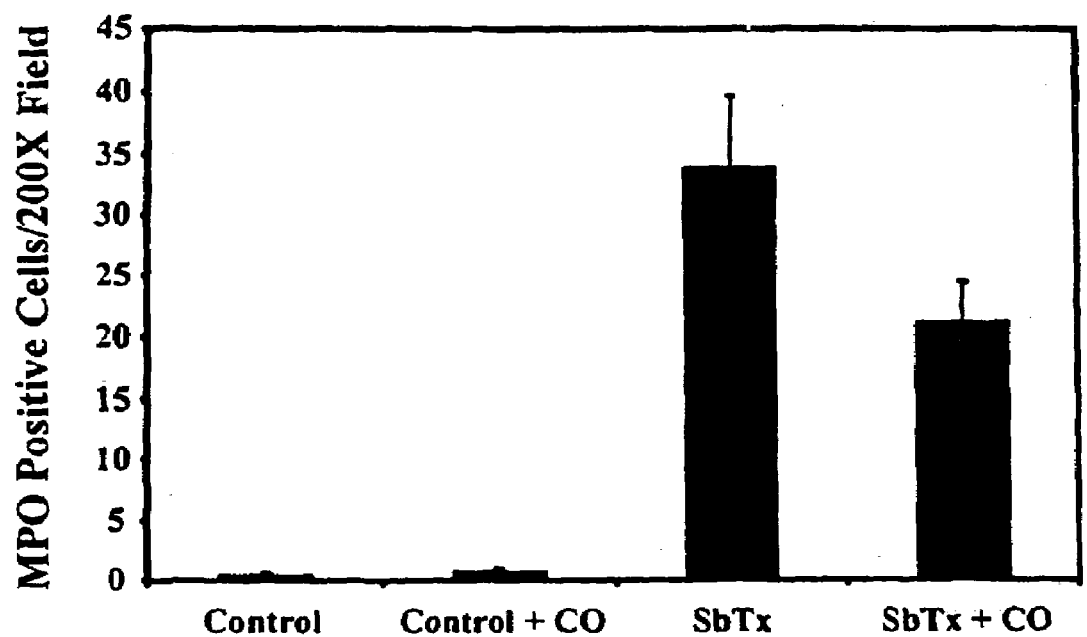
FIG. 3 is a bar graph that illustrates the effect of CO on leukocyte recruitment into the intestinal muscularis following SITx. Control=control animals exposed to air; control+CO=control animals exposed to CO; SbTx=animals receiving SITx and exposed to air; SbTx+CO=animals receiving SITx and exposed to CO.

Cellular inflammatory events in the small intestinal muscularis were characterized 24 hours after SITx. Myeloperoxidase (MPO) activity, as determined by Hanker-Yates histochemstry, was used to quantify leukocyte infiltrate in tissues from control and transplanted animals, with and without CO treatment. In unoperated control and CO-treated control rats, MPO-positive cells were rare (data not shown). SITx resulted in a significant recruitment of leukocytes into the intestinal muscularis (data not shown). Cell counts per 200× field are summarized in FIG. 3, which shows that CO treatment decreased the mean number of MPO positive cells; however, this reduction did not achieve statistical significance (p=0.08, n=6).

Sequence Analysis of Cytokines in Mucosal and Muscular Layers

Figure 4A:
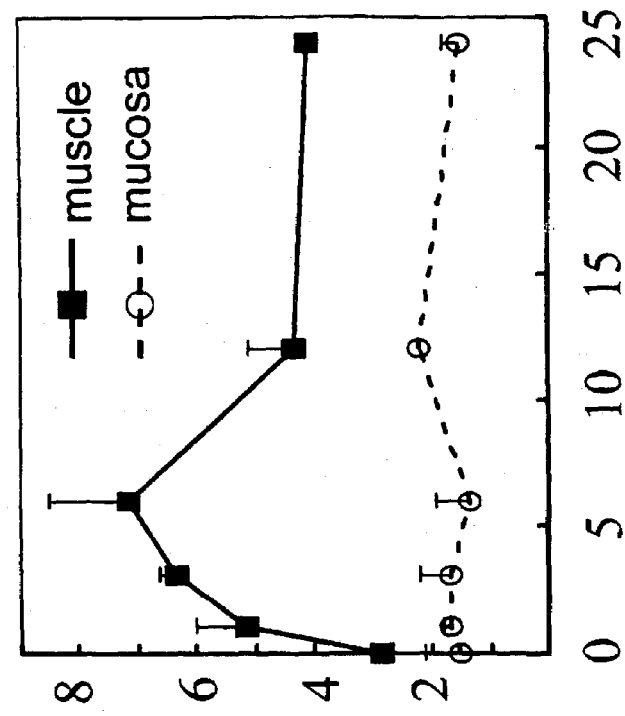
FIG. 4A is a line graph that illustrates IL-6 mRNA expression in the mucosa and muscularis at various time points after SITx, as measured by RNase protection assay. ■=muscle; ○=mucosa.
Figure 4B:
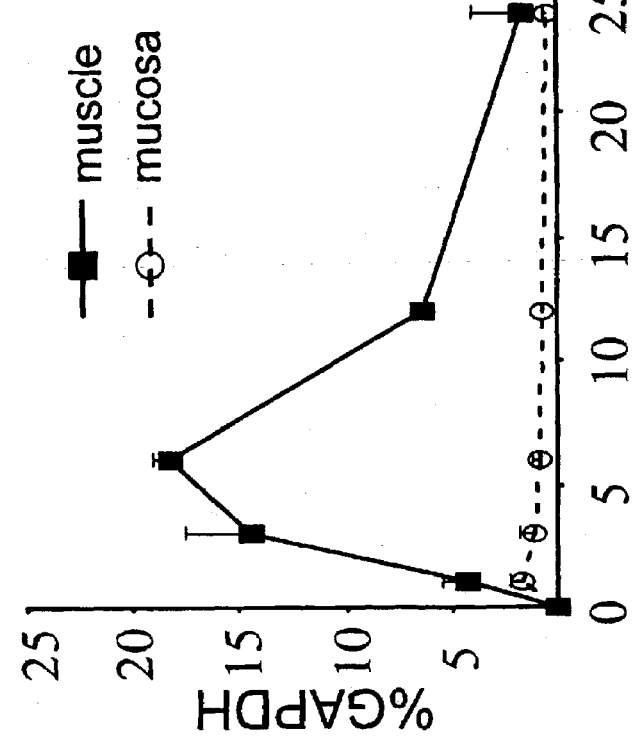
FIG. 4B is a line graph that illustrates IL-1β mRNA expression in the mucosa and muscularis at various time points after SITx, as measured by RNase protection assay. ■=muscle; ○=mucosa.

RNase protection assays demonstrated that SITx caused a significant upregulation of both IL-6 and IL-1β mRNAs, which peaked 3 -6 hours within the transplanted graft. (FIGS. 4A and 4B). Accordingly, inflammatory mediator mRNA levels were analyzed 4 hours after reperfusion.

Molecular Inflammatory Response

Figure 5:
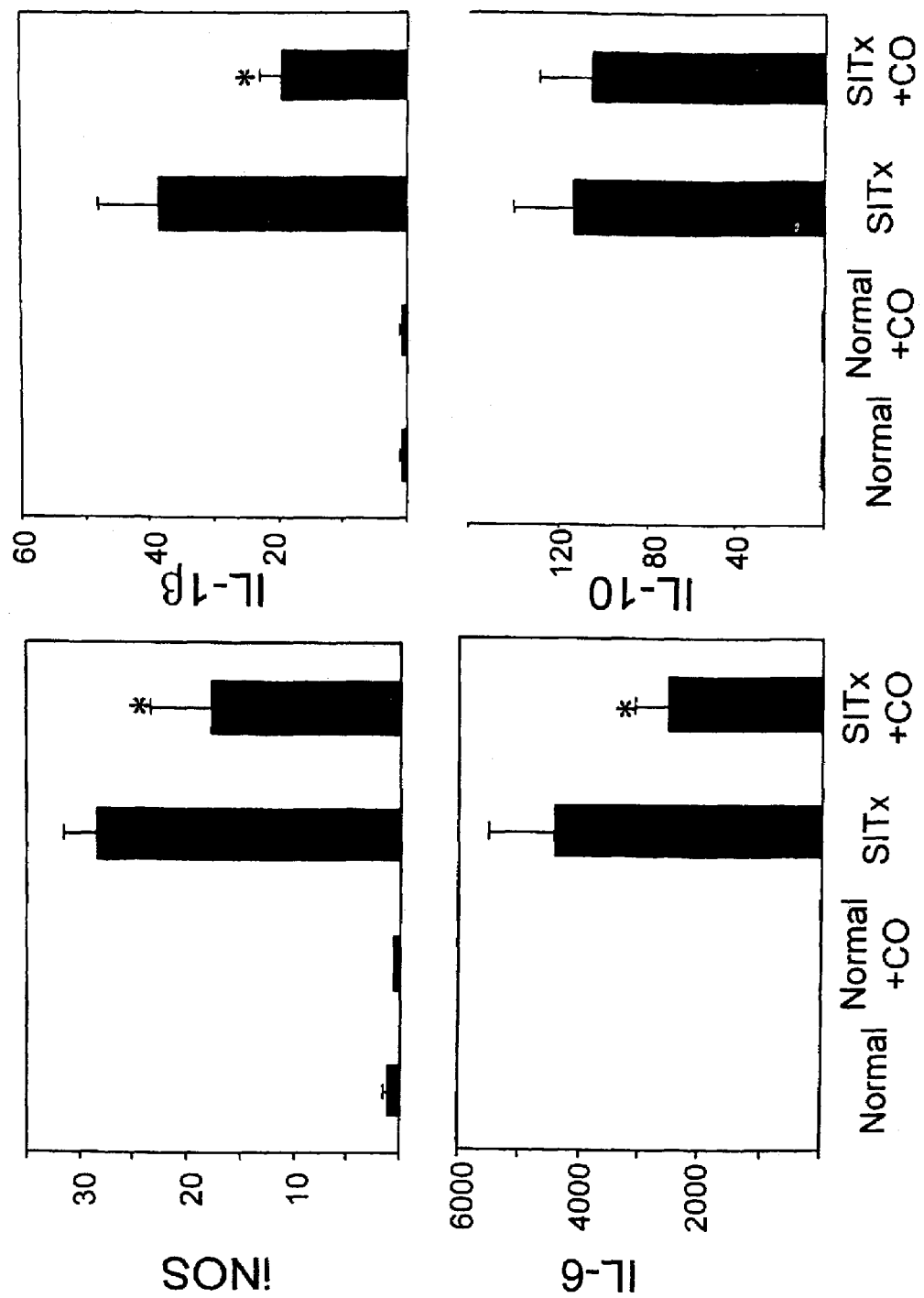
FIG. 5 is a set of bar graphs that illustrate the effect of CO on nitric oxide synthase (iNOS), IL-6, IL-1β, and IL-10 expression in the muscularis externae of intestinal grafts four hours after reperfusion, as measured by real time RT-PCR analysis. Normal=control animals exposed to air; Normal+CO=control animals exposed to CO; SITx=animals receiving SITx and exposed to air; SITx+CO=animals receiving SITx and exposed to CO.

FIG. 5 is a set of bar graphs that illustrate the effect of CO on nitric oxide synthase (iNOS), IL-6, IL-1β, and IL-10 expression in the muscularis externae of intestinal grafts four hours after reperfusion. Real time PCR analysis revealed a significant increase in pro-inflammatory cytokine mRNA expression (IL-6 (3400-fold) and IL-1β (38-fold)) in the muscularis externae of intestinal grafts. TNFα was also significantly upregulated, but to a lesser degree (3-fold). ICAM-1 gene expression, an adhesion molecule that plays an important role in the recruitment of circulating inflammatory cells, was increased 14-fold. In recipient rats treated with CO, the mean relative IL-6 and IL-1β expression was reduced (by 40% and 50%, respectively), whereas TNFα and ICAM-1 expression was unchanged. Due to large standard deviation among the transplanted groups, the decrease in IL-6 mRNA expression in CO treated rats did not achieve statistical significance (p=0.084, n=6) whereas IL-1β expression was significantly reduced (p=0.046, n=6). Gene expression of the inducible forms of cyclooxygenase (COX-2) and nitric oxide synthase (iNOS) were also significantly upregulated in the muscularis of transplanted grafts (5-fold and 48-fold, respectively). The mean relative mRNA expression of both enzymes was reduced by approximately 50% in CO-treated rats. Once again, the reduction in iNOS expression was not quite significant (p=0.060, n=6) whereas the reduction in COX-2 expression was quite significant (p=0.26, n=6). Inhalation of CO alone had no effect on the expression of any of the mediators studied.

Figure 6:
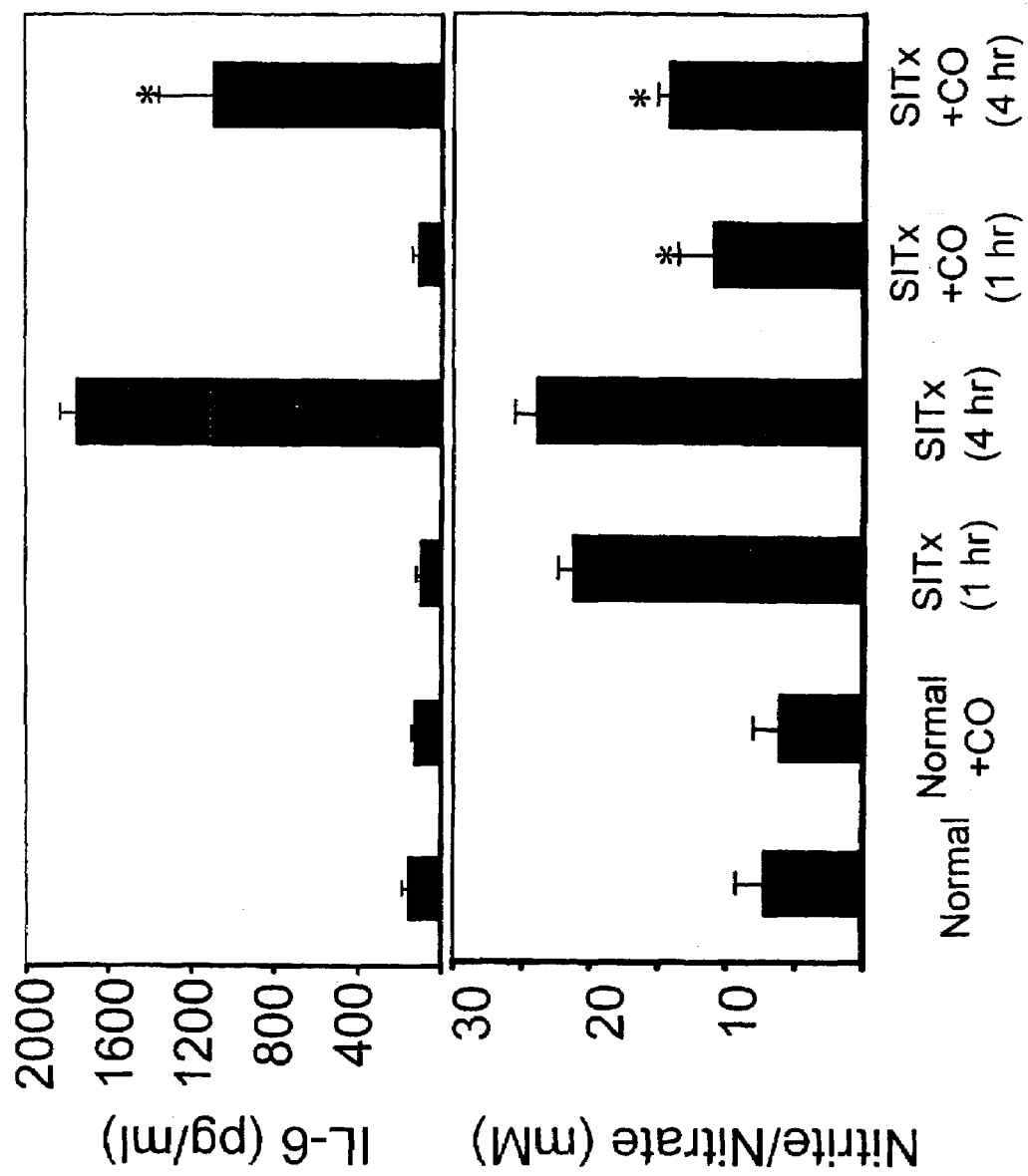
FIG. 6 is a set of bar graphs that illustrate the effect of CO on serum IL-6 and nitrate/nitrite concentrations in animals that underwent SITx as measured one (SITx+CO (1 hr)) and four (SITx+CO (4 hr)) hours after reperfusion. Normal=control animals exposed to air; Normal+CO=control animals exposed to CO; SITx (1 hr) and SITx (4 hr)=animals that underwent SITx as measured one and four hours after reperfusion, respectively.

FIG. 6 is a set of bar graphs that illustrate the effect of CO on serum IL-6 and nitrate/nitrite concentrations in animals receiving intestinal grafts at one and four hours after reperfusion. To generate these data, serum samples were taken at various time points following transplantation and stored at −80° C. until evaluation. Serum IL-6 concentrations were determined using a rat enzyme-linked immunoassay (ELISA) kit (R&D, Cambridge, Mass.). The serum nitrite/nitrate levels, the stable end products of NO metabolism, were measured using a commercially available test kit (Cayman, Ann Arbor, Mich.). In this assay system, nitrate is reduced to nitrite using nitrate reductase, and nitrite concentration of the sample was subsequently measured using the Griess reaction. Serum IL-6 and nitrite/nitrate levels in animals subjected SITx and treated with air increased over time. Animals subject to SITx and treated with CO (SITx+CO) showed significantly decreased serum levels of both IL-6 and nitrite/nitrate.

Data demonstrating that CO protects against transplant induced intestinal dysfunction are tabulated in Table I, below. Early (<48 hours) after SITx, intestinal grafts suffered from a significant delay in intestinal transit, reduction of muscle contractility, and massive inflammatory infiltrates. These changes were reduced in recipients treated with CO. Serum IL-6 concentrations (4 hours after reperfusion) were significantly lower in SITx with CO compared to SITx without CO. CO prevented intestinal graft inflammation and I/R injury associated with SITx by down regulating the pro-inflammatory cytokines IL-6 and IL-1.

Surgical Manipulation. Mice were anesthetized with inhaled isoflurane and the abdomen opened by midline laparotomy. The small intestine was eventrated and gently compressed along its entire length using moistened sterile cotton applicators. This procedure is designed to simulate "running" of the bowel commonly performed during abdominal surgery in the clinical setting. The bowel was repositioned in the abdominal cavity and the incision closed by two layers of continuous sutures. The duration of the procedure was approximately 15 minutes and the animals moved freely about their cage within 20 minutes of withdrawal of anesthetic.

CO Inhalation Treatment. Mice housed in cages were placed in plexiglass chambers that were continuously ventilated with air or with air containing CO (250 ppm). A sampling port was provided to continuously monitor carbon monoxide concentrations within the chamber. Animals had free access to food and water at all times. Mice were exposed to CO or air 1 hour prior to laparotomy, removed for surgical manipulation, and then returned to the chamber for 24 hours. Mice not undergoing surgery were removed from the chamber for a similar length of time and then returned to the chamber for 24 hours.

Morphological Studies

MPO Histochemistry. Muscularis whole-mounts were prepared from the mid-jejunum collected 24 hr post-operatively. Segments of intestine were immersed in KRB in a Sylgard lined glass dish (Midland, Mich.) and pinned without stretching along the mesenteric border. The length and width of the segments were measured with a caliper. The jejunal segment was then opened along the mesenteric border and stretched to 150% of the length and 250% of the width. The mucosa was removed using fine forceps, and the remaining tissue fixed in 100% denatured ethanol for 30 min. After washing several times with PBS, the tissue was treated with Hanker-Yates reagent (Polysciences, Wairrington, Pa.) for detection of

TABLE 2

CO suppresses intestinal dysfunction associated with SITx.

| | Intestinal transit | Contractile force (g/s/mm$^2$) | Inflammatory infiltrates (/200x field) | IL-1β mRNA (% GAPDH) | IL-6 mRNA (% GAPDH) | Serum IL-6 (pg/ml) |
|---|---|---|---|---|---|---|
| Normal | normal | 2.5 ± 0.1 | 4.2 ± 1.1 | 0 | 0.8 ± 0.1 | 273 |
| SITx | delayed | 1.0 ± 0.3 | 37 ± 8.4 | 12.2 ± 2.7 | 41.9 ± 3.8 | 6042 |
| SITx + CO | normal | 3.0 ± 0.4 | 21 ± 3.2 | 6.6 + 0.1 | 22.3 ± 1.8 | 1439 |

EXAMPLE 2

CO Suppresses the Development of Ileus Associated With Surgical Manipulation of the Small Intestine Animals C57Bl6 wild type male mice (20-25 g) were obtained from Harlan (Indianapolis, Ind.). Mice were housed in a pathogen-free facility, maintained on a 12-hour light/dark cycle, and fed commercially available rodent chow and tap water ad libitum.

Experimental Groups and Operative Procedures

Age-matched mice were divided into four experimental groups: naive controls (Control); controls treated with CO (Control+CO); mice subjected to surgical manipulation of the small intestine (IM); and mice subjected to surgical manipulation and treatment with CO (IM+CO).

polymorphonuclear neutrophils (PMN's) exhibiting myeloperoxidase (MPO) activity. Tissues were mounted on glass slides using Gel/Mount™ (Biomedia Corp., Foster City, Calif.), cover-slipped and inspected by light microscopy (Nikon Microphot-FXA, Fryer, Huntley, Ill.) at a magnification of 200×. PMN's were counted in five to six adjacent optical fields centered between the mesenteric and antimesenteric borders.

HO-1 Immunohistochemistry. Muscularis whole-mounts prepared as above were fixed in Zamboni's fixative for 1 hour, cleared with DMSO. After washing several times with PBS, tissues were treated with PBS containing 10% normal donkey serum and 0.1% Triton-X. Whole-mounts were then incubated overnight with rabbit anti-rat HO-1 antibody (1:500, Stressgen, Vancouver, Canada), washed, and incubated for 2 hr. with donkey anti-rabbit IgG-Cy3 conjugate (Jackson ImmunoResearch Laboratories, Inc., West Grove, Pa.). Tissues were mounted with Gel/Mount™ as above and inspected by fluorescence microscopy (Nikon Microphot-FXA, Huntley, Ill.).

Functional Studies

Mice were anesthetized and killed by exsanguination at the end of the 24-hour chamber treatment with CO or room air. In vitro circular muscle mechanical activity was measured as previously described in Eskandari et al. (Am. J. Physiol. 273:G727-G734 (1997)). Briefly, a segment of mid small bowel was pinned in a Sylgard™ (Midland, Mich.) lined dissecting dish containing pre-oxygenated Krebs-Ringer-bicarbonate buffer (KRB; in mM: 137.4 $Na^+$, 5.9 $K^+$, 2.5 $Ca^{2+}$, 1.2 $Mg^{2+}$, 134 $Cl^-$, 15.5 $HCO_3^-$, 1.2 $H_2PO_4^-$, and 11.5 glucose), gassed with 97% $O_2$/3% $CO_2$ to establish a pH of 7.4. The intestine was opened along the mesenteric border, and the mucosa removed by stripping with fine forceps. Full-thickness strips of muscularis (1×6 mm) cut parallel to the circular muscle layer were mounted in standard horizontal mechanical organ chambers and were continuously superfused with preoxygenated KRB maintained at 37° C. One end of each strip was attached by ligature to a fixed post and the other to an isometric force transducer (WPI, Sarasota, Fla.). Strips were allowed to equilibrate for 1 hour, after which they were incrementally stretched to $L_o$ (length at which maximal spontaneous contraction occurs). After a baseline recording period of 30 min, contractility-response curves were generated by exposing the tissues to increasing concentrations of the muscarinic agonist bethanechol (0.3 to 300 μM) for 10 minutes, followed by intervening 10-minute wash periods. Contractile activity was calculated by integrating the area under the trace. The response was normalized to the amount of tissue by converting the weight (1.03 mg/mm$^2$) and length of the strip to square millimeters of tissue, and reported as g/s/mm$^2$. Intestinal transit was measured in controls and manipulated animals 24 hours postoperatively by evaluating the intestinal distribution of a non-absorbable fluorescein-labeled dextran (MW 70,000). Animals were lightly sedated with isofluran and fed orally with labeled dextran (100 μl of 25 mg/ml stock solution). Ninety minutes after administration, the animal was sacrificed and the entire bowel from stomach to distal colon was collected. The contents of the stomach, small bowel (divided into 10 segments of equal length), the cecum, and colon (3 segments of equal length) were each minced in 1 ml of saline and mixed vigorously to release the dextran present in each segment. After pelleting the intestinal tissue and chyme, aliquots of the cleared supernatant were read in duplicate on a plate reader (CytoFluor II; excitation wavelength 530 nm and emission 590 nm) for quantification of the fluorescent signal in each bowel segment. The distribution of signal along the gastrointestinal tract was determined by calculating the geometric center (GC=Σ(percent of total fluorescent signal in each segment×the segment number) for quantitative statistical comparison among experimental groups.

SYBR Green Real Time RT-PCR

Pro- and anti-inflammatory gene expression was determined by real time RT-PCR. The small intestinal muscularis externa was collected at 4 time points (3, 6, 12, and 24 hr) postoperatively and snap frozen in liquid nitrogen. Total RNA extraction was performed using the guanidium-thiocyanate phenol-chloroform extraction method as described in Eskandari et al. (Id.) RNA pellets were resuspended in RNA-secure resuspension solution (Ambion Inc., Austin, Tex.), followed by removal of potential contaminating DNA by treatment with DNase I (DNA-Free Kit, Ambion Inc., Austin, Tex.). Equal aliquots (5 μg) of total RNA from each sample were quantified by spectrophotometry (wavelength 250 nm). Peak mRNA expression was quantified in duplicate by SYBR Green two-step, real-time RT-PCR. β-actin was used as the endogenous reference. Aliquoted RNA (40 ng) was subjected to first-strand complementary DNA (cDNA) synthesis using random hexamers (PE applied Biosystems, Foster City, Calif.) and Super Script II (Life Technologies, Rockville, Md.). Primers were taken from the literature or designed according to published sequences (Table 3). PCR reaction mixture was prepared using SYBR Green PCR Core Reagents (PE Applied Biosystems). Each sample was estimated in duplicate using the conditions recommended by the manufacturer. Real-time PCR data were plotted as the $\Delta R_n$ fluorescence signal versus the cycle number. An arbitrary threshold was set to the midlinear portion of the log $\Delta R_n$ cycle plot. The threshold cycle ($C_T$) is defined as the cycle number at which the $\Delta R_n$ crosses this threshold. Quantification of mRNA expression was normalized to β-actin and calculated relative to control using the comparative CT method.

TABLE 3

Primer Summary

| Primer | Source | Sequence 5' to 3' | Product size (bp) | SEQ. ID NO. |
|---|---|---|---|---|
| β-Actin | Overbergh et al. | AGAGGGAAATCGTGCGTGAC | 138 | 17 |
| | | CAATAGTGATGACCTGGCCGT | | 18 |
| IL-6 | GenBank M20572 | TCAATTCCAGAAACCGCTATGA | 78 | 19 |
| | | CACCAGCATCAGTCCCAAGA | | 20 |
| IL-1β | GenBank M15131 | CAGGTCGCTCAGGGTCACA | 75 | 21 |
| | | CAGAGGCAAGGAGGAAACACA | | 22 |
| IL-10 | GenBank M37897 | CACAAAGCAGCCTTGCAGAA | 68 | 23 |
| | | AGAGCAGGCAGCATAGCAGTG | | 24 |
| HO-1 | GenBank X13356 | CTCACTGGCAGGAAATCATCC | 67 | 25 |
| | | ACCTCGTGGAGACGCTTTACA | | 26 |
| iNOS | GenBank NM 010927 | GTGACGGCAAACATGACTTCAG | 74 | 27 |
| | | GCCATCGGGCATCTGGTA | | 28 |
| COX2 | GenBank NM 011198 | CTGGGACCCAACCCTCTGA | 71 | 29 |
| | | ACGGTGTGTACCACACGGC | | 30 |

To exclude PCR amplification of contaminating genomic DNA, RT-negative controls (samples containing RNA which was not reverse transcribed) were included in each PCR reaction. Melting curve analyses were performed for each reaction to ensure amplification of specific product. In addition, gel electrophoresis were performed for the primers to confirm the absence of non-specific bands and that the amplicons were of the correct size. PCR amplification efficiency of each target cDNA was measured by determining the colinearity of serial dilutions. Serial 3-fold dilutions of cDNA were performed in triplicate for all primers. Standard curves were generated by plotting $C_T$ values against relative input copy number to validate the primers. Slopes of the standard curves of −3.2±0.3 with correlation coefficients of 0.99 were considered to be acceptable, having corresponding efficiencies of 100±10%.

Analyses of Mediator Release from Intestinal Muscularis

Protein and Nitric Oxide Determinations. The small bowel of control and mice subjected to intestinal manipulation was removed under sterile conditions, 4 or 24 hours post-operatively, leaving the colon in situ. The small intestine was transferred to a beaker containing chilled Hanks balanced salt solution (Sigma, St. Louis, Mo.) with 200 U/ml penicillin G and 200 μg/ml streptomycin (HBSS), the lumen flushed, and the tissue transferred to a second beaker of HBSS. The muscularis was harvested as described above for real time RT-PCR. Tissues were maintained under sterile conditions at 3 to 5° C. throughout the harvesting procedure. Isolated muscularis was blotted onto sterile gauze, and the wet weight determined to obtain aliquots of 40 to 60 mg. Tissue aliquots were washed twice in HBSS, transferred to 35 mm well culture plates containing 3 ml of serum-free DMEM containing penicillin/streptomycin, and incubated for 24 hrs in a humidified 5% $CO_2$ incubator at 37° C. Pharmacological agents added to the culture medium were filter sterilized prior to use.

After the incubation period, the muscle tissue was pelleted, and aliquots of culture medium were frozen in liquid nitrogen and stored at −80° C. The levels of IL-6, IL-1β, $PGE_2$, and IL-10 proteins secreted into the culture medium were determined using commercially available ELISA kits (R&D Systems, Minneapolis, Minn.) according to the manufacturer's instructions. Nitric oxide (NO) released into the culture medium was estimated by measuring the stable end products of NO metabolism. Nitrate/nitrate levels were measured 24 hrs postoperatively using commercially available test kit (Oxford Biomedical Research, Oxford, Mich.) and quantified according to the manufacturer's directions. In this assay system, nitrate is reduced to nitrite using granulated cadmium, and the total nitrite concentration is subsequently measured using the Griess reaction. All measurements were normalized to tissue wet weight.

Inhaled CO Suppresses Development of Postoperative Ileus

General Observations

All animals recovered rapidly from surgery. No mortality or morbidity was associated with the surgical procedure or with the CO exposure regime. Although mice developed ileus, postoperative grooming and daily behavior was normal, with resumption of oral food and water intake occurring within a few hours after recovery from anesthesia.

Expression of HO-1

Figure 7A:
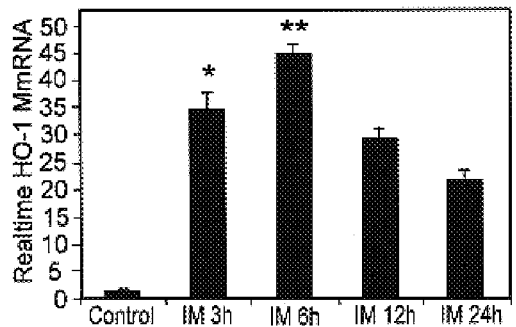
FIG. 7A is a bar graph illustrating the effect of intestinal manipulation (IM) on HO-1 expression in muscularis extracts as determined using real-time two-step RT-PCR analysis. Samples were analyzed 3 (IM 3 h), 6 (IM 6 h), 12 (IM 12 h), and 24 (IM 24 h) hours after laparotomy. Peak HO-1 expression occurred 3 to 6 hr postoperatively. Data represent mean fold increase relative to control ±SEM, n=6. * P=0.001; ** P=0.0001.
Figure 7B:
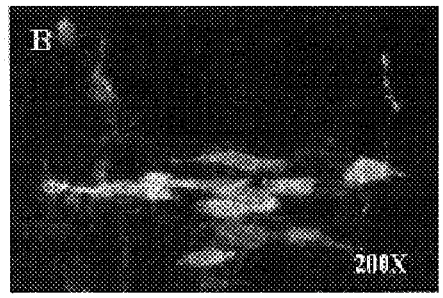
FIG. 7B is a picture of a muscularis whole mount illustrating HO-1-like immunoreactivity in polyrnorpholeukocytes infiltrating the muscularis following IM.

FIGS. 7A-7E are a bar graph and pictures illustrating expression of heme oxygenase (HO)-1 within the intestinal muscularis following surgical manipulation of the murine small bowel. To investigate a potential anti-inflammatory protective role for endogenous HO-1 products, alterations in HO-1 mRNA expression were determined by SYBR green real-time RT-PCR. FIG. 7A illustrates the expression patterns of HO-1 mRNA in the intestinal muscularis of unoperated control mice, and manipulated mice that were harvested 3, 6, 12, and 24 hr after laparotomy. HO-1 mRNA expression was significantly increased 35-fold relative to controls by 3 hr post-laparotomy, with peak expression occurring 6 hr post-operatively at 45-fold. Although levels of expression declined somewhat after 6 hr, expression remained elevated (22-fold) through the final time point measured at 24 hr post-operatively.

Figure 7C:
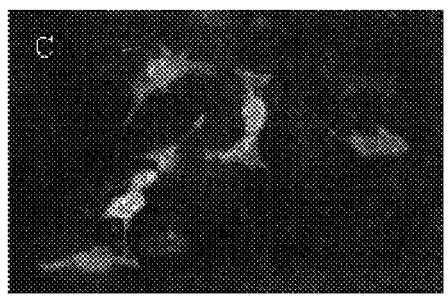
FIG. 7C is a picture of a muscularis whole mount illustrating HO-1-like immunoreactivity in macrophage-like cells infiltrating the muscularis following IM.
Figure 7D:
FIG. 7D is a picture of a muscularis whole mount illustrating HO-1-like immunoreactivity in granule-containing cells infiltrating the muscularis following IM. Sites of indistinct immunofluorescence in lower half of image are cells beneath the plane of focus.
Figure 7E:
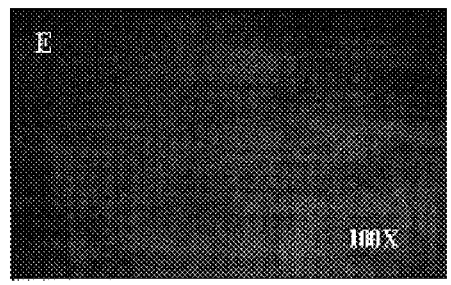
FIG. 7E is a picture of a muscularis whole mount illustrating lack of HO-1-like immunoreactivity in the muscularis of control animals.

Whether the increase in HO-1 mRNA resulted in protein expression within the intestinal muscularis after surgical manipulation was also investigated. HO-1 immunohistochemistry was performed on muscularis whole-mounts of mid-jejunum collected from unoperated mice and 24 hr post-operatively from mice subjected to surgical manipulation of the small intestine. In manipulated animals, HO-1 immunoreactivity was observed within large numbers of infiltrating polymorpholeukocytes (FIG. 7B), and in cells morphologically similar to macrophages (FIG. 7C). Occasionally, cells containing numerous cytoplasmic granules (granulocytes) were also found to exhibit intense HO-1 immunoreactivity (FIG. 7D). Faint HO-1 immunoreactivity was also observed in an uncharacterized population of cells dispersed within the muscle layers. HO-1 immunoreactivity was not detected in whole-mounts from unoperated control mice (FIG. 7E). Specificity of immunostaining for HO-1 was confirmed by omission of the primary antibodies (not shown).

Functional Studies

Figure 8A:
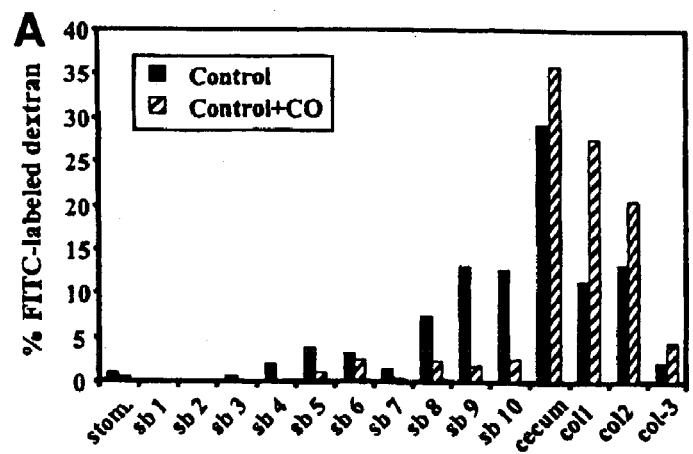
FIG. 8A is a bar graph illustrating the effects of inhaled CO (24 h exposure) on intestinal transit in mice not subjected to IM. stom=stomach; sb=small bowel; and col=colon. Solid bars=animals not exposed to CO; striped bars=animals exposed to CO. The majority of fluorescent signal is localized in the cecum and proximal colon.
Figure 8B:
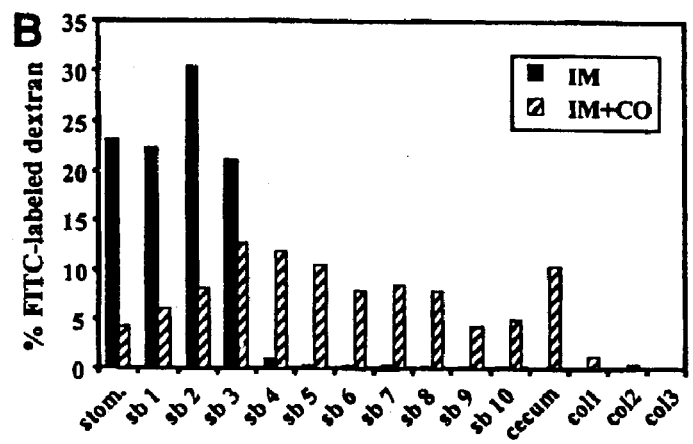
FIG. 8B is a bar graph illustrating the effects of inhaled CO (24 h exposure) on intestinal transit in mice subjected to IM. Stom=stomach; sb=small bowel; and col=colon. Solid bars=animals not exposed to CO; striped bars=animals exposed to CO. After IM, transit is significantly delayed. Inhalation of CO resulted in a more distal distribution of labeled dextran (IM-CO).
Figure 8C:
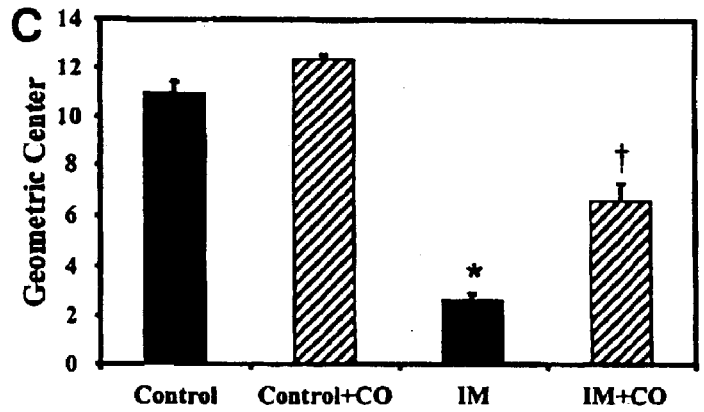
FIG. 8C is a bar graph illustrating the result of Geometric Center (GC) calculations. Higher numbers correspond to a more distal distribution of labeled dextran. Control=control animals; Control+CO=control animals exposed to CO; IM=animals subjected to IM; IM+CO=animals subjected to IM and exposed to CO. * In the IM group, GC was markedly impaired relative to controls, P<0.0001; n=6. † Inhalation of CO (IM+CO) resulted in a significant increase in GC relative to IM, P=0.001; n=6.

Intestinal transit was measured in controls and manipulated animals 24 hours postoperatively by evaluating the gastrointestinal distribution of orally fed fluorescein labeled dextran. FIGS. 8A-8C are bar graphs illustrating the results of transit studies determined from the distribution of non-absorbable fluorescein-labeled dextran 1.5 hours after oral administration. A median histogram of the fluorescence present in each bowel segment of naive control mice and CO treated mice is plotted in FIG. 8A. In naïve animals, the labeled dextran was distributed primarily within the terminal small bowel, cecum, and proximal colon 90 minutes after ingesting dextran. Inhalation treatment with CO (250 ppm) alone caused a slight insignificant shift in transit, with the label distributed predominantly within the cecum and colon. FIG. 8B compares the distribution of the fluorescent signal in mice that underwent intestinal manipulation, with or without CO treatment. After intestinal manipulation, the fluorescent signal was confined to the stomach and proximal 3 segments of small bowel. When animals were treated with CO, the label was distributed more distally throughout the gastrointestinal tract. Results from the calculations of the Geometric Center (GC) are summarized in FIG. 8C for statistical comparison. Higher values of GC indicate a more distal distribution of fluorescent signal, and correspond to a more rapid transit. The values in this figure demonstrate that CO accelerated intestinal transit in unoperated mice, but GC values did not achieve statistical significance. Additionally, as previously shown GC values show that transit is markedly slower after intestinal manipulation, but that this prolongation in transit was significantly improved in mice treated with CO inhalation.

Figure 9A:
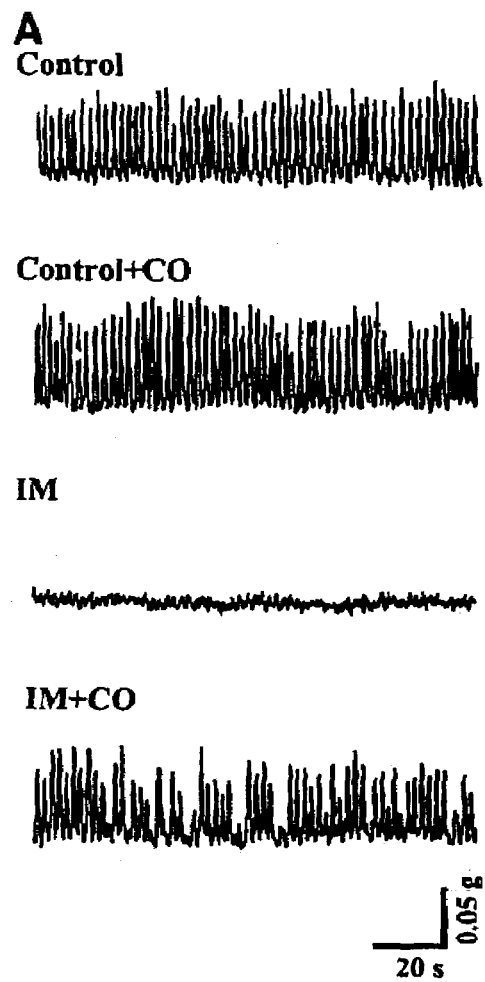
FIG. 9A are representative traces illustrating the effect of CO on spontaneous contractile activity. Control: Rythmic contractions characteristic of unoperated mice. Control+CO: Inhalation of carbon monoxide (CO) for 24 hr by control mice had no effect on spontaneous contractility. IM: Rythmic contractility is lost following surgical manipulation of the small intestine. IM+CO: Rythmicity is restored in manipulated animals treated with CO.
Figure 9B:
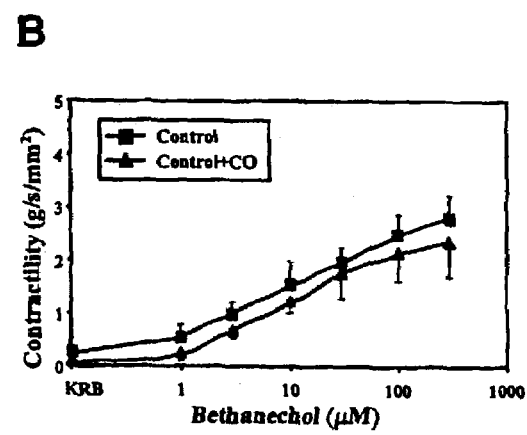
FIG. 9B is a line graph (dose-response curve) illustrating the effect of CO on the magnitude of tonic contractions in circular smooth muscle strips from animals not subjected to IM. The contractions were induced by exposure of the strips to increasing concentrations of bethanechol (0.1 to 300 µmol/L). Inhalation of CO by control animals had no effect on bethanechol-induced contractile activity. ■=control; ▼=Control+CO.
Figure 9C:
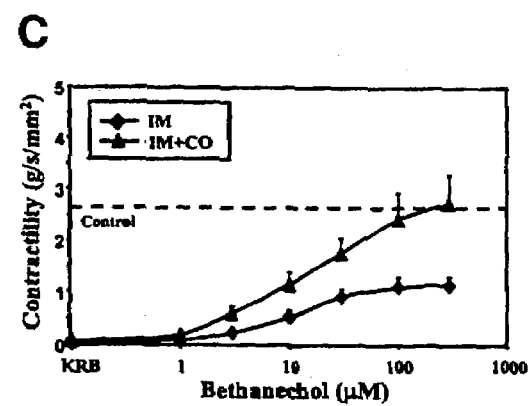
FIG. 9C is a line graph (dose-response curve) illustrating the effect of CO on the magnitude of tonic contractions in circular smooth muscle strips from animals subjected to IM. The contractions were induced by exposure of the strips to increasing concentrations of bethanechol (0.1 to 300 µmol/L). The capacity of circular muscle to contract in response to bethanechol was significantly impaired after IM. Inhalation of CO restored contractile activity to control levels (IM+CO). ■=IM; ▼=IM+CO.

The effects of CO on spontaneous and bethanechol stimulated small intestinal circular muscle contractility were investigated in vitro in organ bath experiments 24 hours after surgical manipulation of the intestine, a time point when ileus has been shown to be well established. FIGS. 9A-9C illustrate the mechanical activity of such small intestinal circular smooth muscle strips. FIG. 9A is a set of representative traces showing spontaneous contractility of intestinal circular muscle. Muscle strips from the small bowel of naive mice generated regular contractions (FIG. 9A; Control), and treatment with CO had no effect (FIG. 9A; Control+CO). After IM, spontaneous contractile activity was significantly suppressed (FIG. 9A; IM). However, in IM mice treated with CO, rythmicity was significantly improved (FIG. 9A; IM+CO).

The addition of the muscarinic agonist bethanechol (0.3 to 300 μM) to the superfusate elicited concentration-dependent tonic contractions. The area under the contraction curve was integrated and normalized to muscle strip surface area to obtain a measure of circular muscle contractility. FIGS. 9B and 9C are line graphs illustrating normalized contractility. In control mice, peak contractile force (3.5±0.7 g/s/mm$^2$) was generated in response to 100 μM bethanechol (FIG. 9B). CO alone had no effect on control contractions (3.2±0.5 g/s/mm$^2$). Surgical manipulation led to a reduction in contractile force throughout the dose-response curve compared with controls, achieving statistical significance at bethanechol concentrations greater than 10 μM (FIG. 9C). Peak contractile force generated with 100 μM bethanechol was reduced by 49% (1.7±0.4 g/s/mm$^2$) in these mice. Inhalation of CO (250 ppm) completely prevented the inhibitory effect of surgical manipulation (3.6±0.7 g/s/mm$^2$).

MPO Histochemistry

Figure 10:
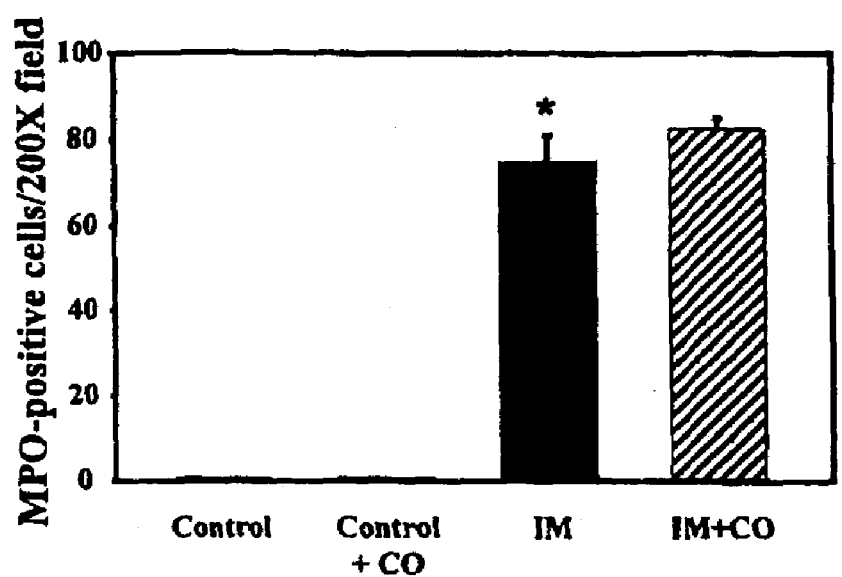
FIG. 10 is a bar graph illustrating the effect of inhalation of CO on the number of myeloperoxidase (MPO) positive leukocytes infiltrating the intestinal muscularis of control mice and after intestinal manipulation (IM). Control=control animals; Control+CO=control animals exposed to CO; IM=animals subjected to IM; IM+CO=animals subjected to IM and exposed to CO. Data are expressed as mean ±SEM. * P<0.0001; n=4.

Surgical manipulation of the small bowel typically causes a massive cellular inflammatory response within the muscularis. Hanker-Yates histochemistry for myeloperoxidase (MPO$^+$) activity was used to quantify leukocyte infiltrate in tissues from control and manipulated animals, with and without CO treatment. FIG. 10 is a histogram that summarizes the data on MPO$^+$ cells infiltrating the intestinal muscularis for the four experimental groups used in this study. Leukocytes were counted at a magnification of 200×. In control specimens that did not undergo surgery, MPO$^+$ cells were rare. Surgical anesthesia and intestinal manipulation resulted in a 250-fold increase in the number of MPO$^+$ cells infiltrating the muscularis at 24 hr. Interestingly, CO inhalation treatment had no effect on the magnitude of the leukocyte infiltrate in either group.

Pro-Inflammatory Cytokine Expression

Figure 11A:
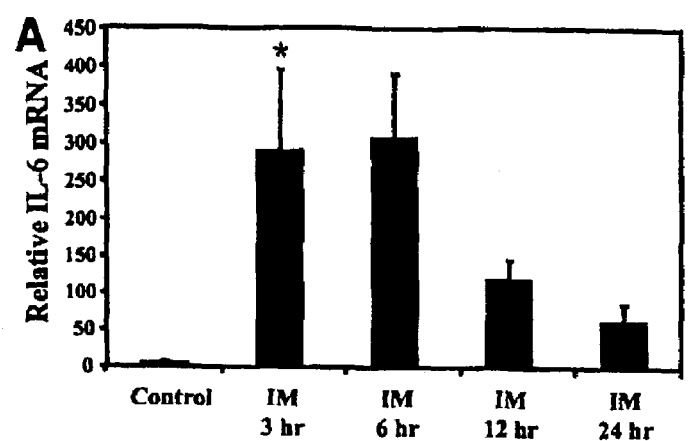
FIG. 11A is a bar graph illustrating the results of a real-time two-step RT-PCR analysis of the effects of surgical anesthesia and IM on the time course of IL-6 mRNA expression. Samples were analyzed at 3 (IM 3 h), 6 (IM 6 h), 12 (IM 12 h), and 24 (IM 24 h) hours. Expression peaked at 3 and 6 hours after surgery. Data are expressed as mean±SEM. * P<0.0001 relative to control.
Figure 11B:
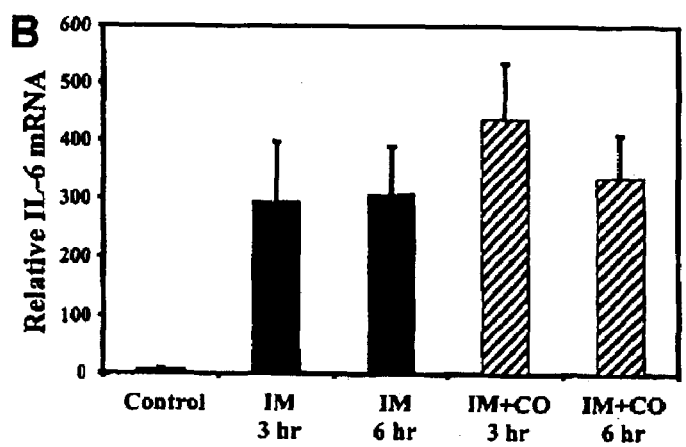
FIG. 11B is a bar graph illustrating the effect of CO inhalation on IL-6 mRNA expression at 3 (IM+CO 3 hr) and 6 (IM+CO 6 hr) hours after surgery. IM 3 hr and IM 6 h=IM control animals at 3 hr and 6 hr, respectively. Data are expressed as mean±SEM.
Figure 11C:
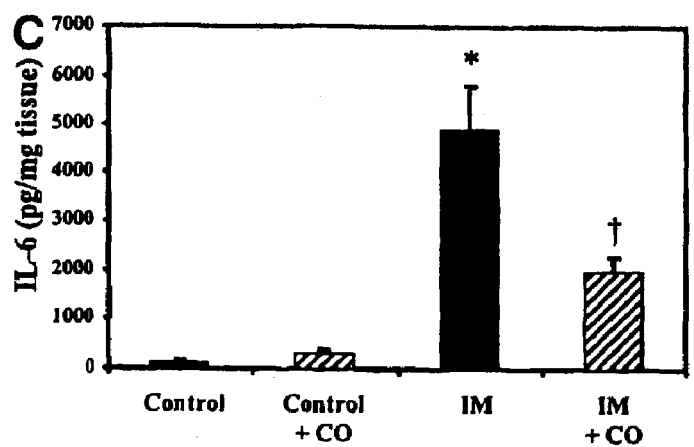
FIG. 11C is a bar graph illustrating the effect of CO inhalation on IL-6 protein release from muscularis extracts harvested 24 hr after surgery. IL-6 protein release was significantly attenuated by inhalation of CO. Control=control animals; Control+CO=control animals exposed to CO; IM=animals subjected to IM; IM+CO=animals subjected to IM and exposed to CO. Data are expressed as mean ±SEM. * P<0.0001 relative to control; and † P=0.001 relative to IM; n=6.

FIGS. 11A-11C are bar graphs illustrating the effects of inhaled CO on expression of IL-6. The figures show the time course of IL-6 gene expression after small bowel manipulation, and the effects of inhaled CO on IL-6 gene and protein expression. Time course analysis using real time RT-PCR showed that IL-6 mRNA was increased 300-fold relative to naive control mice, 3 and 6 hr postoperatively (FIG. 11A). Expression declined rapidly by 12 hr, falling to a 50-fold increase relative to controls at 24 hr. Inhalation of CO had no effect on manipulation-induced gene expression at the 3 and 6 hr time points (FIG. 11B). IL-6 protein release from the isolated muscularis was measured after incubation in cell culture medium (FIG. 11C). IL-6 protein was elevated massively 24 hr after intestinal manipulation, and in contrast to the PCR data protein release was reduced significantly by 70% in mice treated with CO.

Figure 12A:
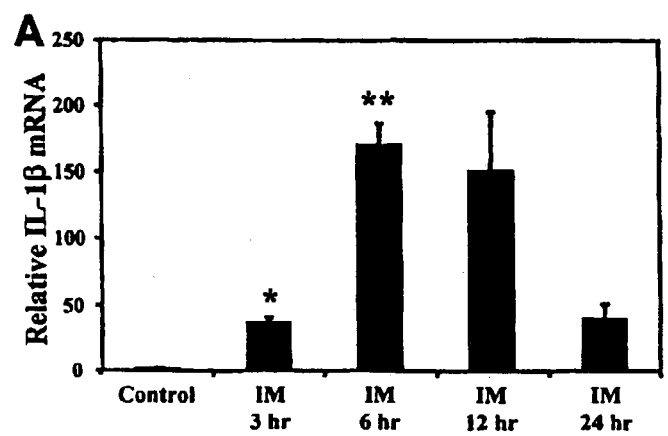
FIG. 12A is a bar graph illustrating the results of a real-time two-step RT-PCR analysis of the effects of surgical anesthesia and IM on the time course of IL-1β mRNA expression. mRNA expression after intestinal manipulation (IM). Samples were analyzed 3 (IM 3 h), 6 (IM 6 h), 12 (IM 12 h), and 24 (IM 24 h) hours. Peak expression occurred 6 hr postoperatively. Data are expressed as mean±SEM. * P=0.001 and ** P<0.0001 relative to control, n=6.
Figure 12B:
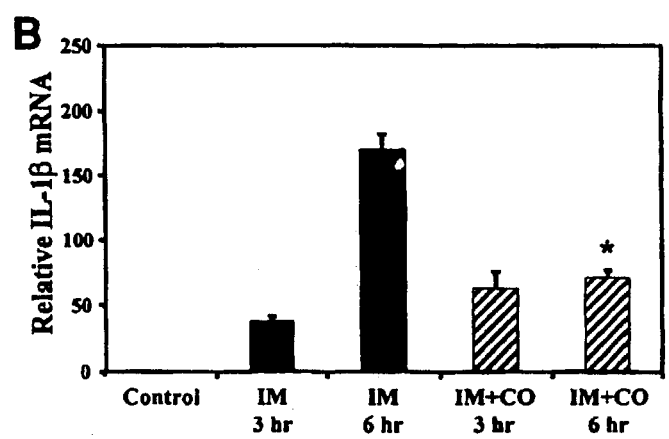
FIG. 12B is a bar graph illustrating the effect of CO inhalation on IL-1β mRNA expression at 3 (IM+CO 3 hr) and 6 (IM+CO 6 hr) hours after surgery. CO significantly inhibited peak IL-1β mRNA expression. IM 3 hr and IM 6 h=IM control animals at 3 hr and 6 hr, respectively. Data are expressed as mean±SEM. * P=0.001 relative to IM 6 hr, n=6.
Figure 12C:
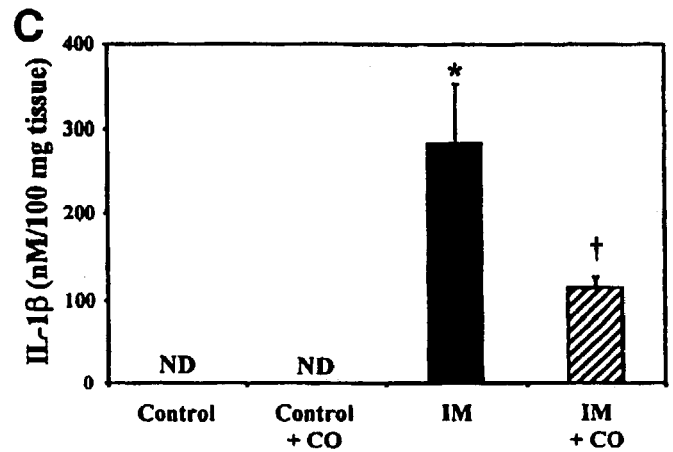
FIG. 12C is a bar graph illustrating the effect of CO inhalation on IL-1β protein release from muscularis extracts harvested 24 hr after surgery. IL-1β protein release was significantly attenuated by inhalation of CO. Control=control animals; Control+CO=control animals exposed to CO; IM=animals subjected to IM; IM+CO=animals subjected to IM and exposed to CO. Data are expressed as mean±SEM. ND=none detected. * P=0.001 relative to control; † P=0.001 relative to IM; n=6.

The proinflammatory cytokine IL-1β was also investigated. The time course of IL-1β gene expression is shown in FIGS. 12A-12B. Measurements of IL-1β were complicated by the observation that mRNA levels in muscularis extracts from naïve control mice and in control mice treated with CO were below the detection capabilities of the sequence analyzer. Thus, samples from manipulated mice harvested 6 hrs postoperatively were diluted serially and values of cycle threshold ($C_T$) were normalized to β-actin determined from undiluted samples. Control $\Delta C_T$ values were then calculated using the lowest concentration of IL-1β for which the $C_T$ decreased to within linear range. Changes in gene expression for the remaining experimental groups were then calculated relative to this control, and therefore are conservative in their estimation of the actual fold-increase. From these calculations, IL-1β mRNA expression in response to surgical anesthesia and intestinal manipulation was found to increase 38-fold relative to control, 3 hrs after surgery. Maximal expression occurred somewhat later than reported earlier for IL-6, reaching 170- and 150-fold at 6 and 12 hr postoperatively, and dropping again to 40-fold by 24 hr (FIG. 12A). In animals treated with CO, IL-1β expression at the 6 hr time point was reduced by 60% (FIG. 12B). IL-1β protein release from muscularis extracts harvested 24 hr after surgery was measured after a further 24 hours of incubation in cell culture medium (FIG. 12C). Correlating with the RT-PCR data, no IL-1β protein could be detected in either control group, whereas the concentration of protein produced by 100 mg of extracted tissue was elevated after intestinal manipulation. This response was reduced significantly by 60% in mice treated with CO inhalation.

Cyclooxygenase-2 and Inducible Nitric Oxide Synthase Expression

Activated resident macrophages and infiltrating leukocytes synthesize and release prostaglandins derived from the inducible isoform of cyclooxygenase, COX-2, and nitric oxide (NO) derived from the inducible form of nitric oxide synthase (iNOS), which have direct and potent inhibitory effects on the intestinal smooth muscle contractile apparatus.

Figures 13A, 13B, 13C:
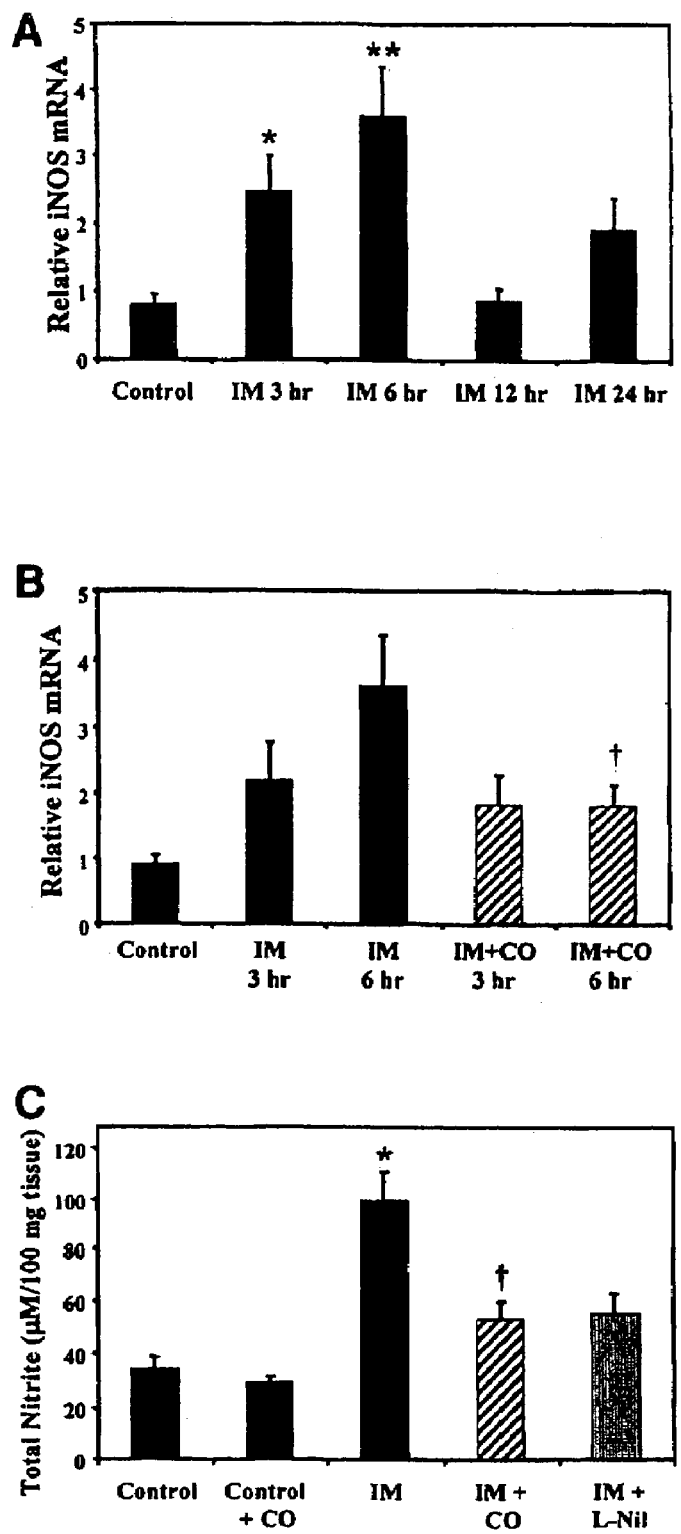
FIG. 13A is bar graph illustrating the results of a real-time two-step RT-PCR analysis of the effects of surgical anesthesia and IM on the time course of iNOS mRNA expression. Samples were analyzed at 3 (IM 3 h), 6 (IM 6 h), 12 (IM 12 h), and 24 (IM 24 h) hours. Peak expression occurred 6 hours after surgery. Data are expressed as mean±SEM. * P=0.001; ** P<0.0001 relative to control; n=6.
FIG. 13B is a bar graph illustrating the effect of CO inhalation on iNOS mRNA expression at 3 (IM+CO 3 hr) and 6 (IM+CO 6 hr) hours after surgery. IM 3 hr and IM 6 h =IM control animals at 3 hr and 6 hr, respectively. Data are expressed as mean±SEM. † P=0.001 relative to IM 6 hr; n=6.
FIG. 13C is a bar graph illustrating the effect of CO inhalation on total nitrite release from muscularis extracts harvested 24 hours after surgery. Total nitrite release was determined as an index of iNOS activity. Inhalation of CO significantly inhibited the surgically induced increase in nitrite release from manipulated muscularis. A similar reduction in nitrite was achieved by incubation of muscularis extracts in the presence of the selective iNOS inhibitor L-Nil (30 µM; IM+L-Nil). Control=control animals; Control+CO=control animals exposed to CO; IM=animals subjected to IM; IM+CO=animals subjected to IM and exposed to CO. * P=0.001 relative to control; † P=0.001 relative to IM; n=6. Data are expressed as mean±SEM.
Figures 14A, 14B, 14C, 14D:
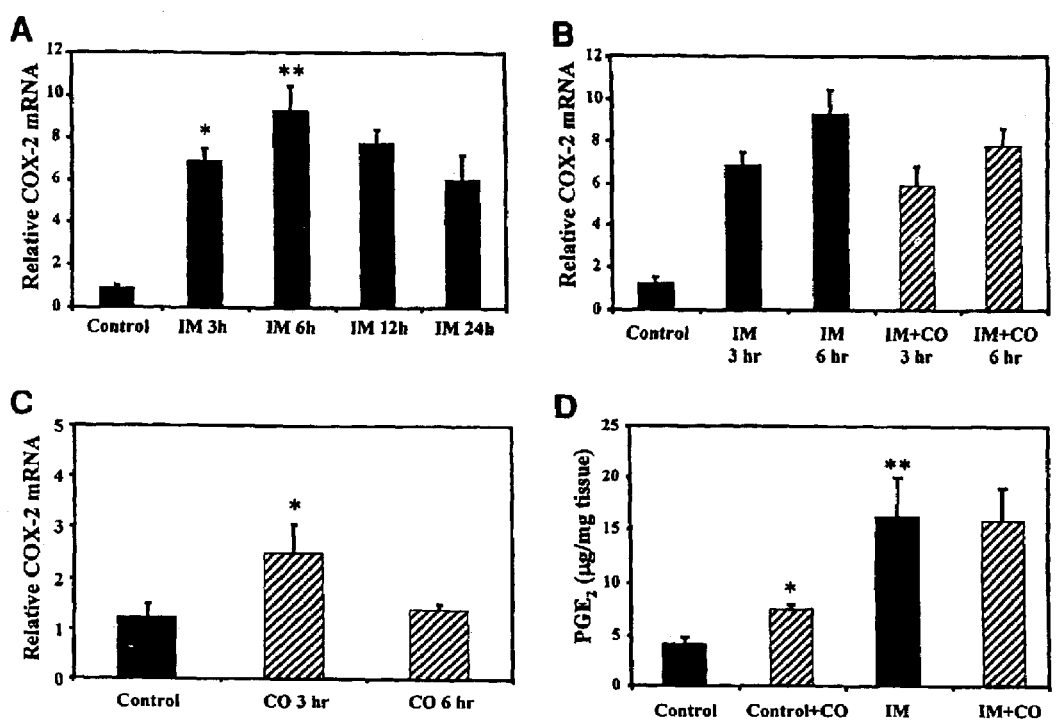
FIG. 14A is bar graph illustrating the results of a real-time two-step RT-PCR analysis of the effects of surgical anesthesia and IM on the time course of COX-2 mRNA expression. Samples were analyzed at 3 (IM 3 h), 6 (IM 6 h), 12 (IM 12 h), and 24 (IM 24 h) hours. Peak expression occurred 3-12 hr after surgery. Data are expressed as mean±SEM. * P=0.01; ** P =0.0001 relative to control; n=6.
FIG. 14B is a bar graph illustrating the effect of CO inhalation on COX-2 mRNA expression at 3 (IM+CO 3 hr) and 6 (IM+CO 6 hr) hours after surgery. IM 3 hr and IM 6 h=IM control animals at 3 hr and 6 hr, respectively. Data are expressed as mean±SEM.
FIG. 14C is a bar graph illustrating that CO inhalation by control animals significantly increased COX-2 mRNA expression 3 hr (CO 3 hr) post-treatment. CO 6 hr=expression at 6 hr post-treatment. Data are expressed as mean±SEM. * P=0.01.
FIG. 14D is a bar graph illustrating the effect of CO inhalation on $PGE_2$ protein release from muscularis extracts harvested 24 hours after surgery. $PGE_2$ protein release was determined as an index of COX-2 activity. Inhalation of CO significantly increased protein release from control muscularis but had no effect on the surgically induced increase in $PGE_2$ release from manipulated muscularis. Control=control animals; Control+CO=control animals exposed to CO; IM=animals subjected to IM; IM+CO=animals subjected to IM and exposed to CO. Data are expressed as mean±SEM. * P=0.01 and ** P=0.0001 relative to control; n=6.

The temporal profile for iNOS expression following manipulation is illustrated in FIGS. 13A-13C. Time course analysis showed that gene expression was increased significantly 3 and 6 hr after small bowel manipulation (FIG. 13B). Peak expression at 6 hr was reduced by 60% in animals treated with CO (FIG. 14B). Exposure of naive mice to CO had no effect on iNOS expression (fold increase: Control, 1.06±0.18; CO 3 hr, 1.04±0.19; CO 6 hr, 1.26±0.19) Total nitrite released into the culture medium from muscularis extracts harvested 24 hr postoperatively, was measured as an estimate of NO production (FIG. 13C). As predicted by the PCR data, nitrite measurements were significantly increased after intestinal manipulation and this increase was reduced by 75% by treating mice with CO. A similar attenuation of the response was achieved by incubating the muscularis extracts in the presence of the selective iNOS inhibitor, L-Nil (50 μM), indicating that iNOS was the source of the surgically induced increase in NO production.

FIGS. 14A-14D are bar graphs illustrating the effects of inhalation of CO on the expression of COX-2. The figures show the temporal profile of IM induced COX-2 expression. Time course analysis showed that COX-2 gene expression was increased 8-10 fold, 3 to 6 hr after surgery, and remained elevated through 24 hr (FIG. 14A). CO treatment had no effect on gene expression at the 3 or 6 hr time points (FIG. 14B). The CO inhalation itself by unoperated control mice resulted in a relatively small 2.5-fold induction of COX-2 message 3 hr postoperatively (FIG. 14C). PGE$_2$ release from muscularis extracts harvested 24 hr after surgery was measured as a marker of COX-2 activity (FIG. 14D). Consistent with the PCR data, both inhalation of CO alone and intestinal manipulation caused significant increases in PGE$_2$ release. Specifically concerning PGE$_2$, treatment of manipulated mice with CO had no effect on IM-induced release of this prostanoid.

Anti-Inflammatory Gene Expression

Figures 15A, 15B, 15C:
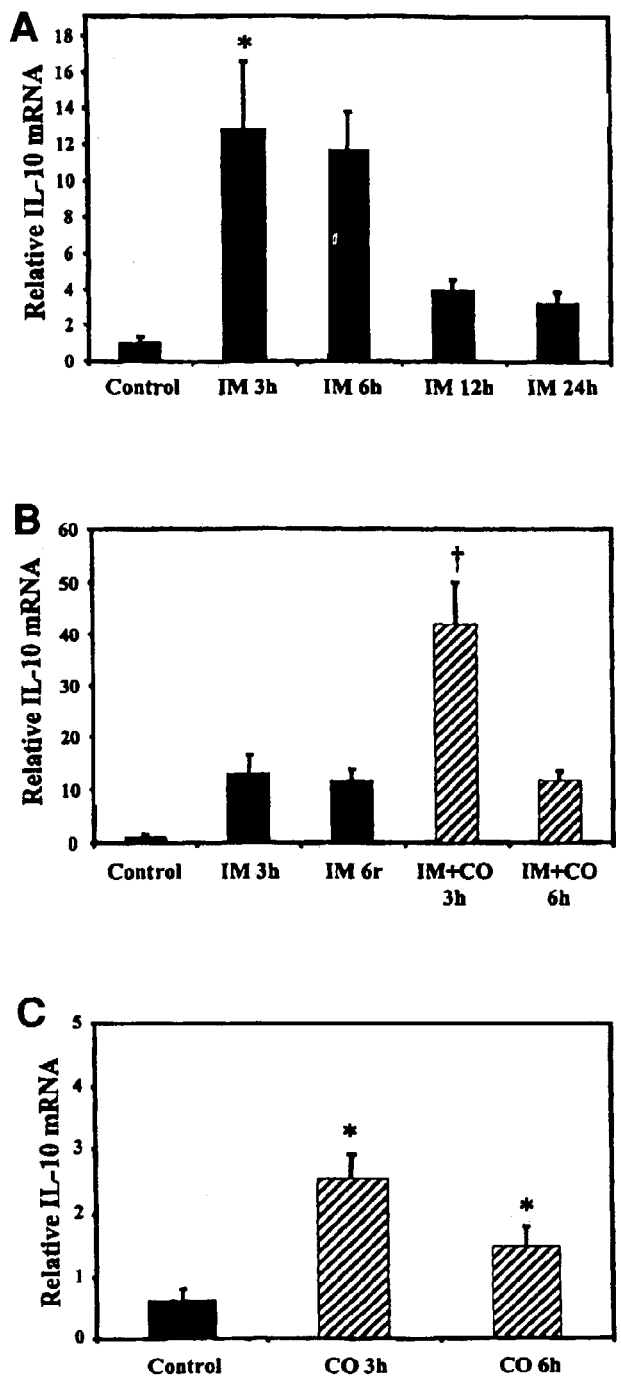
FIG. 15A is a bar graph illustrating the results of a real-time two-step RT-PCR analysis of the effects of surgical anesthesia and IM on the time course of IL-10 mRNA expression. Samples were analyzed at 3 (IM 3 h), 6 (IM 6 h), 12 (IM 12 h), and 24 (IM 24 h) hours. Peak expression occurred 3 to 6 hr after surgery. Data are expressed as mean±SEM. * $P \leq 0.001$ relative to control; n=6.
FIG. 15B is a bar graph illustrating the effect of CO inhalation on IL-10 mRNA expression at 3 (IM+CO 3 hr) and 6 (IM+CO 6 hr) hours after surgery. Inhalation of CO increased IL-10 message at 3 hr but not 6 hr after surgery. IM 3 hr and IM 6 h=IM control animals at 3 hr and 6 hr, respectively. Data are expressed as mean±SEM. † p=0.001 relative to IM 3 hr; n=6.
FIG. 15C is a bar graph illustrating that CO inhalation by control animals significantly increased IL-10 mRNA expression 3 (CO 3 h) and 6 hr (CO 6 h) after treatment. Data are expressed as mean±SEM. * $P \leq 0.001$ relative to control; n=6.

IL-10 is a pleiotropic cytokine that has important protective and anti-inflammatory effects in the gastrointestinal tract. FIGS. 15A-15C illustrate the effects of CO inhalation of on IL-10 expression. The figures show the profile of IL-10 expression over time. Gene expression underwent a 12-fold increase relative to control in response to intestinal manipulation, 3 and 6 hrs after surgery. Expression dropped thereafter, but remained elevated through 24 hr at approximately 4-fold relative to control expression (FIG. 15A). In CO treated manipulated animals at the 3 hr time point, IL-10 gene expression was increased to 43-fold relative to controls, a response 300% greater than that of manipulation alone (FIG. 15B). In control mice, CO inhalation alone was sufficient to induce a significant increase in IL-10 expression (FIG. 15C).

Figures 16A, 16B:
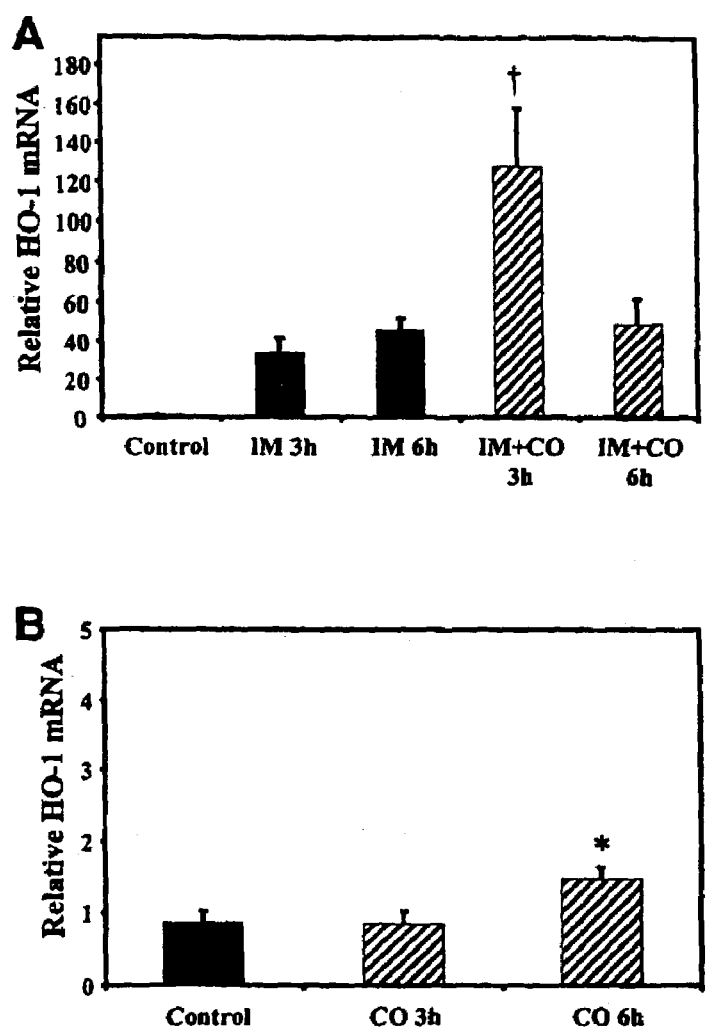
FIG. 16A is a bar graph illustrating the results of a real-time two-step RT-PCR analysis of the effects of surgical anesthesia and IM on the time course of HO-1 mRNA expression 3 and 6 hr after surgery (IM). Inhalation of CO significantly increased HO-1 mRNA expression at 3 hr (IM+CO 3 hr) but not 6 hr (IM+CO 6 hr) postoperatively. IM 3 hr and IM 6 h=IM control animals at 3 hr and 6 hr, respectively. † P<0.001 relative to IM 3 hr; n=6.
FIG. 16B is a bar graph illustrating the effect of CO inhalation on expression of HO-1 mRNA 3 hr (CO 3 h) and 6 hr (CO 6 h) after treatment. CO inhalation by control animals increased HO-1 mRNA expression 6 hr after treatment. * P<0.05 relative to control; n=6.

The effect of inhaled CO on HO-1 gene expression was also evaluated. FIGS. 16A-16B illustrate the effect of CO inhalation on HO-1 expression. FIG. 16A compares IM-induced gene expression 3 and 6 hr after surgery (see FIG. 7D), with that achieved in manipulated mice treated with CO. Inhalation of CO also increased HO-1 gene expression 3 hr postoperatively to a level 300% greater than that of manipulation alone (FIG. 16B). In this case, inhalation of CO alone by unoperated control mice induced a small, though significant, increase in HO-1 gene expression, but only at the 6 hr time point.

The present example provides both in vivo and in vitro evidence that the inhalation of a low concentration of CO (250 ppm) significantly attenuates the intestinal dysmotility that characterizes postoperative ileus. The data show that CO can act at the level of gene and protein expression to selectively modulate specific elements of both pro-inflammatory and anti-inflammatory pathways leading to a significant improvement in intestinal function.

Postoperative ileus is currently a virtually inevitable consequence of abdominal surgical procedures, and can range from short-term atony to severe paralytic ileus that can persist for days. Paralytic ileus is characterized by intestinal stasis, bacterial overgrowth, and fluid electrolyte imbalances, resulting in significant morbidity and often mortality. Exposure of mice to CO by inhalation improved the manipulation induced suppression in spontaneous circular smooth muscle contractility, restored the muscle's capacity to contract in response to cholinergic agonists, and significantly attenuated the impairment in intestinal transit. This improvement in overall contractile function was achieved without a significant reduction in the inflammatory cell infiltrate, suggesting that CO acted on elements of the inflammatory cascade other than those associated with leukocyte recruitment. In order to assess the effect of CO on the inflammatory cascade, pro- and anti-inflammatory mediator gene expression was assessed by real time RT-PCR.

Increased levels of the pro-inflammatory cytokines IL-6 and IL-1 are consistently expressed during acute and chronic intestinal inflammation in humans and animals, including postoperative ileus. IL-6 activates a variety of cell types to induce synthesis of chemoattractants and adhesion molecules, and thus plays a central role in initiating leukocyte recruitment and extravasation into the intestinal muscularis. In this example, inhalation of CO did not alter the early surgically induced increase in IL-6 gene expression measured 3 and 6 hr postoperatively, a finding consistent with its lack of effect on the magnitude of the inflammatory cell infiltrate. However, IL-6 protein release from the isolated intestinal muscularis determined 24 hr postoperatively was reduced by 60% from 5000 pg/ml to 2000 pg/ml in mice treated with CO, suggesting that CO has a post-transcriptional effect on IL-6 expression. This sustained level of protein release was still markedly elevated relative to naive controls (150 pg/ml), making it difficult to estimate what effect this may have on IL-6 proinflammatory signaling. Recent studies, however, have shown that IL-6 may also have important anti-inflammatory properties, suggesting that continued expression of IL-6 is necessary for the induction of certain protective pathways. These potentially include the ability to inhibit the production of TNF-α, IL-1β and macrophage inflammatory protein-2, and to increase levels of IL-1 receptor antagonist and TNF-soluble receptor in vitro. Thus, the dampening of IL-6 mediated pro-inflammatory pathways, as well as the initiation of IL-6 mediated anti-inflammatory pathways at later stages in the inflammatory cascade, may contribute to the improved intestinal contractility seen 24 hr postoperatively.

The role played by IL-1β in postoperative ileus has been less well characterized; however, endogenous IL-1β has been shown to inhibit the contractile responses of rat intestinal smooth muscle to cholinergic agonists and to electrical stimulation, suggesting that it exerts its inhibitory effects by altering neuronal pathways. In addition, immuno-neutralization of IL-1 activity greatly diminished the severity of disease in a murine model of colitis, indicating that this cytokine also plays an important initiating role in intestinal inflammation. In manipulated mice treated with CO, IL-1β gene expression was markedly reduced, with a 75% reduction in surgically induced gene expression at 6 hr after surgery, and a corresponding reduction in protein expression measured at 24 hr. Thus, it would be expected that pro-inflammatory activities of IL-1β, as well as its potential inhibitory effects on the neuromuscular apparatus, would be markedly attenuated. Taken together, these findings suggest that the protective effects of CO inhalation occur, at least in part, by a mechanism that targets selective elements within the IL-6 and IL-1β mediated pro-inflammatory cascade that are independent of leukocyte recruitment or that occur after leukocyte recruitment has been initiated fully.

Although the number of infiltrating leukocytes was not altered in CO treated mice, the cytokine data indicated that there was a CO-dependent functional inhibition of cytokines that are generated classically by leukocytes. Therefore, the modulation of the leukocyte-derived kinetically active smooth muscle mediators NO and $PGE_2$ as additional targets for inhibition by CO was investigated. It has been shown that prostanoids produced by COX-2 and nitric oxide produced by iNOS have potent inhibitory effects on intestinal smooth muscle contractility, and that inhibition of the COX-2 enzyme or the selective knockout of the leukocyte derived iNOS gene markedly increases resistance to the development of postoperative ileus. In the present example, examination of iNOS and COX-2 gene expression revealed that both were significantly elevated following intestinal manipulation. Surgically induced increases in both iNOS gene expression and NO production were reduced by approximately 75% in CO treated animals, suggesting that CO could act at the level of gene transcription to modulate iNOS expression. It has also been shown in vitro that iNOS activity, as well as the endothelial and neuronal isoforms of NOS, can be directly inhibited by CO, possibly through the binding of CO to heme moieties present on NOS proteins. Taken together, a reduction in NO release as a result of decreased gene expression and/or enzyme activity would be expected to contribute significantly to the improved intestinal function induced by inhalation of CO. In contrast to iNOS, CO inhalation had no effect on surgically induced COX-2 mRNA expression or $PGE_2$ release, as measured in culture media of the incubated muscularis harvested 24 h after surgery. Interestingly, CO inhalation by naive mice resulted in a 2.5-fold increase in COX-2 mRNA expression 3 hr after surgery with a corresponding increase in $PGE_2$ release after 24 hr. Induction of COX-2 by CO has not been reported previously, and the functional consequence of this increased activity is unknown. CO-treated control mice exhibited no functional impairment or elevation of pro-inflammatory mediators suggesting that, in this instance, the induction of COX-2 does not act in a pro-inflammatory capacity.

One of the dramatic effects of CO inhalation was on the expression of genes linked to anti-inflammatory pathways: IL-10 and HO-1. While both genes were induced after intestinal manipulation, expression was increased by 300% in CO treated manipulated animals. This increase was observed at the 3 hr postoperative time point but not the 6 hr time point suggesting that CO exposure resulted in the early induction of these genes, a concept supported by results showing that inhalation of CO alone by naïve animals resulted in significant induction of IL-10 and HO-1. The role played by these mediators in postoperative ileus has not been characterized previously. However, IL-10 is a pleiotropic cytokine with a wide spectrum of biological effects on lymphoid and myeloid cells. One of its known functions is its ability to inhibit the production of pro-inflammatory mediators; including the production of tumor necrosis factor-alpha (TNFα) IL-6, IL-1, granulocyte-macrophage colony stimulating factor, and the generation of nitric oxide by activated monocytes/macrophage. Recently, IL-10 was found to inhibit the production of NO by LPS stimulated murine macrophages, both by antagonizing the cellular uptake of L-arginine as well as the catalytic activity of iNOS itself, thereby potentially contributing to the attenuation of the inhibitory effects of NO on intestinal smooth muscle. In addition, it has become increasingly apparent that induction of the HO-1 mediated pathway has important anti-inflammatory and cytoprotective effects under a variety of acute and chronic inflammatory conditions. There is now evidence suggesting that the expression of these two mediators is inter-related. Published findings have shown that exposure to CO augments IL-10 gene expression and protein release from LPS-stimulated macrophages. More recently, endogenous IL-10 was found to induce HO-1 in murine macrophages, and HO-1 induction was required for the inhibitory effects of IL-10 on lipopolysaccharide induced TNF-α production. Early induction of HO-1 could result in increased endogenous CO output that would be expected to contribute to the effects of the exogenously applied gas. In addition, HO-1 activity has cytoprotective and anti-oxidant properties that have been attributed to free radical scavenging through redox cycling of biliverdin and bilirubin. Therefore, increased IL-10 production and enhanced activity of HO-1 would act in concert to dampen the inflammatory cascade early in its development by down regulating pro-inflammatory mediator expression, enhancing the tissue availability of CO and providing protection from free radical stress.

In summary, the data presented here suggest that the protective effects of CO inhalation occur by targeting selective elements within pro- and anti-inflammatory pathways. CO appears to act at the level of both gene and protein expression leading to the induction of IL-10 and HO-1, down regulation of IL-1β, and inhibition of iNOS. Together these effects result in the modulation of the surgically induced inflammatory responses within the intestinal muscularis, leading to improved postoperative function.

EXAMPLE 3

CO Suppresses the Development of Ileus Associated With Surgical Manipulation of the Small Intestine in the Mouse and the Pig Ileus was induced in mice by gentle manipulation of the small intestine. An incision was made to expose the abdominal cavity of the mouse, and bowel manipulation was performed by gentle poking and prodding of the small intestine (see, e.g., Schwarz et al., Gastroenterology 121(6):1354-1357 (2001)). The incision was subsequently closed, and analyses were performed 24 hours later. Mice were exposed to CO by inhalation (250 and 500 ppm) for 1 hour immediately prior to intestinal manipulation and during the entire 24-hour recovery period. Intestinal contractility was assessed in vitro by measuring circular muscle strip contractions in response to bethanechol (0.3-300 µM) and in vivo by determining intestinal transit from the distribution of orally-fed, fluorescein-labeled dextran and calculating geometric center as described in Example 1 above. HO-1 and IL-10 mRNA expression were determined by SYBR green real time RT-PCR from extracts of muscularis externae, as described in Example 1 above. Release of nitric oxide (NO), a potent inhibitor of smooth muscle contractility, was estimated by measuring serum total nitrite, also described in Example 1 above.

Peak contractile force generated in response to bethanechol (100 µM) was significantly reduced by IM ($1.1\pm0.2$ g/s/mm$^2$) compared to controls ($2.2\pm0.5$ g/s/mm$^2$). IM-induced suppression of contractility was prevented in IM+CO mice ($1.9\pm0.5$ g/s/mm$^2$). Intestinal transit also was improved in CO-treated mice (geometric center: control=$11.0\pm0.5$, IM=$2.7\pm0.2$, IM+CO=$6.3\pm0.8$). RT-PCR data showed that IM induced significant increases in peak HO-1 expression (45-fold) at 6 hrs, and IL-6 (300-fold) and IL-10 (13-fold) expression 3 hrs, after IM versus controls. In IM-CO mice, HO-1 expression peaked earlier, 3 hrs post-IM, at a higher expression level (150-fold) versus controls. IL-10 expression at 3 hr also was higher in IM-CO mice (35-fold). Serum nitrite was increased after IM ($18.3\pm3.6$ µM) versus control ($2.4\pm1.0$ µM), and reduced after IM-CO ($6.0\pm1.6$ µM).

Therefore, CO attenuates surgically induced intestinal dysmotility, in vitro and in vivo, via mechanisms that may involve induction of the anti-inflammatory cytokine IL-10 and decreased NO production. The early induction of HO-1 (300% increase in expression over IM alone) would increase the availability of CO, enhancing its anti-inflammatory effects.

Similar experiments were performed in a pig model. Ileus was induced by mild manipulation of the small intestine (IM). Pigs were exposed to CO (250 ppm) or air (controls) for a period of 3 hr prior to IM. Gastrointestinal function was assessed in vivo by observing intestinal transit of steel ball bearings placed within the small intestine. CO was found to improve intestinal transit following intestinal manipulation.

EXAMPLE 4

Pre-Treatment With Low Concentrations of CO (250 to 75 ppm) for Three Hours Prior to Laparotomy Protects Against Development of Postoperative Ileus.

This example demonstrates that low concentrations of CO delivered for short periods of time are protective against development of postoperative ileus.

Ileus was induced by mild manipulation of the small intestine (IM). Rats were exposed to decreasing concentrations of CO (250, 125, 75, 30 ppm) in air for a period of either 1 hr or 3 hr prior to laparotomy (n=6). Results were compared to those obtained using previously established protocols of exposure to CO at 250 ppm 1 hr before and for 24 hr after laparotomy. Gastrointestinal function was assessed in vivo by determining intestinal transit from the distribution throughout the GI tract of orally fed fluorescein labeled dextran. The median distribution of the labeled dextran was determined for statistical comparison by calculating the geometric center (GC).

Geometric center was significantly decreased in rats that underwent surgical manipulation compared to unoperated controls (GC: control=9.8±0.2, IM=5.8±0.4) indicating a significant slowing of intestinal transit. Although exposure of unoperated rats to 250 ppm for 24 hr resulted in a slight delay in intestinal transit (GC: 8.8±0.4), a 1 hr pretreatment followed by 24 hr post-treatment with 250 ppm CO resulted in a significant improvement in intestinal transit in rats that underwent surgical manipulation (GC: 8.2±0.4). Pretreatment of manipulated rats with 250 ppm for 1 hr only prior to surgery was less effective in preventing surgically induced inhibition of transit (GC: 7.2±0.3), whereas pretreatment for 3 hr produced an effect equivalent to that achieved with 24 hr treatment (GC: 8.6±0.3). A similar improvement was obtained by pre-treating with concentrations as low as 125 and 75 ppm (GC: 8.6±0.4 and 8.8±0.1, respectively). This protective effect declined when the CO concentration was further reduced to 30 ppm (GC: 7.0±0.2).

This example demonstrates that prolonged exposure to CO is not required to derive full benefit of protection from the development of postoperative ileus. The incorporation of low concentrations of CO into anesthesia gases during the pre-operative period may provide a minimally invasive technique that would aid in reducing ileus in susceptible patients, thus hastening postoperative recovery and reducing hospital stay.

EXAMPLE 5

Protocols for the Treatment of Ileus.

The following example illustrates protocols for use in treating patients before, during, and/or after surgical procedures, e.g., a transplant (e.g., SITx) or non-transplant procedures (e.g., a procedure from which ileus can result). The example includes protocols for treating ileus, e.g., ileus resulting from transplant and non-transplant procedures, and additional protocols for treating donors, the gastrointestinal tract or a portion thereof, e.g., a small intestine, and recipients with CO in a transplantation procedure. Any one or more of the following procedures may be used in a given surgical procedure.

Treatment of Patients

CO can be administered systemically or locally to a patient prior to, during, and/or after a surgical procedure is performed in the patient or after a patient is diagnosed with ileus (e.g., ileus resulting from surgery or resulting from conditions not involving surgery). Patients can inhale CO at concentrations ranging from 10 ppm to 1000 ppm, e.g., about 100 ppm to about 800 ppm, about 150 ppm to about 600 ppm, or about 200 ppm to about 500 ppm. Preferred concentrations include, e.g., about 30 ppm, 50 ppm, 75 ppm, 100 ppm, 125 ppm, 200 ppm, 250 ppm, 500 ppm, 750 ppm, or about 1000 ppm. CO can be administered to the patient, intermittently or continuously, starting 0 to 20 days before the procedure is performed, e.g., starting at least about 30 minutes, e.g., about 1, 2, 3, 5, 7, or 10 hours, or about 1, 2, 4, 6, 8, 10, 12, 14, 18, or 20 days, or greater than 20 days, before the procedure. Alternatively or in addition, CO can be administered to the patient during the procedure, e.g., by inhalation and/or topical administration. Alternatively or in addition, CO can be administered to the patient after the procedure, e.g., starting immediately after completion of the procedure, and continuing for about 1, 2, 3, 5, 7, or 10 hours, or about 1, 2, 5, 8, 10, 20, 30, 50, or 60 days, indefinitely, or until normal bowel motility is restored, after the completion of the procedure.

Transplant Procedures

Treatment of a Donor

Prior to harvesting an organ or portion thereof, the donor can be treated with inhaled carbon monoxide (250 ppm) for one hour. Treatment can be administered at doses varying from 10 ppm to 1000 ppm for times varying from one hour to six hours, or for the entire period from the moment when it becomes possible to treat a brain-dead (cadaver) donor to the time the organ is removed. For a human donor, treatment should start as soon as possible following the declaration that brain death is present. In some applications, it may be desirable to begin treatment before brain death.

For non-human animals (e.g., pigs) to be used as xenotransplantation donors, the live donor animal can be treated with relatively high levels of inhaled carbon monoxide, as desired, so long as the carboxyhemoglobin so produced does not compromise the viability and function of the organ to be transplanted. For example, one could use levels greater than 500 ppm (e.g., 1000 ppm or higher, and up to 10,000 ppm, particularly for brief times).

Treatment of the Organ in Situ

Before an organ is harvested from a donor, it can be flushed or perfused with a solution, e.g., a buffer or medium, while it is still in the donor. The intent is to flush the organ with a solution saturated with carbon monoxide and maintained in a carbon monoxide atmosphere so that the carbon monoxide content remains at saturation. Flushing can take place for a time period of at least 10 minutes, e.g., 1 hour, several hours, or longer. The solution should ideally deliver the highest concentration of carbon monoxide possible to the cells of the organ.

Treatment of the Organ ex vivo

An organ, such as a small intestine, can be preserved in a medium that includes carbon monoxide from the time it is removed from the donor to the time it is transplanted to the recipient. This can be performed by maintaining the organ in the medium comprising CO, or by perfusing it with such a medium. Since this occurs ex vivo rather than in an animal, very high concentrations of CO gas can be used (e.g., 10,000 ppm) to keep the medium saturated with CO.

Treatment of a Recipient

Treatment of the recipient with CO can begin on the day of transplantation at least 30 minutes before surgery begins. Alternatively, it could begin at least 30 minutes before re-perfusion of the organ in the recipient. It can be continued for at least 30 minutes, e.g., 1 hour. Carbon monoxide doses between 10 ppm and 3000 ppm can be delivered for varying times, e.g., minutes or hours, and can be administered on the day of and on days following transplantation. For example, the patient can inhale a concentration of carbon monoxide, e.g., 3000 ppm, for three consecutive 10 second breath holds. Alternatively, a lower concentration of the gas can be delivered intermittently or constantly, for a longer period of time, with regular breathing rather than breath holding. Carboxyhemoglobin concentrations can be utilized as a guide for appropriate administration of carbon monoxide to a patient. Usually, treatments for recipients should not raise carboxyhemoglobin levels above those considered to pose an acceptable risk for a patient in need of a transplant.

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating ileus in a patient, the method comprising:
   identifying a patient suffering from ileus; and
   administering to the patient a therapeutically effective amount of a gaseous composition comprising carbon monoxide at a concentration of about 10 ppm to about 10,000 ppm, wherein the patient inhales the gaseous composition.

2. The method of claim 1, wherein the ileus is ileus of the small intestine.

3. The method of claim 1, wherein the ileus is ileus of the colon.

4. The method of claim 1, wherein the ileus is ileus of the stomach.

5. The method of claim 1, wherein the ileus is post-surgical ileus.

6. The method of claim 1, wherein the ileus is post-partum ileus.

7. A method of treating ileus in a patient, the method comprising:
   identifying a patient suffering from or at risk for ileus caused by an abdominal surgery selected from the group consisting of: surgery of the urogenital system; surgery of the digestive system; surgery of the lymphatic system; surgery of the respiratory system; surgery of the diaphragm; surgery to treat cancer; endometrial surgery; and orthopedic surgery; and administering to the patient a therapeutically effective amount of a gaseous composition comprising carbon monoxide at a concentration of about 10 ppm to about 10,000 ppm, wherein the patient inhales the gaseous composition.

8. The method of claim 7, wherein the ileus is ileus of the small intestine.

9. The method of claim 7, wherein the ileus is ileus of the colon.

10. A method of treating ileus in a patient, the method comprising:
identifying a patient suffering from or at risk for ileus not caused by surgery; and
administering to the patient a therapeutically effective amount of a gaseous composition comprising carbon monoxide at a concentration of about 10 ppm to about 10,000 ppm, wherein the patient inhales the gaseous composition.

11. A method of treating ileus in a patient, comprising:
(a) providing a vessel containing a pressurized gas comprising carbon monoxide gas;
(b) identifying a patient suffering from ileus;
(c) releasing the pressurized gas from the vessel, to form an atmosphere comprising carbon monoxide gas at a concentration of about 10 ppm to about 10,000 ppm; and
(d) exposing the patient to the atmosphere, wherein the amount of carbon monoxide in the atmosphere is a therapeutically effective amount sufficient to treat ileus in the patient and wherein the patient inhales the atmosphere.

12. The method of claim 1, wherein the composition comprises carbon monoxide gas at a concentration of at least 50 ppm.

13. The method of claim 1, wherein the pharmaceutical composition comprises carbon monoxide gas at a concentration of at least 100 ppm.

14. The method of claim 1, wherein the pharmaceutical composition comprises carbon monoxide gas at a concentration of at least 250 ppm.

15. The method of claim 1, wherein the pharmaceutical composition comprises carbon monoxide gas at a concentration of at least 500 ppm.

16. The method of claim 1, wherein the pharmaceutical composition comprises carbon monoxide gas at a concentration of about 200 ppm to about 500 ppm.

17. The method of claim 1, wherein the pharmaceutical composition comprises carbon monoxide gas at a concentration of about 150 ppm to about 600 ppm.

18. The method of claim 1, wherein the pharmaceutical composition comprises carbon monoxide gas at a concentration of about 100 ppm to about 800 ppm.

19. The method of claim 1, wherein the pharmaceutical composition contains carbon monoxide gas at a concentration of about 10 ppm to about 1000 ppm.

20. The method of claim 1, wherein the pharmaceutical composition is administered to the patient through a ventilator.

21. The method of claim 7, wherein the pharmaceutical composition comprises carbon monoxide gas at a concentration of at least 50 ppm.

22. The method of claim 7, wherein the pharmaceutical composition comprises carbon monoxide gas at a concentration of at least 100 ppm.

23. The method of claim 7, wherein the pharmaceutical composition comprises carbon monoxide gas at a concentration of at least 250 ppm.

24. The method of claim 7, wherein the pharmaceutical composition comprises carbon monoxide gas at a concentration of at least 500 ppm.

25. The method of claim 7, wherein the pharmaceutical composition comprises carbon monoxide gas at a concentration of about 200 ppm to about 500 ppm.

26. The method of claim 7, wherein the pharmaceutical composition comprises carbon monoxide gas at a concentration of about 150 ppm to about 600 ppm.

27. The method of claim 7, wherein the pharmaceutical composition comprises carbon monoxide gas at a concentration of about 100 ppm to about 800 ppm.

28. The method of claim 7, wherein the pharmaceutical composition contains carbon monoxide gas at a concentration of about 10 ppm to about 1000 ppm.

29. The method of claim 7, wherein the pharmaceutical composition is administered to the patient through a ventilator.

30. The method of claim 10, wherein the pharmaceutical composition comprises carbon monoxide gas at a concentration of at least 50 ppm.

31. The method of claim 10, wherein the pharmaceutical composition comprises carbon monoxide gas at a concentration of at least 100 ppm.

32. The method of claim 10, wherein the pharmaceutical composition comprises carbon monoxide gas at a concentration of at least 250 ppm.

33. The method of claim 10, wherein the pharmaceutical composition comprises carbon monoxide gas at a concentration of at least 500 ppm.

34. The method of claim 10, wherein the pharmaceutical composition comprises carbon monoxide gas at a concentration of about 200 ppm to about 500 ppm.

35. The method of claim 10, wherein the pharmaceutical composition comprises carbon monoxide gas at a concentration of about 150 ppm to about 600 ppm.

36. The method of claim 10, wherein the pharmaceutical composition comprises carbon monoxide gas at a concentration of about 100 ppm to about 800 ppm.

37. The method of claim 10, wherein the pharmaceutical composition contains carbon monoxide gas at a concentration of about 10 ppm to about 1000 ppm.

38. The method of claim 10, wherein the pharmaceutical composition is administered to the patient through a ventilator.

39. The method of claim 11, wherein the atmosphere comprises carbon monoxide at a concentration of at least 50 ppm.

40. The method of claim 11, wherein the atmosphere comprises carbon monoxide at a concentration of at least 100 ppm.

41. The method of claim 11, wherein the atmosphere comprises carbon monoxide at a concentration of at least 250 ppm.

42. The method of claim 11, wherein the atmosphere comprises carbon monoxide at a concentration of at least 500 ppm.

43. The method of claim 11, wherein the atmosphere comprises carbon monoxide gas at a concentration of about 200 ppm to about 500 ppm.

44. The method of claim 11, wherein the atmosphere comprises carbon monoxide at a concentration of about 150 ppm to about 600 ppm.

45. The method of claim 11, wherein the atmosphere comprises carbon monoxide gas at a concentration of about 100 ppm to about 800 ppm.

46. The method of claim 11, wherein the atmosphere contains carbon monoxide at a concentration of about 10 ppm to about 1000 ppm.

47. The method of claim 11, wherein the patient is exposed to the atmosphere via a ventilator.

48. The method of claim 1, wherein the composition is in gas form and is administered to the patient via an artificial lung.

49. The method of claim 7, wherein the composition is in gas form and is administered to the patient via an artificial lung.

50. The method of claim 10, wherein the composition is in gas form and is administered to the patient via an artificial lung.

51. The method of claim 1, wherein the ileus is associated with surgery, parturition, intestinal ischemia, retroperitoneal hematoma, intraabdominal sepsis, intraperitoneal inflammation, fracture of the spine, ureteric colic, thoracic lesions, basal pneumonia, rib fracture, or myocardial infarction.

52. The method of claim 10, wherein the ileus is associated with parturition, intestinal ischemia, retroperitoneal hematoma, intraabdominal sepsis, intraperitoneal inflammation, fracture of the spine, ureteric colic, thoracic lesions, basal pneumonia, rib fracture, or myocardial infarction.

53. The method of claim 11, wherein the ileus is associated with surgery, parturition, intestinal ischemia, retroperitoneal hematoma, intraabdominal sepsis, intraperitoneal inflammation, fracture of the spine, ureteric colic, thoracic lesions, basal pneumonia, rib fracture, or myocardial infarction.

* * * * *

SEQUENCE LISTING

<160> NUMBER OF SEQ ID NOS: 31

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
atggcacagt caaggctgag a                                              21

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
cgctcctgga agatggtgat                                                20

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
gcccttcagg aacagctatg a                                              21

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
tgtcaacaac atcagtccca aga                                            23

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
cacctctaag cagagcacag                                                20

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
gggttccatg gtgaagtcaa c                                              21

<210> SEQ ID NO 7
<211> LENGTH: 21

```
<212> TYPE: DNA
<213> ORGANISM: Artificial Sequence
<220> FEATURE:
<223> OTHER INFORMATION: Primer

<400> SEQUENCE: 7
ggtgatcggt cccaacaagg a                                              21

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
cacgctggct cagccactc                                                 19

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
cgtggcgtcc atttacacct                                                20

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
ttagggcctc ctcctgagc                                                 19

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
ggagagattt ttcacgacac cc                                             22

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
ccatgcataa tttggacttg ca                                             22

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
```

```
ctctgcgatg ctcttccgag                                               20
```

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14

```
aaggatttgc tgcatggctg                                               20
```

<210> SEQ ID NO 15
<211> LENGTH: 17
<212> TYPE: DNA
<213> ORGANISM: Artificial Sequence
<220> FEATURE:
<223> OTHER INFORMATION: Primer

<400> SEQUENCE: 15

```
tgcaacagct cagcgca                                                  17
```

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16

```
gtcacagctt tcgagagact ggaa                                          24
```

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17

```
agagggaaat cgtgcgtgac                                               20
```

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18

```
caatagtgat gacctggccg t                                             21
```

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19

```
tcaattccag aaaccgctat ga                                            22
```

<210> SEQ ID NO 20
<211> LENGTH: 20
<212> TYPE: DNA
<213> ORGANISM: Artificial Sequence

```
<220> FEATURE:
<223> OTHER INFORMATION: Primer

<400> SEQUENCE: 20
caccagcatc agtcccaaga                                              20

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
caggtcgctc agggtcaca                                               19

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
cagaggcaag gaggaaacac a                                            21

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
cacaaagcag ccttgcagaa                                              20

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
agagcaggca gcatagcagt g                                            21

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
ctcactggca ggaaatcatc c                                            21

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
acctcgtgga gacgctttac a                                            21
```

```
<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
gtgacggcaa acatgacttc ag                                                22

<210> SEQ ID NO 28
<211> LENGTH: 18
<212> TYPE: DNA
<213> ORGANISM: Artificial Sequence
<220> FEATURE:
<223> OTHER INFORMATION: Primer

<400> SEQUENCE: 28
gccatcgggc atctggta                                                     18

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
ctgggaccca accctctga                                                    19

<210> SEQ ID NO 30
<211> LENGTH: 19
<212> TYPE: DNA
<213> ORGANISM: Artificial Sequence
<220> FEATURE:
<223> OTHER INFORMATION: Primer

<400> SEQUENCE: 30
acggtgtgta ccacacggc                                                    19

<210> SEQ ID NO 31
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 31
acggtatctg atcgtcttcg aacc                                              24
```